US012735754B2

(12) United States Patent
Geltz

(10) Patent No.: US 12,735,754 B2
(45) Date of Patent: Sep. 15, 2026

(54) MULTIPLEX NUCLEIC ACID DETECTION SYSTEM

(71) Applicant: Reditus Laboratories, LLC, Pekin, IL (US)

(72) Inventor: Joshua J. Geltz, Springfield, IL (US)

(73) Assignee: Reditus Laboratories, LLC, Pekin, IL (US)

( * ) Notice: Subject to any disclaimer, the term of this patent is extended or adjusted under 35 U.S.C. 154(b) by 1072 days.

(21) Appl. No.: 17/560,573

(22) Filed: Dec. 23, 2021

(65) Prior Publication Data

US 2023/0250494 A1 Aug. 10, 2023

Related U.S. Application Data

(60) Provisional application No. 63/130,362, filed on Dec. 23, 2020.

(51) Int. Cl.

*C12Q 1/70* (2006.01)
*C12N 9/22* (2006.01)
*C12Q 1/686* (2018.01)
*C12Q 1/6876* (2018.01)

(52) U.S. Cl.

CPC ............... *C12Q 1/701* (2013.01); *C12N 9/22* (2013.01); *C12Q 1/686* (2013.01); *C12Q 1/6876* (2013.01); *C12Y 301/26005* (2013.01); *C12Q 2600/16* (2013.01)

(58) Field of Classification Search

None

See application file for complete search history.

(56) References Cited

U.S. PATENT DOCUMENTS 6,015,664 A 1/2000 Henrickson et al.
6,881,835 B2 4/2005 Bai et al.
7,220,852 B1 * 5/2007 Rota ...................... A61K 39/12 435/235.1
2007/0207453 A1 9/2007 Gupta et al.
2011/0046001 A1 * 2/2011 Corbeil .................. C12Q 1/701 506/9

FOREIGN PATENT DOCUMENTS

CN 108220335 A * 6/2018
CN 111073861 A * 4/2020 ............. A61K 39/12
CN 111534514 A * 8/2020
CN 112458212 A * 3/2021 ........... C12Q 1/6851
CN 112760210 A * 5/2021 ............. C12Q 1/686
KR 1380414 B1 * 4/2014 ............. C12N 15/11
WO WO-2006121773 A2 * 11/2006 ........... C12Q 1/6883
WO WO-2007095155 A2 * 8/2007 ............. C12Q 1/701
WO WO-2013049891 A1 * 4/2013 ............. C12Q 1/686
WO WO-2018175868 A1 * 9/2018 ............... C12Q 1/70
WO WO-2019162532 A1 * 8/2019 ............. C12N 15/86
WO WO-2020076141 A1 * 4/2020 ............ A61K 39/12
WO WO-2021195637 A2 * 9/2021 ........... C12Q 1/6825

OTHER PUBLICATIONS

Mancini et al.: Multiplex Real-Time Reverse-Transcription Polymerase Chain Reaction Assays for Diagnostic Testing of Severe Acute Respiratory Syndrome Coronavirus 2 and Seasonal Influenza Viruses: A Challenge of the Phase 3 Pandemic Setting. J Infect Dis. Mar. 3, 2021;223(5):765-774. (Year: 2021).*

Stahl et al. IGI-LuNER: single-well multiplexed RT-qPCR test for SARS-CoV-2. medRxiv [Preprint]. Dec. 11, 2020: 2020.12.10. 20247338. (Year: 2020).*

Administration, F.a.D., TaqPath COVID-19 Combo Kit Emergency Use Authorization (EUA). 2020,Food and Drug Administration (FDA).

Altman, S., Ribonuclease P. Philosophical transactions of the Royal Society of London. Series B, Biological sciences, 2011. 366(1580): p. 2936-2941.

Biosystems, A., TaqMan® Fast Virus 1-Step MasternMix Product Insert. 2010, Life Technologies.

Brunet, A., et al., How does temperature impact the conformation of single DNA molecules below melting temperature? Nucleic Acids Research, 2017. 46(4): p. 2074-2081.

Ciarlitto C, Vittucci AC, Antilici L, Concato C, Di Camillo C, Zangari P, et al. Respiratory Syncityal Virus A and B; three bronchiolitis seasons in a third level hospital in Italy, Italian Journal of Pediatrics. 2019; 45(1): 115. doi: 10.1186/s13052-019-0704-0.

CLSI, User Verification of Precision and Estimation of Bias; Approved Guidelines—Third Edition, in CLSI document EP 15-A3, 2014, Clinical and Laboratory Standards Institute: Wayne, Pa.

Driessen, R. P. C., et al., Effect of Temperature on the Intrinsic Flexibility of DNA and Its Interaction with Architectural Proteins. Biochemistry, 2014. 53(41): p. 6430-6438.

Fernandes-Monteiro, A.G., et al., New approaches for the standardization and validation of a real-time qPCR assay using TaqMan probes for quantification of yellow fever virus on clinical samples with high quality parameters. Human vaccines & immunotherapeutics, 2015. 11(7): p. 1865-1871.

Gooskens, J, et al., Morbidity and Mortality Associated With Nosocomial Transmission of OseltamivirResistant Influenza A(HINI) Virus. JAMA, 2009. 301 (10): p. 1042-1046.

Green, W. D. and M.A. Beck, Obesity Impairs the Adaptive Immune Response to Influenza Virus. Ann Am Thorne Soc, 2017. 14(Supplement_5): p. S406-s409.

(Continued)

*Primary Examiner* — Thomas J. Visone
*Assistant Examiner* — Ruixue Wang
(74) *Attorney, Agent, or Firm* — Torrey Pines Law Group, PC

(57) ABSTRACT

A composition for detecting more than one target nucleic acid sequence in a nucleic acid sample by polymerase chain reaction (PCR) is provided. Also provided is a kit comprising the above composition with additional reagents for performing PCR using the plasmid, dye, primers and probes to detect the more than one target nucleic acid sequence. Additionally provided is a method for detecting more than one target nucleic acid sequence in a nucleic acid sample by polymerase chain reaction (PCR).

2 Claims, 27 Drawing Sheets

Specification includes a Sequence Listing.

(56) References Cited

OTHER PUBLICATIONS

Innings, A., et al., Multiplex real-time PCR targeting the RNase P RNA gene for detection and identification of *Candida* species in blood, Journal of clinical microbiology, 2007. 45(3): p. 874-880.
Katoh, K. and D. M. Standley, MAFFT multiple sequence alignment software version 7: improvements in performance and usability. Mol Biol Evol, 2013. 30( 4): p. 772-80.
Laham FR, Mansbach J M, Piedra PA, Hasegawa K, Sullivan A F, Espinola J A, et al. Clinical Profiles of Respiratory Syncytial Virus Subtypes A and B Among Children Hospitalized with Bronchiolitis. Pediatr Infect Dis J. 2017; 36(8):808-10. doi: 10.1097/INF.0000000000001596. PubMed PMID: 28383391.
Lapanje, S., Denaturation of globular proteins by guanidine thiocyanate I. Optical rotation in aqueous guanidine thiocyanate solutions. Biochimica et Biophysica Acta (BBA)—Protein Structnre, 1971. 243(3): p. 349-356.
Li, G., et al., Outcome of critically ill patients with influenza virus infection. Journal of Clinical Virology, 2009. 46(3): p. 1275-278.
Ljungman, P., et al., Influenza A in Immunocompromised Patients. Clinical Infectious Diseases, 1993. 17(2): p. 244-247.
Moghadami, M., A Narrative Review of Influenza: A Seasonal and Pandemic Disease. Iranian journal of medical sciences, 2017. 42(1): p. 2-13.
Owen, D. B. and Y.-M. Chou, Effect of Measurement Error and Instrument Bias on Operating Characteristics for Variables Sampling Plans. Journal of Quality Technology, 1983. 15(3): p. 107-117.
Pickett, B. E., et al., Virus pathogen database and analysis resource (ViPR): a comprehensive bioinformatics database and analysis resource for the coronavirus research community. Viruses, 2012. 4(11): p. 3209-3226.
Prevention, C.f.D.C.a., CDC 2019—Novel Coronavirus (2019-nCo V) Real-Time RT-PCR Diagnostic Panel. 2020, CDC. Division of Viral Diseases: Atlanta, Ga.
Prevention, C.f.D.C.a., CDC Influenza SARSCo V-2 (Flu SC2) Multiplex Assay, Instructions for Use. 2021, Centers for Disease Control and Prevention: Atlanta, Ga.
Prevention, C.f.D.C.a., Research Use Only CDC Influenza SARS-CoV-2 (Flu SC2) Multiplex Assay Primers and Probes, D.o.V.D. National Center for Immunization and Respiratory Diseases (NCIRD), Editor. 2021, CDC: Atlanta Ga.
Scientific, T. F., TaqPath™ COVID-19 Combo Kit Instructions for Use, in FDA.gov. 2020: Pleasanton, Calif.
Scientific, T. F., TaqPath™ COVID-19, FluA, FluB Combo Kit Instructions for Use. 2021, Thermo Fisher Scientific: Pleasanton, Calif.
Stadhouders, R., et al., The effect of primer-template mismatches on the detection and quantification of nucleic acids using the 5' nuclease assay. The Journal of molecular diagnostics: JMD, 2010. 12(1): p. 109-117.
Stepanenko, 0. V., et al., Distinct Effects of Guanidine Thiocyanate on the Structure of Superfolder GFP. PLOS ONE, 2012. 7(11): p. e48809.
Willman, D. Contamination at CDC lab delayed rollout of coronavirus tests. 2020; Available from: www.washingtonpost.com/investigations/contamination-atcdc- lab-delayed-rollout-of-coronavirus-tests/2020/04/ 18/#fd7d3824- 7139-11ea-aa80 c2470c6b2034_story.html.
Wingfield, P. T., Use of protein folding reagents. Current protocols in protein science, 2001. Appendix 3: p. Appendix-3A.
Wozniak, A., et al., A simple RNA preparation method for SARS-Co V-2 detection by RT-qPCR. Scientific Reports, 2020. 10(1): p. 16608.
Yee, K. F., Confidence interval approach for evaluating bias in laboratory methods. J Automat Chem, 1988. 10(3): p. 144-6.
Zhang, Y., et al., Influenza Research Database: An integrated bioinformatics resource for influenza virus research. Nucleic Acids Res, 2017, 45(DI): p. D466-d474.

* cited by examiner

FIG. 11B
InfA/SARS-CoV-2 Clinical Specimens (SARS-CoV-2)
Reditus FluV19 Multiplex
CDC FLuSC2 Multiplex
TaqMan COVID-19 FluA/B Mplex
Ct Value
0
10
20
30
40
AH-CH1
AH-CH2
AH-CH3
AH-CH4
AL-CH1
AL-CH2
AL-CH3
AL-CH4
AH-CL1
AH-CL2
AH-CL3
AL-CL1
AL-CL2
AL-CL3
AL-CL4
Specimen ID

FIG. 12B
InfB/SARS-CoV-2 Clinical Specimens (SARS-CoV-2)
Reditus FluV19 Multiplex
CDC FLuSC2 Multiplex
TaqMan COVID-19 FluA/B Mplex
Ct Value
0
10
20
30
BH-CH 1
BH-CH 2
BH-CH 3
BH-CH 4
BL-CH 1
BL-CH 2
BL-CH 3
BL-CH 4
BH-CL 1
BH-CL 2
BH-CL 3
BH-CL 4
BL-CL 1
BL-CL 2
BL-CL 3
BL-CL 4
Specimen ID

MULTIPLEX NUCLEIC ACID DETECTION SYSTEM

CROSS-REFERENCE TO RELATED APPLICATIONS

This application claims the benefit of U.S. Provisional Application No. 63/130,362, filed Dec. 23, 2020, and incorporated by reference herein in its entirety.

SEQUENCE LISTING

The instant application contains a Sequence Listing which has been submitted electronically in ASCII format and is hereby incorporated by reference in its entirety. Said ASCII copy, created on Dec. 22, 2021, is named REDI-01-US-_SL.txt and is 16,701 bytes in size.

BACKGROUND OF THE INVENTION

(1) Field of the Invention

The present invention relates to multiplex detection of nucleic acid sequences. More particularly, a composition and method for detecting nucleic acids in samples, e.g., clinical samples is provided. The composition and method provide highly sensitive assays with a very low background.

(2) Description of the Related Art

From the avian flu to severe acute respiratory syndrome (SARS) and other coronaviruses, such as the SARS COV-2 virus that causes the COVID-19 disease, respiratory viruses are currently the cause of great concern worldwide. Approximately 500 million non-influenza related viral respiratory tract infections (VRTI) episodes occur per year in the United States. These episodes have had an enormous cost in terms of lost lives, destroyed livelihoods, and negative financial impact throughout the world. Some respiratory virus illnesses cause a heavy burden in terms of morbidity and mortality, primarily among infants and the elderly. Moreover, it is often difficult to distinguish between the different possible causes of respiratory infections. Many viruses have similar symptomology and their precise diagnosis often requires high-complexity laboratory testing. Because of cost and technical limitations, such testing is sporadically performed and only for a limited number of viruses.

For example, traditional detection of respiratory viruses involves viral propagation in cell culture with or without direct immunoassays. Though very specific, this method has many disadvantages, as it often lacks sensitivity, is burdensome, requires skilled personnel, and takes between five and ten days before obtaining results. To more efficiently detect respiratory viruses, immunoassays have been developed that measure the titre of a virus using the reaction of an antibody to its antigen (e.g., various immunoassays are commercially available for influenza A detection). While relatively inexpensive and rapid, immunoassays are typically limited to the detection of a single virus species, and have reduced sensitivity and specificity. In addition, the development of such tests is impractical for some viruses having many subtypes including for example, enteroviruses.

In response to these deficiencies, certain tests have been developed that use multiplex polymerase chain reaction (PCR) to detect many viruses in one assay. Examples for such PCR-based tests are described in U.S. Pat. No. 6,015,664 to Henrickson, and U.S. Pat. No. 6,881,835 to Bai et al.

Both Henrickson and Bai utilize primers in a PCR process to amplify viral sequences if present in the sample. The amplified sequences are then hybridized to a solid support. One problem with these methods is the many required washing steps that can result in loss of signal and/or additional noise in the results, as well as increased time and cost for handling and detection. Furthermore, at least some of the detection methods can be cumbersome and have a relatively low sensitivity.

Although many kits and methods for respiratory virus detection are known in the art, all or almost all of them suffer from one or more disadvantages. Thus, there is still a need to provide kits and methods for detecting a plurality of respiratory viruses using a multiplex assay. As disclosed in US Patent Application Publication 2011/0046001, there are samples, kits, and methods that detect at least two respiratory viruses using a multiplexed diagnostic assay. According to US20110046001, the respiratory virus can be any DNA or RNA virus affecting the respiratory system including for example, an adenovirus, a coronavirus, an enterovirus, a rhinovirus, an influenza virus, a human metapneumovirus (HMPV), a human respiratory syncytial virus (HRSV), a human parainfluenza virus (HPIV), as well as all sero- and genotypes and combinations thereof. The limitations of the current state of the art assay process is exemplified by the ThermoFisher TaqPath® COVID multiplex assay process. In the current process, MS2 Phage is used as a control: MS2 phage must be kept at negative twenty degrees Celsius (−20° C.) for working stocks. MS2 phage is exogenous (added to each sample) and thus, is incapable of determining sample integrity. The stability and reproducibility of the MS2 phage control is poor. Additionally, in the current process, RNA control is used for PCR. Such RNA controls require manipulation before use (i.e. dilutions, which increase labor cost and subsequently decreases stability based on technical user error). RNA controls also increase workflow as illustrated and described in FIG. 1. Accordingly, a better control with improved accuracy, reduced labor, less paths for introduction of errors, and stability of the control at temperatures that are above the freezing point of water and can be maintained by a standard refrigeration cycle without requiring frozen temperatures.

Additionally, as illustrated in FIG. 2, background noise of the currently known assay increases variability in the analysis. It would be beneficial to reduce the background noise to reduce variability in the analysis and increase the sensitivity to the virus detection.

It is also important to recognize that some of the same symptoms of COVID-19 caused by the SARS-CoV-2 virus are similar to the symptoms of influenza viruses. Accordingly, a test that is merely capable of detecting only the presence of SARS-CoV-2 and is not capable of simultaneously determining the presence of influenza viruses is less beneficial to caregivers and their patients than a multiplex assay that allows for the simultaneous detection of influenza A, influenza B, and SARS-CoV-2.

It will also be appreciated that a test could have absolutely perfect accuracy and could be a foolproof process with absolutely no error path in the process, but if accessibility of the test is limited to hospitals and specialty clinics, the value of the perfect accuracy and foolproof process are greatly diminished because testing must be accessible to a large percentage of the population for the testing to be effective. Accordingly, in addition to improved accuracy of tests, the accessibility to tests and the convenience of patients in getting tested is also an important factor for an improved multiplex assay.

Other multiplex PCR assays include those described in US Patent Application Publication 20070207453.

BRIEF SUMMARY OF THE INVENTION

The present invention is based in part on the discovery that, in procedures using polymerase chain reaction (PCR) to detect more than one target nucleic acid sequence, e.g., nucleic acid from more than one virus in a mammalian tissue or fluid sample, certain methodologies and reagents provide results with surprisingly low background with higher sensitivity than achieved in the prior art.

Thus, in some embodiments, a composition for detecting more than one target nucleic acid sequence in a nucleic acid sample by polymerase chain reaction (PCR) is provided. In these embodiments, the composition comprises

- a plasmid comprising (a) a portion of each of the more than one target nucleic acid sequence, and (b) a sequence encoding a portion of a human housekeeping gene;
- a passive reference dye; and
- a set of two DNA primers and a DNA probe for each of the more than one target nucleic acid sequence and the portion of the RNase P, wherein each of the probes comprise a dye.

Also provided is a kit comprising the above composition with additional reagents for performing PCR using the plasmid, dye, primers and probes to detect the more than one target nucleic acid sequence.

Additionally provided is a method for detecting more than one target nucleic acid sequence in a nucleic acid sample by polymerase chain reaction (PCR). The method comprises

- obtaining the above kit;
- performing PCR on the sample and the plasmid;
- analyzing results from the PCR; and
- determining whether at least one of the more than one target nucleic acid sequence is in the sample.

BRIEF DESCRIPTION OF THE SEVERAL VIEWS OF THE DRAWINGS

FIG. 8B., Influenza B; FIG. 8C., SARS-CoV-2, and FIG. 8D., RNase P).

FIG. 9A: Analysis of clinical sample amplification for Influenza A using FluV19 (closed black bar), FLuSC2 (closed grey bar), or COVID-19 FluA/B (open white bar). FIG. 9B: Analysis of clinical sample amplification for Influenza B using FluV19 (closed black bar), FLuSC2 (closed grey bar), or COVID-19 FluA/B (open white bar). FIG. 9C: Analysis of clinical sample amplification for SARS-CoV-2 using FluV19 (closed black bar), FLuSC2 (closed grey bar), or COVID-19 FluA/B (open white bar). Each data point represents a single extraction and analysis to represent testing and analysis of clinical samples.

FIG. 10A: Analysis of clinical sample amplification for influenza A using FluV19 (closed black bar), FLuSC2 (closed grey bar), or COVID-19 FluA/B (open white bar). FIG. 10B: Analysis of clinical sample amplification for influenza B using FluV19 (closed black bar), FLuSC2 (closed grey bar), or COVID-19 FluA/B (open white bar). Each data point represents a single extraction and analysis to represent testing and analysis of clinical samples.

FIG. 11A: Analysis of clinical sample amplification for influenza A using FluV19 (closed black bar), FLuSC2 (closed grey bar), or COVID-19 FluA/B (open white bar). FIG. 11B: Analysis of clinical sample amplification for SARS-CoV-2 using FluV19 (closed black bar), FLuSC2 (closed grey bar), or COVID-19 FluA/B (open white bar). Each data point represents a single extraction and analysis to represent testing and analysis of clinical samples.

FIG. 12A: Analysis of clinical sample amplification for influenza B using FluV19 (closed black bar), FLuSC2 (closed grey bar), or COVID-19 FluA/B (open white bar). FIG. 12B: Analysis of clinical sample amplification for SARS-CoV-2 using FluV19 (closed black bar), FLuSC2 (closed grey bar), or COVID-19 FluA/B (open white bar). Each data point represents a single extraction and analysis to represent testing and analysis of clinical samples.

FIG. 13A: Analysis of clinical sample amplification for influenza A using FluV19 (closed black bar), FLuSC2 (closed grey bar), or COVID-19 FluA/B (open white bar). FIG. 13B: Analysis of clinical sample amplification for influenza B using FluV19 (closed black bar), FLuSC2 (closed grey bar), or COVID-19 FluA/B (open white bar). FIG. 13C. Analysis of clinical sample amplification for SARS-CoV-2 using FluV19 (closed black bar), FLuSC2 (closed grey bar), or COVID-19 FluA/B (open white bar). Each data point represents a single extraction and analysis to represent testing and analysis of clinical samples.

DETAILED DESCRIPTION OF THE INVENTION

Figure 1:
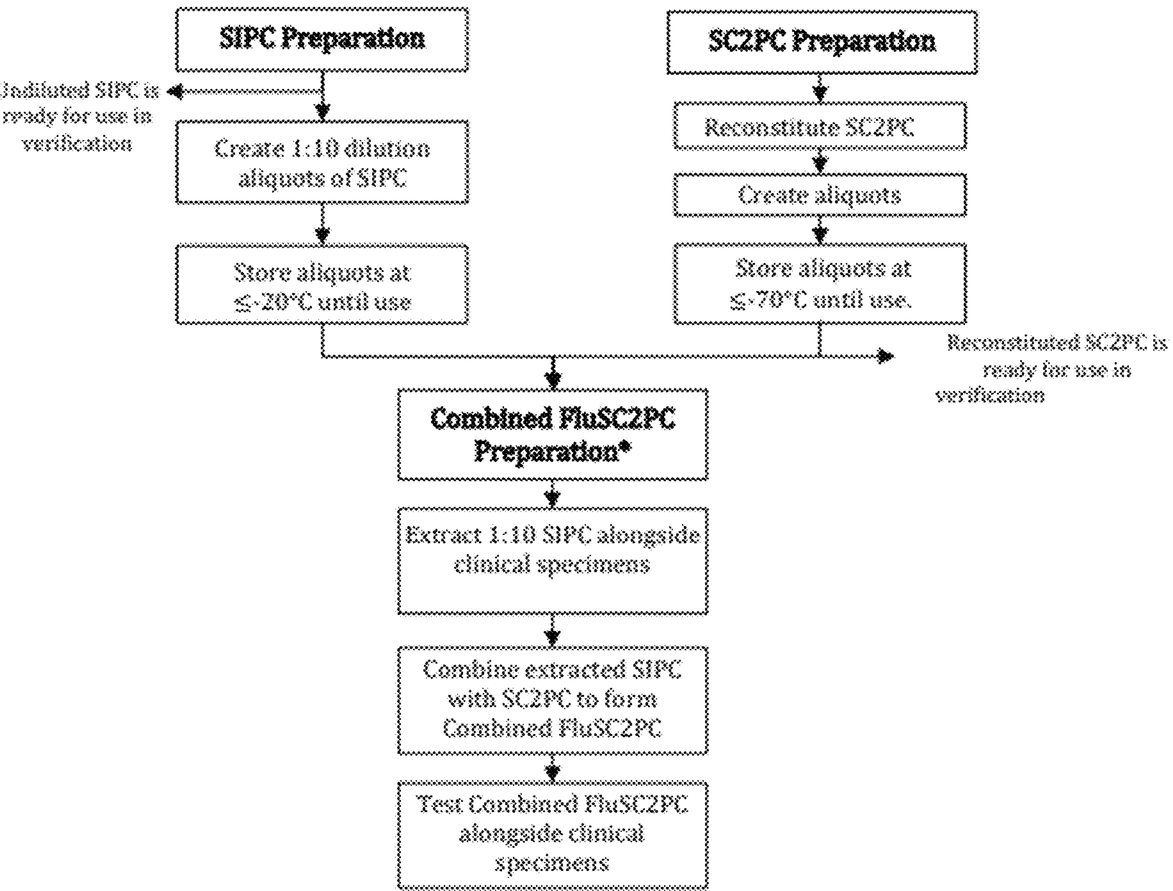
FIG. 1 is a flow chart showing the workflow of a prior art multiplex assay.

The present invention is based in part on the discovery that, in procedures using polymerase chain reaction (PCR) to detect more than one target nucleic acid sequence, e.g., nucleic acid from more than one virus in a mammalian tissue or fluid sample, certain methodologies and reagents provide results with surprisingly low background with less variability, while utilizing reagents that are simplified compared to prior art assays. See Example.

Thus, in some embodiments, a composition for detecting more than one target nucleic acid sequence in a nucleic acid sample by polymerase chain reaction (PCR) is provided. In these embodiments, the composition comprises

- a plasmid comprising (a) a transcribable target sequence of each of the more than one virus, and (b) a sequence encoding a portion of a human housekeeping gene;
- a passive reference dye; and
- a set of two DNA primers and a DNA probe for each of the more than one virus and the portion of the RNase P, wherein the probe comprises a dye.

These compositions can be utilized to detect any useful target nucleic acid sequence, including but not limited to sequences in environmental samples (e.g., wastewater, soil, river samples, ocean samples, etc.), or samples from living, inactive or deceased organisms such as archaea, prokaryotes or eukaryotes, e.g., protists, invertebrates, or vertebrates such as mammals, including humans. In some embodiments, the nucleic acid sample is from a mammalian tissue or fluid sample such as a biopsy, urine, feces, blood, mucus, etc. In particular embodiments, the mammalian tissue or fluid sample is a human nasal swab.

Nonlimiting examples of the target nucleic acid sequences are sequences associated with a disease, for example cancer or a disease of genetic etiology, e.g., genetic abnormalities in a fetus, child or adult. In some embodiments, the target nucleic acid sequence is from a disease organism such as a bacteria, fungus or protist.

In various embodiments, at least one of the more than one target nucleic acid sequence is from a virus. The virus in these embodiments can be any virus now known or later discovered. Non-limiting examples include the herpes virus (e.g., human cytomegalomous virus (HCMV), herpes simplex virus 1 (HSV-1), herpes simplex virus 2 (HSV-2), varicella zoster virus (VZV), Epstein-Barr virus), influenza A virus, influenza B virus, or a picornavirus such as Coxsackievirus B3 (CVB3). Other viruses include, but are not limited to, hepatitis B virus, HIV, poxvirus, hepadavirus, a retrovirus, and RNA viruses such as flavivirus, togavirus, coronavirus, Hepatitis D virus, orthomyxovirus, paramyxovirus, rhabdovirus, bunyavirus, filo virus, adenovirus, human herpesvirus, type 8, human papillomavirus, BK virus, JC virus, smallpox, hepatitis B virus, human bocavirus, parvovirus B19, human astrovirus, Norwalk virus, coxsackievirus, hepatitis A virus, poliovirus, rhinovirus, severe acute respiratory syndrome (SARS) virus, SARS-CoV-2 virus, hepatitis C virus, yellow fever virus, dengue virus, West Nile virus, Rubella virus, Hepatitis E virus, and Human immunodeficiency virus (HIV). In some cases, the virus is an enveloped virus. Examples include, but are not limited to, viruses that are members of the hepadnavirus family, herpesvirus family, iridovirus family, poxvirus family, flavivirus family, togavirus family, retrovirus family, coronavirus family, filovirus family, rhabdovirus family, bunyavirus family, orthomyxovirus family, paramyxovirus family, and arenavirus family. Other examples include, but are not limited to, hepadnavirus hepatitis B virus (HBV), woodchuck hepatitis virus, ground squirrel (Hepadnaviridae) hepatitis virus, duck hepatitis B virus, heron hepatitis B virus, herpesvirus herpes simplex virus (HSV) types 1 and 2, varicella-zoster virus, cytomegalovirus (CMV), human cytomegalovirus (HCMV), mouse cytomegalovirus (MCMV), guinea pig cytomegalovirus (GPCMV), Epstein-Barr virus (EBV), human herpes virus 6 (HHV variants A and B), human herpes virus 7 (HHV-7), human herpes virus 8 (HHV-8), Kaposi's sarcoma-associated herpes virus (KSHV), B virus Poxvirus vaccinia virus, variola virus, smallpox virus, monkeypox virus, cowpox virus, camelpox virus, ectromelia virus, mousepox virus, rabbitpox viruses, raccoonpox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, yabapox virus, flavivirus dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, Kyasanur Forest disease virus, Togavirus, Venezuelan equine encephalitis (VEE) virus, chikungunya virus, Ross River virus, Mayaro virus, Sindbis virus, rubella virus, retrovirus human immunodeficiency virus (HIV) types 1 and 2, human T cell leukemia virus (HTLV) types 1, 2, and 5, mouse mammary tumor virus (MMTV), Rous sarcoma virus (RSV), lentiviruses, Filovirus Ebola virus, Marburg virus, metapneumoviruses (MPV) such as human metapneumovirus (HMPV), rhabdovirus rabies virus, vesicular stomatitis virus, Bunyavirus, Crimean-Congo hemorrhagic fever virus, Rift Valley fever virus, La Crosse virus, Hantaan virus, Orthomyxovirus, influenza virus (types A, B, and C), Paramyxovirus, parainfluenza virus (PIV types 1, 2 and 3), respiratory syncytial virus (subtypes A and B), measles virus, mumps virus, Arenavirus, lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Punta toro virus (PTV), Tacaribe virus and Tamiami virus. In some embodiments, the virus is influenza A virus, e.g., strain H1N1.

In various embodiments, at least one of the more than one virus is an RNA virus, for example a respiratory virus. Specific examples include influenza A, influenza B, SARS-CoV-2, respiratory syncytial virus subtype A and respiratory syncytial virus subtype B.

In some embodiments, the more than one target nucleic acid sequence is RNA from at least two, three, four or five viruses selected from the group consisting of influenza A, influenza B, SARS-CoV-2, respiratory syncytial virus subtype A and respiratory syncytial virus subtype B. In certain embodiments, the more than one target nucleic acid sequence is RNA virus is influenza A, influenza B, and/or SARS-CoV-2. In other embodiments, the more than one target nucleic acid sequence is RNA virus is influenza A, influenza B, SARS-CoV-2, respiratory syncytial virus subtype A and/or respiratory syncytial virus subtype B.

As discussed in the Example, the inclusion of a passive reference dye for data normalization. Any appropriate dye, e.g., any fluorescent dye, can be utilized, provided the dye does not interfere with other dyes used in the assay, for example the dyes on the probes. The determination of a particular dye for any assay can be made by the skilled artisan without undue experimentation. Nonlimiting examples of useful dyes include FAM, TET, JOE, VIC, HEX, Cy3, NED, TAMRA, Cy3.5, ROX, Texas Red, Cy5, and Cy5.5. In specific embodiments, the passive reference dye is ROX (see Example).

The housekeeping gene is amplified as an endogenous control for extraction and sample integrity, to detect specimens compromised by, for instance, improper storage during transport or insufficient sampling. See Example. Any housekeeping gene in the sampled organism can be used in these embodiments. Nonlimiting examples of housekeeping genes that could be utilized in these compositions include RNase P, ACTB, B2M, GAPD, GUSB, HPRT1, PGK, PP1A, RPL13A, TBP, ubiquitin and TFRC. In some embodiments, more than one housekeeping gene is amplified. In specific embodiments, the housekeeping gene is RNase P. See Example.

Where the target nucleic acid sequence is an RNA, e.g., from an RNA virus or from an expressed gene in an organism, the invention compositions should provide for reverse transcription of the target RNA to DNA for PCR. Thus, in some embodiments, the composition further comprises reverse transcriptase.

In further embodiments where a target nucleic acid sequence is RNA, the composition further comprises total RNA, e.g., from a species from where the nucleic acid sample was derived. Where the sample was derived from a human, the total RNA is total human RNA. The use of defined concentrations of total RNA can be as a non-viral control that is extracted alongside clinical specimens to assess extraction efficiency and reverse transcriptase activity of the reverse transcriptase enzyme.

The selection of primers and probes for the each target nucleic acid sequence can be made by the skilled artisan without undue experimentation. In some embodiments, the primers and probes comprise DNA sequences comprising 1, 2, 3, 4, 5, 6, 7, 8, 9, 10, 11, 12, 13, 14, 15, 16, 17, 18, 19, or all 20 of SEQ ID NOs:1-20.

Similarly, the selection of the portion of each of the more than one target nucleic acid sequence can be made by the skilled artisan without undue experimentation. In some embodiments, wherein the plasmid comprises 1, 2, 3, 4, 5 or all 6 of SEQ ID NO:21-26. In specific embodiments the plasmid comprises a sequence at least 80%, 85%, 90%, 98%, 99%, or 100% identical to SEQ ID NO:28 or 29.

The present invention also provides a kit comprising the composition of claim 1 with additional reagents for performing PCR using the plasmid, dye, primers and probes to detect the more than one target nucleic acid sequence. When supplied as a kit, the different components of the composition can be packaged in separate containers and admixed immediately before use. Such packaging of the components separately can, if desired, be presented in a pack containing the composition. The pack may, for example, comprise metal or plastic foil such as a blister pack. Such packaging of the components separately can also, in certain instances, permit long-term storage without losing activity of the components.

Any reagents required or optional to detect the target nucleic acid sequences can be included in the kit, including, for example, enzymes, nucleotides, buffers, sterile water, etc.

In certain embodiments, kits can be supplied with instructional materials. Instructions may be printed on paper or other substrate, and/or may be supplied as an electronic-readable medium, such as a thumb drive, CD-ROM, DVD-ROM, video, audio, and the like. Detailed instructions may not be physically associated with the kit; instead, a user may be directed to an Internet web site specified by the manufacturer or distributor of the kit.

Also provided is a method for detecting more than one target nucleic acid sequence in a nucleic acid sample by polymerase chain reaction (PCR). The method comprises obtaining the above-identified kit;
performing PCR on the sample and the plasmid;
analyzing results from the PCR; and
determining whether at least one of the more than one target nucleic acid sequence is in the sample.

As discussed above, the target nucleic acid sequence can be from any organism or virus. In some embodiments, the more than one target sequence is each an RNA virus. In other embodiments, the more than one target sequence is each a respiratory virus, e.g., influenza A, influenza B, SARS-CoV-2, respiratory syncytial virus subtype A and/or respiratory syncytial virus subtype B.

Also as discussed above, the sample can be from any source. In some embodiments, the sample is from a nasal swab.

Other aspects of these methods are discussed in the Examples.

The compositions and methods provided herein provide multiple advantages over current assays. For example, the assays described in the Examples provide simplified reagents for quality control.

In the currently approved method, an RNA control is used to monitor both PCR and extraction efficiency. Preparation of the control RNA involves a complicated process that is highly susceptible to error and that needs to be repeated alongside each batch of clinical specimens.

For quality control, the invention assay, exemplified in the Examples, utilizes a plasmid DNA construct and total human RNA. The plasmid contains the same influenza and SARS-2-CoV genomic sequences used for detection during PCR. The plasmid can be supplied as a stable working stock that without any manipulation serves as a positive control for PCR efficiency and master mix composition. As a control for RNA extraction and cDNA synthesis, the assay uses total human RNA containing RNase P transcript. Since the RNase P target sequence is located in an exon and does not contain intron sequence, the use of human RNA provides a more accurate indication of RNA integrity and extraction than the DNA-containing human specimen control (HSC) used in the current CDC assay or the MS2 phage exogenous control employed by the ThermoFisher COVID19 Control protocol.

The use of separate controls for PCR efficiency and RNA extraction is also more informative for troubleshooting in the event of a quality control failure and since they require no manipulation before use, eliminates the possibility of technical errors made during their preparation. Table 1 below summarizes the workflow to troubleshoot quality control failures. The present assay demonstrates where the quality control failure could occur during the testing process.

TABLE 1

| CONTROL | RESULT | DIAGNOSIS |
|---|---|---|
| Thermo COVID19 Control and CDC: FluSC2 PC | Pass | None |
| | Fail | Error made in PTC preparation, poor extraction efficiency, or problem with PCR component |
| Reditus: Plasmid/RNA | Pass/Pass | None |
| | Pass/Fail | Poor extraction efficiency or problem with reverse transcription |
| | Fail/Pass | Problem with PCR primers/probes |
| | Fail/Fail | Problem with PCR master mix |

According to the innovative multiplex assay as particularly described above, as exemplified in the Examples, it will be appreciated that the present invention provides multiple benefits over the current state of the art process. Features and benefits of the present invention are juxtaposed with the state of the art in Table 2 below.

TABLE 2

| ThermoFisher TaqPath ® COVID Multiplex Assay Process | Multiplex Assay Innovation by Reditus |
|---|---|
| MS2 Phase as a control: MS2 phage must be | RNase P as the control-which produces better |

TABLE 2-continued

Figure 2:
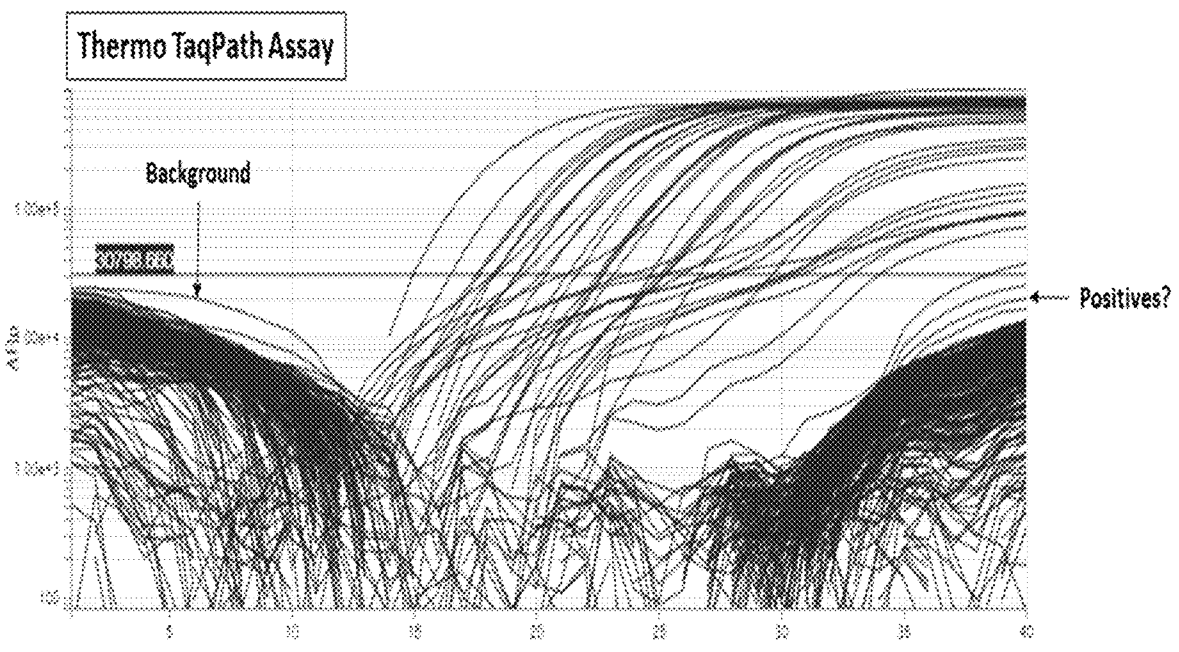
FIG. 2 is a graph showing representative results from a prior art multiplex assay.

| ThermoFisher TaqPath® COVID Multiplex Assay Process | Multiplex Assay Innovation by Reditus |
|---|---|
| stored at negative twenty degrees Celsius (−20° C.). MS2 phage is exogenous (added to each sample) and thus, is incapable of determining sample integrity. The stability and reproducibility of the MS2 phage control is poor. | reporting accuracy. This takes the risk of false negatives due to the ability to detect human cells within the sample. This also helps determine viability and quality of the specimen. |
| RNA control for PCR: RNA controls require manipulation before use (i.e. dilutions, which increase labor cost and subsequently decreases stability based on technical user error). RNA controls also increase workflow as illustrated and described in FIG. 1. | Plasmid based PCR control. This is stable at positive four degrees Celsius (+4° C.). There is no manipulation or dilution needed before use. This decreases user error, increases sensitivity, and decreases labor costs. |
| No passive reference dye: Lack of a passive reference dye in PCR reactions leads to increased background noise of the assay which increases variability in analysis (illustrated in FIG. 2). | A commercial PCR mix containing ROX passive reference dye is used to reduce background noise and increase the sensitivity in the SARS CoV2, Influenza A, and Influenza B detection. This is illustrated in FIG. 5. |
| Capable of detecting only SARS-CoV-2 | Four (4) targets-RNase P, SARS-CoV-2, Influenza A and Influenza B. |
| No ability to determine viability or quality of specimen sample if home collection is a preferred method due to lack of RNase P. | Utilizing RNase P, the viability and quality of the specimen sample can be determined, which is extremely advantageous in home sample collection without proctoring the collection method. |

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1. Development of a Robust Test System for the Detection of Influenza a, Influenza B, and SARS-CoV-2 by Multiplex RT-PCR

INTRODUCTION

An outbreak of pneumonia of unknown etiology in Wuhan City, Hubei Province, China was initially reported to WHO on Dec. 31, 2019. Chinese authorities identified a novel coronavirus (2019-nCoV), which has resulted in thousands of confirmed human infections in multiple provinces throughout China and many countries including the United States. Cases of asymptomatic infection, mild illness, and severe illness with an estimated 2.44-million deaths reported worldwide (Feb. 19, 2021, www.worldometers.info/coronavirus/).

In response to the COVID-19 pandemic, the CDC developed a singleplex RT-PCR assay for use in public health laboratories to detect the N1, N2, and N3 nucleoprotein sequences of COVID-19 (now referred to as SARS-CoV-2), and the p30 subunit of the human RNase P gene as a clinical sample control (Prevention, 2020). However, the CDC singleplex assay was not without limitations including contamination of the N3 primer/probe set leading to large number of inconclusive results (Willman, 2020) and the use of a singleplex assay which only allowed for 21 samples to be extracted and analyzed using a 96-well real-time instrument. The CDC dropped the contaminated N3 primer/probe set from the singleplex assay which increased the number of samples capable of being analyzed from 21 to 29 per run. However, early into the pandemic, it was realized that a singleplex assay approach was not feasible to test the sheer volume of specimens arriving at State Public Health Laboratories.

To increase extraction processes to enable laboratories to increase test capacity for SARS-CoV-2 testing, Thermo Fisher developed MagMax™ Viral and Pathogen Nucleic Acid Isolation Kits for use on the KingFisher Flex mangnetic particle processor to extract up to 96 specimens in 30-minutes. In addition, Thermo Fisher Scientific developed a multiplex RT-PCR assay for the detection of SARS-CoV-2 in clinical samples in response to the limitations of the CDC's singleplex assay and on Mar. 13, 2020, Thermo Fisher Scientific received EUA-approval by the Food and Drug Administration (FDA) for their TaqPath COVID-19 Combo Kit. The TaqPath COVID-19 Combo Kit contains exogenous extraction control reagents (MS2 phage), SARS-CoV-2 primers and probes, and the PCR master mix required to run the assay for detection of SARS-CoV-2 in clinical samples. Three individual primers and probe sets target ORF1ab, ORF9 (Nucleoprotein gene), and S (Spike glycoprotein gene) of SARS-CoV-2. In addition, the Combo Kit also contains primers and probe to detect MS2 phage RNA which is added to each sample prior to extraction to function as a metric for determining extraction success (Administration, 2020; Scientific, 2020).

However, despite the increased number of samples that the KingFisher platform could extract and the number of COVID-19 tests analyzed using the Combo Kit, multiple issues with the use of the testing process continued to provide significant challenges within the laboratory environment. First, the MS2 phage internal extraction control, is temperature sensitive, unstable, and demonstrated significant variability during extraction. The addition of exogenous extraction material (MS2 phage) provides no information surrounding the integrity of the specimen being extracted as no internal assessment of any human cell markers are available to verify human cells are present in the clinical sample. Second, high background noise associated with the lack of a passive-reference dye in the multiplex PCR mix leading to substantial variability in accurate analysis of sample amplification curves due to a wide signal-to-noise ratio (Scientific, 2020). Third, the TaqPath COVID-19 Combo Kit requires laboratory staff to perform several dilutions of the SARS-CoV-2 RNA template control for use as a PCR positive control. Stability and failures associated with dilutions of the COVID-19 Positive Template Control occur frequently leading to repeat testing, increased turn-around-time in test reporting, and increased accrued cost. Fourth, reagent cost and shortages have been a substantial issue during the pandemic. The cost for testing each sample for SARS-CoV-2 using Thermo Fisher reagents is —$3.18 per extraction and —$15.98 for analysis by PCR for a total reagent test cost of —$19.60 per sample. Lastly, the TaqPath COVID-19 Combo Kit only tests for SARS-CoV-2 in clinical samples (Id.). However, infection with influenza presents with similar clinical manifestations and is equally as clinically devastating as SARS-COV-2 to the elderly and immunocompromised (Gooskins et al., 2009; Green and Beck, 2017; Li et al., 2009; Ljungman et al., 1993; Moghadami, 2017).

To this end, we developed a robust and cost-effective test method for the detection of influenza A, influenza B, and SARS-CoV-2 which uses a defined Non-Viral Extraction control, and a stable and defined Positive Template Control. In addition, clinical samples can be extracted on current KingFisher Flex platforms and analyzed on current real-time instruments. We describe herein the process for implementation and validation of the FluV19 Multiplex RT-PCR assay performed at Reditus Laboratories.

Results

ReX Extraction Reagents are Equivalent to MagMax™ Viral/Pathogen Nucleic Acid Isolation Kits.

The current standards for nucleic acid extraction for detection of viral pathogens includes column-based manual extraction methods (Prevention, 2020; Prevention, 2021) and magnetic bead-based extractions on platforms (Scientific, 2020). Each of these extraction processes have proven track records in successfully extracting viral nucleic acids from clinical samples and have been approved for use in numerous laboratories for isolation of Influenza and SARS-CoV-2 from clinical samples (Prevention, 2020; Prevention, 2021; Scientific, 2020). However, limitations in the supply chain and the high cost of reagents have significantly impacted laboratories and their capacity to meet the needs of clinical testing of these pathogens.

To reduce the burden of reagent shortages and overall reagent cost, we investigated the possibility of developing cost-efficient extraction reagents to use on our laboratory's current KingFisher Flex extraction platforms to extract viral nucleic acids from clinical samples equivalent to the MagMax™ Viral/Pathogen Nucleic Acid Isolation Kit (MVP II) currently used within Reditus Laboratories for SARS-CoV-2 extraction.

The MagMax™ MVP II kit utilizes a combination of proteinase K digestion and guanidine thiocyanate (GTC) lysis buffer to degrade viral nucleoproteins and lyse cellular membranes to release nucleic acids which are then bound to magnetic beads and purified by the KingFisher platform. Specifically, during the extraction process outlined in the TaqPath COVID-19 EUA (Scientific, 2020), 265 μl of GTC-lysis buffer is added to 200 μl of specimen transferred into a 96-position deep well plate containing 5 μl of 20 mg/ml proteinase K (Id.). The specimen cocktail is then heated on the KingFisher platform at 65° C. for 5-minutes and mixed by the KingFisher platform. While proteinase K is efficient at cleaving peptide bonds and digestion of proteins, addition of high molar concentrations of GTC lysis buffer to specimens may inactivate proteinase K activity as guanidine thiocyanate is a strong protein denaturant (Lapanje, 1971; Stepanehko et al., 2012; Wingfeld, 2001). Therefore, we sought to formally test the hypothesis that particular extraction reagents (ReX) lacking proteinase K would work equivalent to the Thermo Fisher MagMax™ MVP II extraction process.

To test our hypothesis, a high-positive SARS-CoV-2 clinical sample previously extracted with MagMax™ MVPII extraction reagents on the KingFisher Flex and tested using the TaqPath COVID-19 Combo Kit was diluted in 0.5 log increments ranging from undiluted($10^{0}$) through $10^{-8}$ using a negative clinical sample as the diluent. This dilution series was based on a clinical sample which originally amplified each of the SARS-CoV-2 gene targets at: i. N-gene (Cq=12.5), ii. S-gene (Cq=12.9), iii. ORF1ab (Cq=12.1). Thus, it was anticipated that at the terminal $10^{-8}$ dilution the specimen Cq values for each viral gene target should amplify at approximately 40 cycles and be beyond the limit of detection of the assay. Each dilution of sample beginning at 10–0.5 dilution was extracted on the KingFisher extraction platform simultaneously using either the MagMax™ MVPII (EUA-approved) or Reditus Extraction reagents (Laboratory Developed).

Specimens extracted with the MagMax™ MVP II extraction reagents were performed in accordance with the EUA-approved method using the MVP_2Wash_200_Flex program on the KingFisher extraction platform (Scientific, 2020). Specifically, 200 μl of each sample was added to each well of a 96 deep well plate containing 5 μl of MS2 phage exogenous extraction control and 5 μl of proteinase K. Following transfer, each sample received 275 μl of lysis reagents consisting of 265 μl of MagMax™ Binding Solution and 10 μl of MVP II binding beads. Samples were extracted and washed with 500 μl MagMax™ wash solution followed by wash in 1 ml of 80% ethanol and eluted in 50 μl of elution buffer.

Specimens extracted using Reditus extraction reagents (ReX) were also extracted on the KingFisher extraction platform using the MVP_2Wash_200_Flex program. For specimen extraction, a total of 280 μl of lysis reagents consisting of 265 μl of ReX Lysis Buffer (Rex-LB), 5 μl of MS2 Phage exogenous extraction control, and 10 μl of MVP II magnetic beads were added to each well of a 96-position deep well plate and 200 μl of each specimen dilution being dispensed directly into the lysis buffer. Following specimen transfer, magnetic bead binding was enhanced by transferring 640 μl of 80% Ethanol to each well. Samples were extracted and washed with 500 ReX wash buffer (ReX-WB) followed by wash in 1 ml of 80% ethanol and eluted in 50 μl of Reditus elution buffer (ReX-EB).

The isolated nucleic acid from each extraction process was amplified simultaneously using PCR reaction mix of the EUA-approved TaqPath COVID-19 Combo Kit™ (Id.) and amplified on a single reaction plate using a QuantStudio 12K Flex real-time instrument and analyzed using Applied Biosystems Design and Analysis Software. All data were analyzed and the mean±sem of n=3 replicates per specimen dilution are presented in FIGS. 5A, 5B, 5C and 5D.

Figures 5A, 5B:
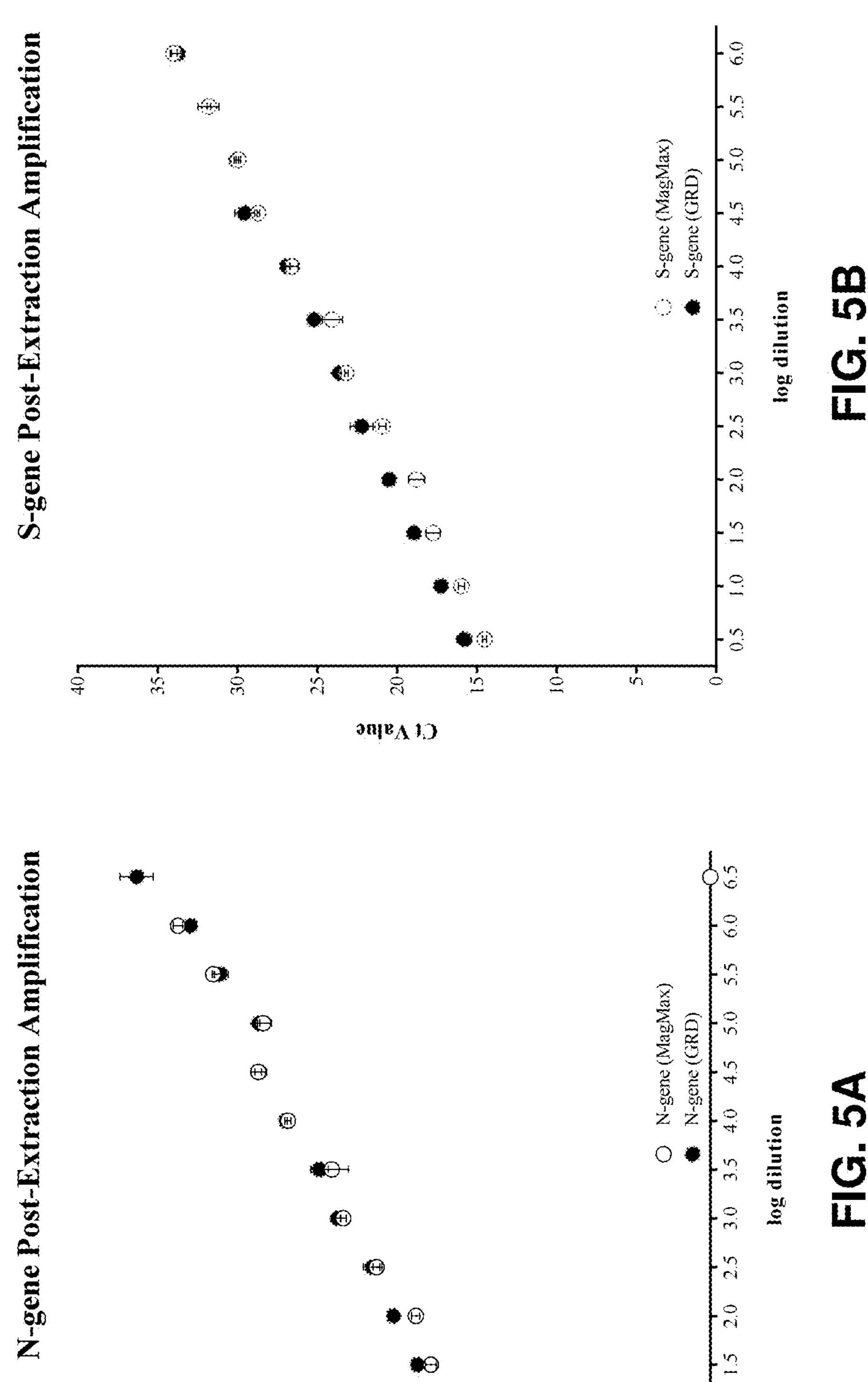
FIGS. 5A, 5B, 5C and 5D are graphs showing Reditus extraction reagents (ReX) for the invention assay are equivalent to those in MagMax™ Viral and Pathogen Nucleic Acid Isolation Kits. A single high-positive (low Cq) SARS-CoV-2 positive clinical specimen was diluted in 0.5 log increments using a clinical-negative specimen as diluent. Each dilution was extracted in triplicated using either Reditus extraction reagents (ReX) or MagMax reagents. Extracted nucleic acid was amplified using Thermo TaqPath COVID-19 Combo Kit RT-PCR reagents and analyzed using Applied Biosystems Design & Analysis Software. SARS-CoV-2 gene targets (FIG. 5A. N-gene, FIG. 5B. S-gene, FIG. 5C. ORF1ab) and the MS2 phage (FIG. 5D) were analyzed and graphed using the mean±sem of each replicate dilution.

Dilutions of the clinical specimen extracted using the MagMax™ extraction reagents demonstrated successful amplification of the SARS-CoV-2 N-gene target from $10^{-0.5}$ (Cq=14.32±0.007) through $10^{-6.0}$ (Cq=33.66±0.30) dilution with the anticipated ~1.5 cycle difference between dilutions (FIG. 5A). MagMax™ was unable detect amplification of the N-gene beyond the $10^{-6.0}$ dilution (FIG. 5A). The same dilutions of clinical specimen extracted using ReX reagents detected SARS-CoV-2 N-gene amplification at equivalent cycles for each dilution (FIG. 5A). However, the range of detection for the N-gene for specimen dilutions extracted with ReX reagents also detected amplification of N-gene at the $10^{-6.5}$ dilution (Cq=36.25±1.05) which was not detected in the same specimen dilution extracted with MagMax™ reagents (FIG. 5A). These data suggest that the ReX extraction reagents, which lack the addition of proteinase K, do lead to a decrease in extraction efficiency to detect the SARS-CoV-2 N-gene in the same dynamic range of viral loads as the MagMax™ extraction reagents which require the addition of proteinase K.

Similarly, dilutions of the clinical specimen extracted using the MagMax™ extraction reagents demonstrated successful amplification of the SARS-CoV-2 S-gene target from $10^{-0.5}$ (Cq=14.52±0.012) through $10^{-6.0}$ (Cq=34.00±0.22) dilution with the anticipated ~1.5 cycle difference between dilutions (FIG. 5B). MagMax™ was unable detect amplification of the S-gene beyond the $10^{-6.0}$ dilution (FIG. 5B). The same dilutions of clinical specimen extracted using ReX reagents detected SARS-CoV-2 S-gene amplification at equivalent cycles for each dilution (FIG. 5B). These data suggest that the ReX extraction reagents, which lack the addition of proteinase K, in the extraction efficiency to detect the SARS-CoV-2 S-gene in the same dynamic range of viral loads as the MagMax™ extraction reagents which require the addition of proteinase K.

Figures 5C, 5D:
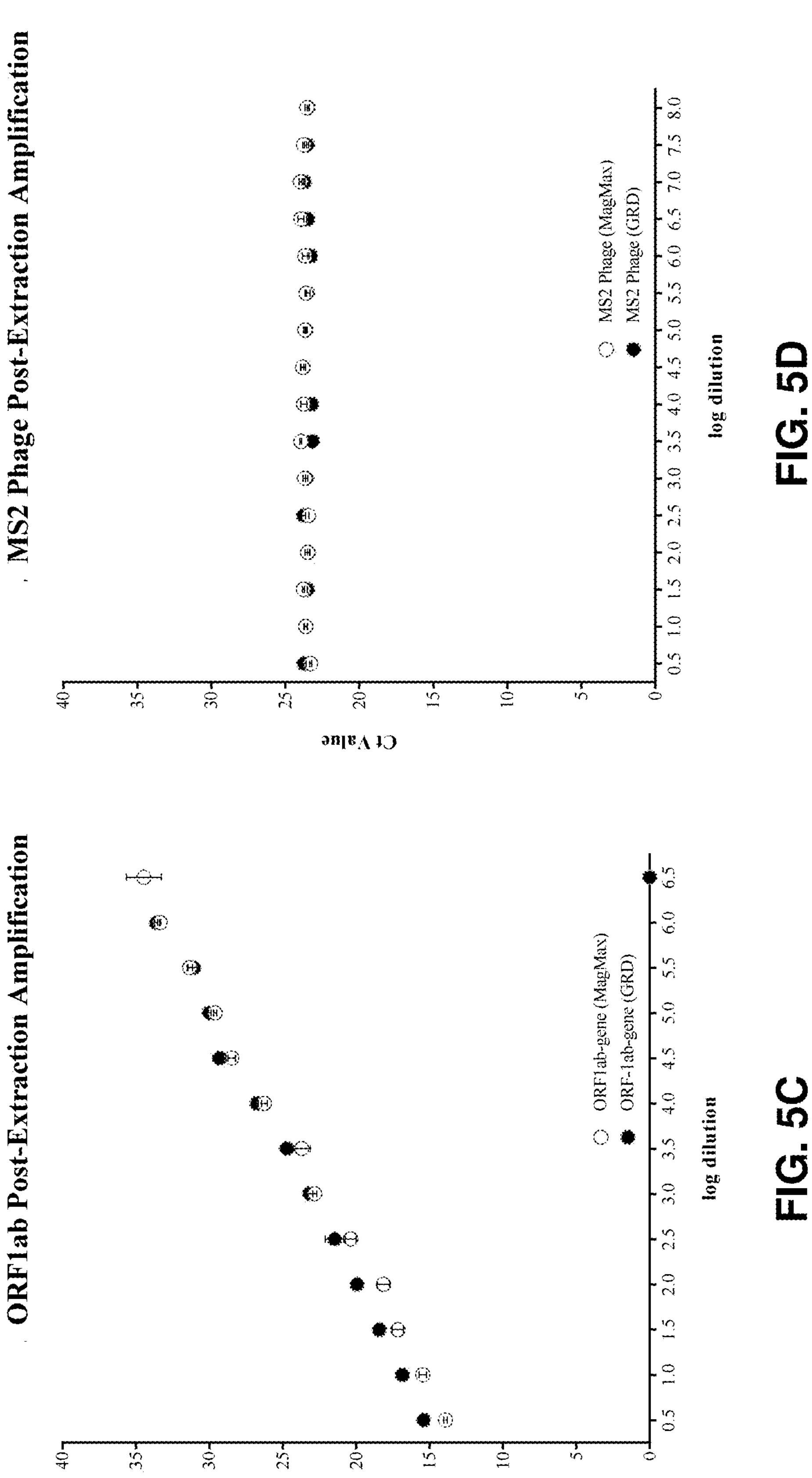

For ORF1ab amplification, ReX Reagents demonstrated successful amplification of ORF1ab from $10^{-0.5}$ (Cq=15.41±0.20) through $10^{-6.0}$ (Cq=33.64±0.10) with the anticipated ~1.5 cycle difference between dilutions (FIG. 5C). MagMax™ reagents demonstrated similar detection from $10^{-0.5}$ through $10^{-6.0}$ and at the additional $10^{-6.0}$ dilution (Cq=34.47±1.19) (FIG. 5C).

Lastly, the overall extraction efficiency of both extraction reagents was assessed by the amplification of the internal exogenous MS2 phage control which is added at equivalent volumes/concentrations to each specimen being extracted. At all dilutions ($10^{-0.5}$ through $10^{-8.0}$) both MagMax™ and ReX extraction reagents isolated equivalent MS2 phage from each specimen as indicated by a Cq<0.5 variation in MS2 amplification between each respective dilution. Thus, both MagMax™ and Rex reagents performed equivalently at extraction of the internal MS2 phage control (FIG. 5D).

While the additional dilution at $10^{-6.5}$ was detected by MagMax™ for ORF1ab and the additional dilution at $10^{-6.5}$ was detected by ReX for N-gene, these did not impact the overall detection of any clinical specimen dilution by either extraction reagent. Specifically, positive identification of SARS-CoV-2 using the TaqPath COVID-19 Combo Kit™ relies on positive amplification for 2 of the 3 viral gene targets and the amplification of the internal MS2 phage internal control (Id.). Thus, both extraction reagents performed equivalently and were not statistically significant in the recovery and amplification of each viral- and control-targets at each dilution. These data suggest that the Reditus extraction reagents (ReX) used on the KingFisher Flex extraction platform may be used as a cost-effective alternative to commercially available MagMax™ extraction reagents.

Samples Extracted with ReX Reagents Have Less Variability Than MagMax™ Extraction.

The previous data suggest that both ReX and MagMax™ extraction reagents can recover equivalent amount of SARS-CoV-2 and MS2 phage RNA across an equivalent dynamic range of viral load from clinical specimens (FIGS. 5A, 5B, 5C and 5D). However, the reproducibility of extraction efficiency (i.e. variance) was not compared over time. To this end, an experiment was conducted to estimate the systematic measurement of error (i.e. bias) of ReX reagents relative to the EUA-approved MagMax™ extraction reagents.

To address the overall bias in extraction efficiency, n=5 independent clinical samples were identified which were previously reported as positive for SARS-CoV-2 and which amplified between 27 to 29 cycles for each of the viral gene targets using the TaqPath COVID-19 Combo Kit™. Over 5 Days, each specimen was extracted in triplicate using both ReX and MagMax™ methods and tested by RT-PCR using the TaqPath COVID-19 Combo Kit™. Thus, a Σ=75 data points were generated for each extraction method and the mean±sem for each data set per day, was analyzed and compared against the Day 0 ($T_0$) sample. The variation for each extraction method was assessed by analyzing each sample for the mean ($\bar{x}$), stdev (α), and sem ($\sigma_{\bar{x}}$) of each sample over the 5-Day period (FIGS. 6A, 6C, 6E, 6G). Each of the independent measurements per sample over 5-Days (Σ=75) also represents the statistical "true value ($V_T$)" for each sample and was used to calculate the experimental bias ($V_B$) for both extraction processes as defined by $$V_B = \frac{\sum[V_E - V_{T1}, V_E - V_{T2}, V_E - V_{T3} \ldots V_E - V_{T25}]}{DF}$$

(CLSI, 2014; Owen and Chou, 1983; Yee, 1988).

Figure 6B:
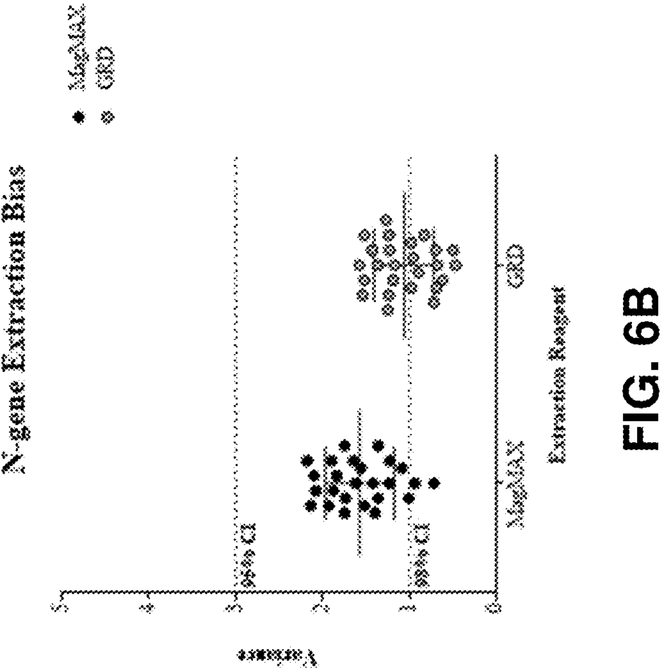
FIGS. 6A, 6B, 6C, 6D, 6E, 6F, 6G and 6H are graphs showing that the Reditus extraction reagents (ReX) demonstrate less variability in extraction than MagMax™ Viral and Pathogen Nucleic Acid Isolation Kits. A total of n=5 SARS-CoV-2 positive specimens were identified and extracted in triplicate over 5 Days (7=25 data points) using either Reditus extraction reagents (ReX) or MagMax reagents. Extracted nucleic acid was amplified using Thermo TaqPath COVID-19 Combo Kit RT-PCR reagents and analyzed using Applied Biosystems Design & Analysis Software. Each viral gene target and extraction target (MS2 phage) was analyzed for the mean±sem of each triplicate per day (n=25 averaged data points) and is presented in FIGS. 6A, 6C, 6E and 6G. The variance in extraction was assessed in each gene target detection FIGS. 6B, 6D, 6F, and 6H) over 5-Days (Σ=75) and represents the statistical "true value ($V_T$)" for each sample. The experimental bias ($V_B$) was calculated for each extraction process as defined by $$V_B = \frac{\sum[V_E - V_{T1}, V_E - V_{T2}, V_E - V_{T3} \ \ldots \ V_E - V_{T25}]}{DF}.$$
Figure 6A:
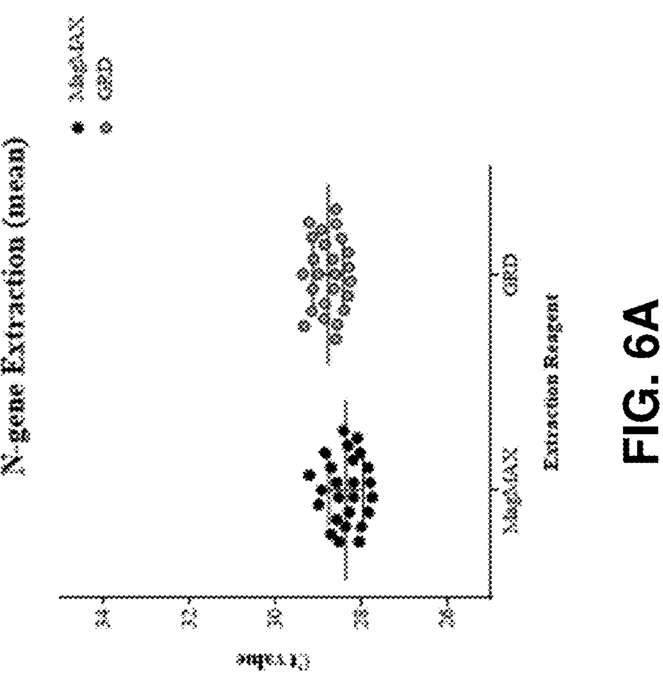
Figure 6D:
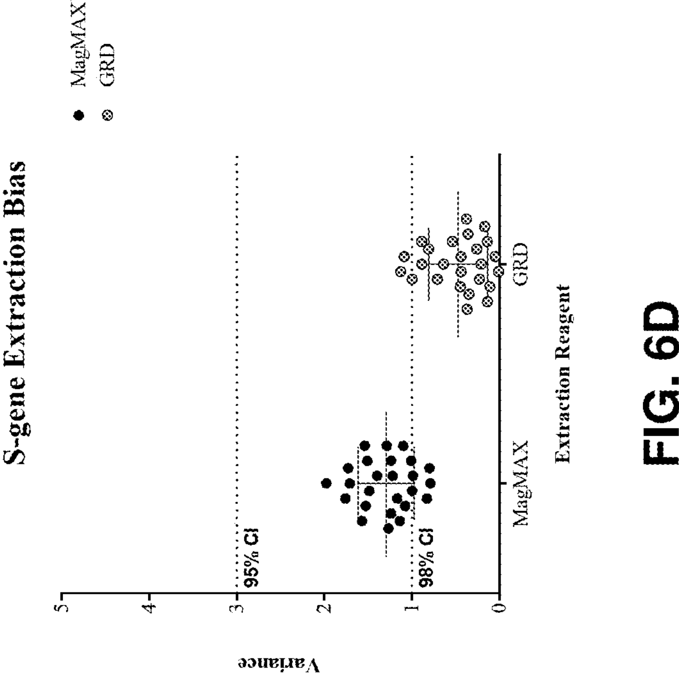
Figure 6C:
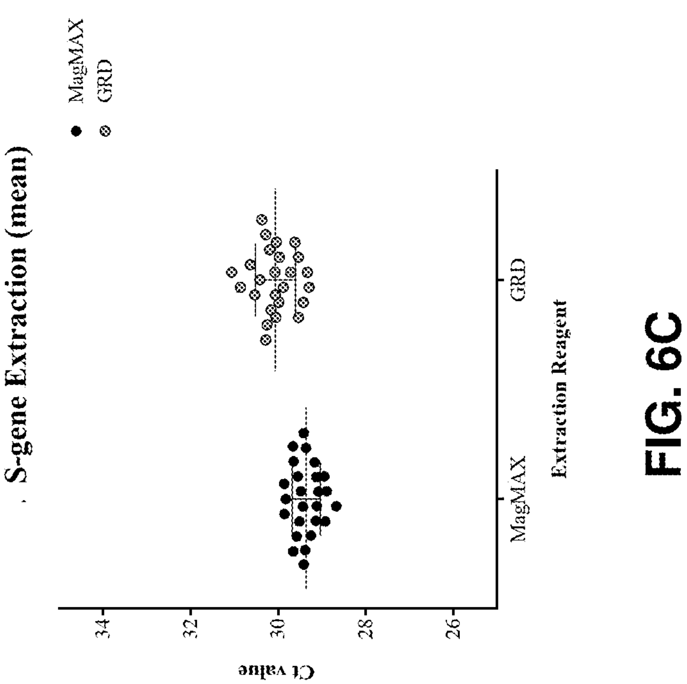
Figure 6F:
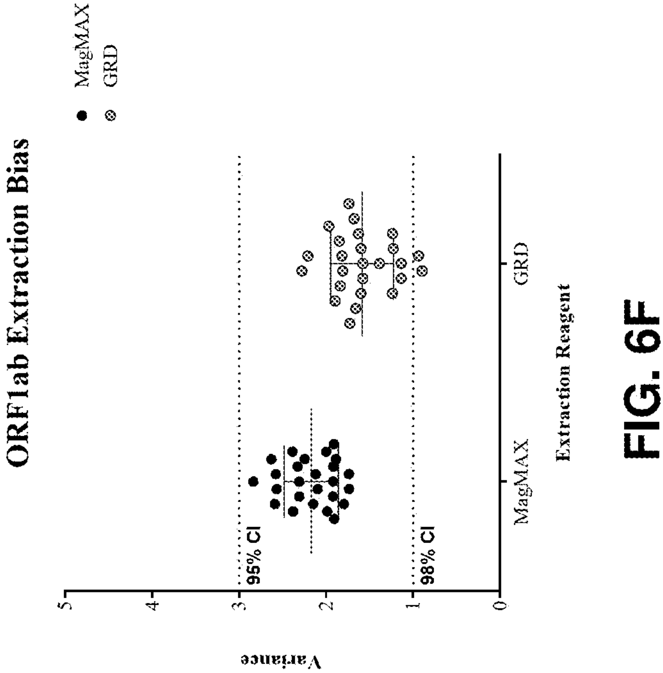
Figure 6E:
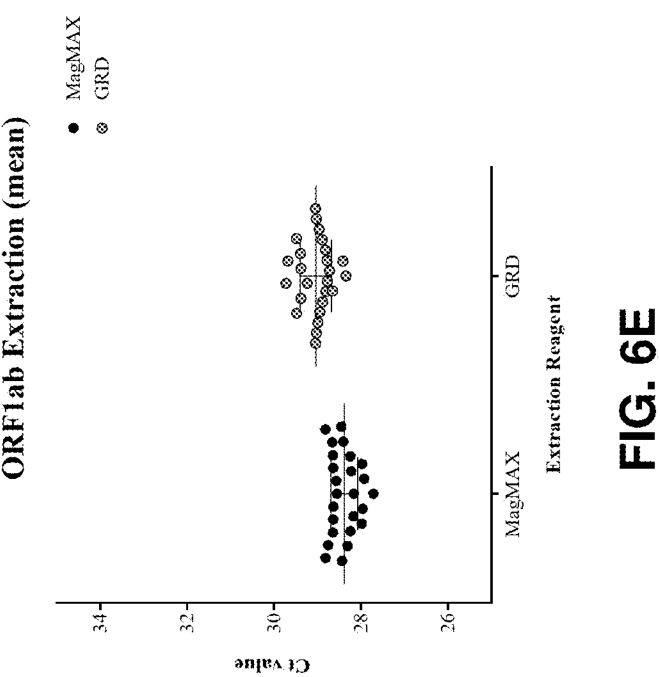
Figure 6H:
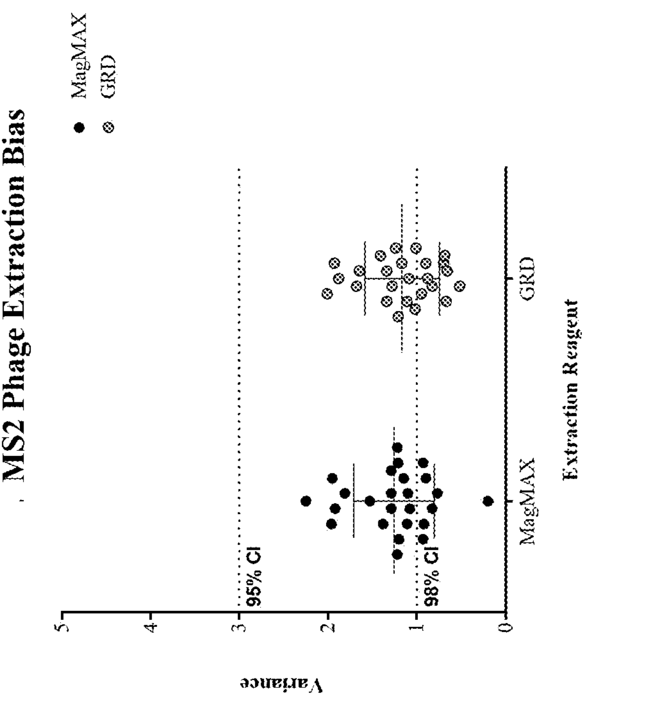
Figure 6G:
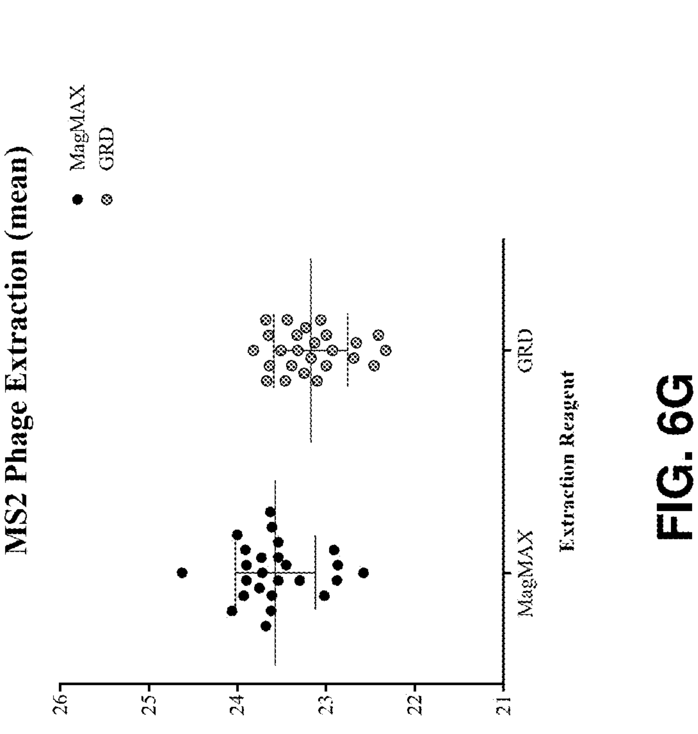

Analysis of the overall mean ($\bar{x}$), stdev (σ), and sem ($\sigma_{\bar{x}}$) of the Σ=75 data points collected from each of the viral targets and MS2 phage extraction control for the respective extraction process (MagMax™ vs. ReX) indicate that detection of viral gene target was equivalent between extraction reagents (FIGS. 6A, 6C, 6E, 6G). Specifically, analysis of N-gene amplification following MagMax™ extraction across n=5 Days demonstrated an average Cq=28.37±0.07 and an average Cq=28.79±0.68 by ReX extraction (FIG. 6A). Analysis of S-gene following MagMax™ extraction across all timepoints indicated an average Cq=29.36±0.64 amplification and Cq=30.07±0.91 following extraction with ReX reagents (FIG. 6C). Similarly, ORF1ab amplified with an average Cq=28.39±0.62 after MagMax™ extraction and Cq=29.04±0.71 following ReX reagent extraction (FIG. 6E). Lastly, MagMax™ extraction reagents produced an average Cq=23.57±0.90 for amplification of MS2 phage across n=5 Days and an average Cq=23.17±0.08 following ReX extraction across the same timepoints and samples (FIG. 6G).

The experimental bias in each extraction process was analyzed using the data collected in FIGS. 6A, 6C, 6E and 6G and is presented in FIGS. 6B, 6D, 6F and 6H for each of the respective targets. Specifically, the initial amplification results for each sample represented the estimated expected value ($V_E$) using each test method and was compared to the error of each recurrent value over the 5-Days of analysis (refer to bias equation). Bias in an experimental system is related to the confidence interval of the coefficient in variation (CI) where bias ≤1 represents a highly unbiased system with a ~99% CI. Experimental systems/assays which demonstrate 1<bias ≤3 indicate an unbiased system with a ~95% CI. Any system where bias >3 indicates a biased system which falls below the 95% confidence interval indicating that the system contains bias and is unlikely to generate consistent results (CLSI, 2014; Owen and Chou, 1983; Yee, 1988).

When these metrics were applied to assess the overall bias in the extraction systems, samples extracted with Mag- Max™ reagents all fell within above the 95% confidence interval range for all viral and MS2 phage control targets amplified (N=1.58±0.08, CI=~96.8%; S=1.30±0.63, CI=97.6%; ORF1ab=2.17±0.06, CI=~96.9%; MS2=1.26±0.09, CI=~97.6%) (FIGS. 6B, 6D, 6F and 6H, respectively).

When the same analysis to estimate bias in specimens extracted with ReX reagents, the overall bias in extraction performance was significantly less following amplification all viral gene and control targets than observed by extraction with MagMax™ (FIGS. 6B, 6D, 6F and 6H, respectively). Specifically, reproducibility of amplification of N-gene was achieved with a CI=~97.8% (1.06±0.06; FIG. 6B). Similarly, analysis of S-gene amplification reproducibility had a CI=~99.0% (0.48±0.06; FIG. 6D) and ORF-1ab demonstrated a CI=~97.1% (1.58±0.7; FIG. 6F). Consistent with MagMax™ extraction, reproducibility of MS2 amplification using ReX reagents was equivalent to that of MagMax™ with an overall CI=~97.6 (1.20±0.8; FIG. 6H).

The accumulation these data indicate that the Reditus extraction reagents (ReX) demonstrate equivalence in extraction efficiency on the KingFisher Flex magnetic particle processor as the MagMax™ commercial standard extraction reagents extracted on the same platform. This inference is based on the ability of ReX reagents to 1) accurately detect the each of the SARS-CoV-2 specimens at the same dilutions detected following extraction using the MagMax™ extraction reagents (FIGS. 5A, 5B, 5C and 5D) with less than a 1.5 cycle difference in amplification between comparable dilutions, and 2) decrease the overall extraction variability of extraction as determined through estimation of bias which tested the extraction efficiencies of both ReX an MagMax™ extraction reagents using the same n=5 specimens extracted and amplified over 5 Days (FIGS. 6A-6H). Thus, ReX reagents can be used in lieu of MagMax™ reagents for extraction of viral nucleic acids from clinical specimens for analysis by RT-PCR.

Total Genomic RNA is Reliable and Robust for Use as a Non-Viral Control (NVC).

We were interested to expand testing of SARS-CoV-2 to include simultaneous testing for Influenza A and Influenza B in clinical specimens. Aside from the limitation that the COVID-19 Combo Kit™ only tests for SARS-CoV-2, a significant limitation of the COVID-19 Combo Kit™ for the detection of SARS-CoV-2 is addition of the MS2 RNA bacteriophage (phage) as exogenous extraction control in each sample being extracted. Federal clinical testing regulations require that each test system that has an extraction phase for analysis by molecular methods must contain at least two control materials: i) one that can detect errors in the extraction process, and ii. one for detecting errors in amplification (42 CFR 493.1256). While the MS2 phage extraction control provided as part of the TaqPath COVID-19 Combo Kit™ meets the requirements specified in 42 CFR 493.1256, amplification of MS2 phage RNA in each sample does not provide any indication in either the quality of the sample being tested, nor the accuracy of the test collection method being used. Specifically, samples which have not been properly collected may not have a sufficient number of human epithelial cells contained with the sample to accurately detect viral pathogens (i.e. SARS-CoV-2, Influenza, etc.). Likewise, specimens may be contaminated or contain inhibitors which can affect accurate detection by PCR.

The human ribonuclease protein (RNase P) is present in every human cell and is required for normal function of viable cells (Altman, 2011). The p30 subunit of the human RNase P gene is currently widely employed in numerous clinical molecular assays as an internal control to assess sample integrity while detecting analytes by molecular analysis and the primers and probes for these assays are well established (Prevention, 2021; Fernandes-Monteiro et al., 2015; Innings et al., 2007; Wozniak et al., 2020). Therefore, we were interested to explore the use of the p30 subunit of RNase P as an internal extraction control for the development of a multiplex RT-PCR assay. Since an extraction control must be present which can detect errors in the extraction process (42 CFR 493.1256) it would be possible to use diluted total human DNA in aqueous phase to include as a non-viral control (NVC) to be extracted alongside clinical specimens and analyzed by PCR using primers and probes to detect RNase P present in both the NVC and clinical specimens. Since the viral pathogens we were interested in developing an assay for are single-stranded RNA viruses (ssRNA), reverse transcription of the viral genomes (i.e. influenza, SARS-CoV-2) is used to convert viral RNA to cDNA for amplification by PCR. Thus, using total human DNA as a source of RNase P for a non-viral extraction control (NVC) would not assess the reverse transcriptase activity during RT-PCR. We hypothesized that human total genomic RNA could be used as the source of RNase P for a NVC as it would meet the control requirements specified within 42 CFR 493.1256 for extraction and amplification. We were interested in this possibility as an RNA RNase P control approach could also be used to define a specific concentration used in extraction to assess overall extraction efficiency based on the amplification profile of the RNA control material. To this end, we performed a series of tests to determine the best concentration of total human RNA for use which demonstrated consistent amplification values following extraction, and which determined the overall stability of the NVC over time.

Primer sequences for RNase P were obtained from the Center for Disease Control and Prevention (CDC) real-time Measles RT-PCR protocol (Prevention, 2021) and purchased through GenScript (Refer to Materials and Methods; SEQ ID NOs:1-10). Human total RNA control (50 ng/μl) was purchased from Applied Biosystems (Cat #4307281, Foster City, CA). Total control RNA was diluted to a starting concentration of 1.0 ng/μl in 10 mM Tris and serial diluted in a final volume of 1 ml at 0.5 log increments in Tris (pH 8.0) from 1.0 ng/μl to 0.0316 ng/μl. A total of 200 μl of each dilution was extracted in triplicate using ReX reagents on the KingFisher extraction platform and analyzed by RT-PCR on a QuantStudio 12K Flex real-time instrument using 5 μl of elution in a total reaction volume of 25 μl (Table 3). An amplification range of 28±2 cycles for RNase P was pre-established to: i) maximize the total number of NVC reactions capable of being generated from the stock 50 ng/μl, ii) establish a defined amplification range to monitor extraction efficiency, and iii) identify stability fluctuations during clinical implementation of the NVC.

TABLE 3

RNase P RT-PCR Reaction Mix

| Description | 1x (μl) | 10x (μl) | 15x (μl) |
|---|---|---|---|
| RNase P Fwd (9 μM) | 0.54 | 5.4 | 8.1 |
| RNase P Rvs (9 μM) | 0.54 | 5.4 | 8.1 |

TABLE 3-continued

| RNase P RT-PCR Reaction Mix | | | |
|---|---|---|---|
| Description | 1x (μl) | 10x (μl) | 15x (μl) |
| RNase P Probe (3 μM) | 0.18 | 1.8 | 2.7 |
| 4X Fast Virus Enzyme Mix | 5.0 | 50.0 | 75.0 |
| Molecular Grade $H_2O$ | 8.74 | 87.4 | 131.1 |
| Total Master Mix Volume | 15.0 | 150.0 | 225.0 |

Figure 7A:
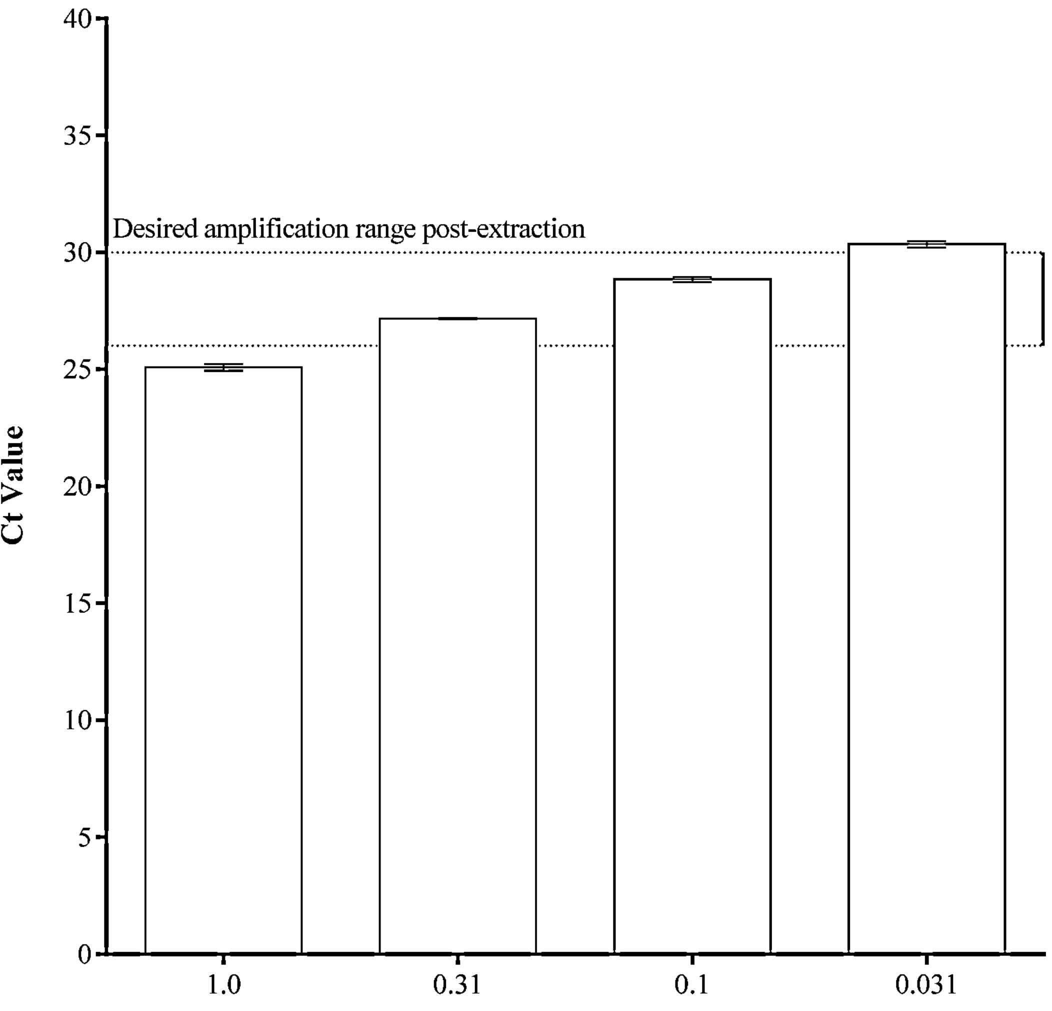
FIGS. 7A and 7B are graphs showing effectiveness of total human RNA control as a non-viral extraction control (NVC). Human total RNA control (50 ng/μl) was purchased from Applied Biosystems (Cat #4307281, Foster City, CA). Total control RNA was diluted to a starting concentration of 1.0 ng/μl in 10 mM Tris and serial diluted in a final volume of 1 ml at 0.5 log increments in Tris (pH 8.0) from 1.0 ng/μl to 0.0316 ng/μl. A total of 200 μl of each dilution was extracted in triplicate using ReX reagents on the KingFisher extraction platform and analyzed by RT-PCR on a QuantStudio 12K Flex real-time instrument using 5 μl of elution in a total reaction volume of 20 μl. A predefined amplification range for RNase P was established at 28±2 cycles (grey zone in FIGS. 7A and 7B) and concentrations of RNase P which fell within range following 20 μl extraction are depicted in FIG. 7A. Stability of the NVC was established over time (FIG. 7B) when stored at 2-8° C. from 1 to 24 hours. The 0-hour represents the time at which a fresh NVC was prepared and the total change of n=3 replicates were tested and compared against the 0-hour timepoint. All graphed data in FIGS. 7A and 7B represent the mean±sem of n=3 replicates.

Analysis of extracted NVC by RT-PCR revealed an optimal concentration of total human control RNA for use as a non-viral extraction control between 0.31 ng/μl and 0.1 ng/μl (FIG. 7A). Specifically, a 200 μl extraction at 0.31 ng/μl total human control RNA amplified RNase P at 27.17±0.01 cycles and 200 μl extraction at 0.1 ng/μl amplified RNase P at 28.84±0.11 cycles (FIG. 7A). A 200 μl extraction at 0.031 ng/μl was too dilute to amplify RNase P within the pre-established range (Cq=30.35±0.14; FIG. 7A) and 200 μl extraction at 1.0 ng/μl was 10-fold more concentrated than required (Cq=25.09±0.15; FIG. 7A). However, since extraction at 1.0 ng/μl is at 10×concentration, these data also indicate that a 1.0 ng/μl stock of total human control RNA could be generated and stored in aliquots to preserve RNA integrity until such time to prepare a 0.1 ng/μl NVC 1× working stock (FIG. 7A).

Figure 7B:
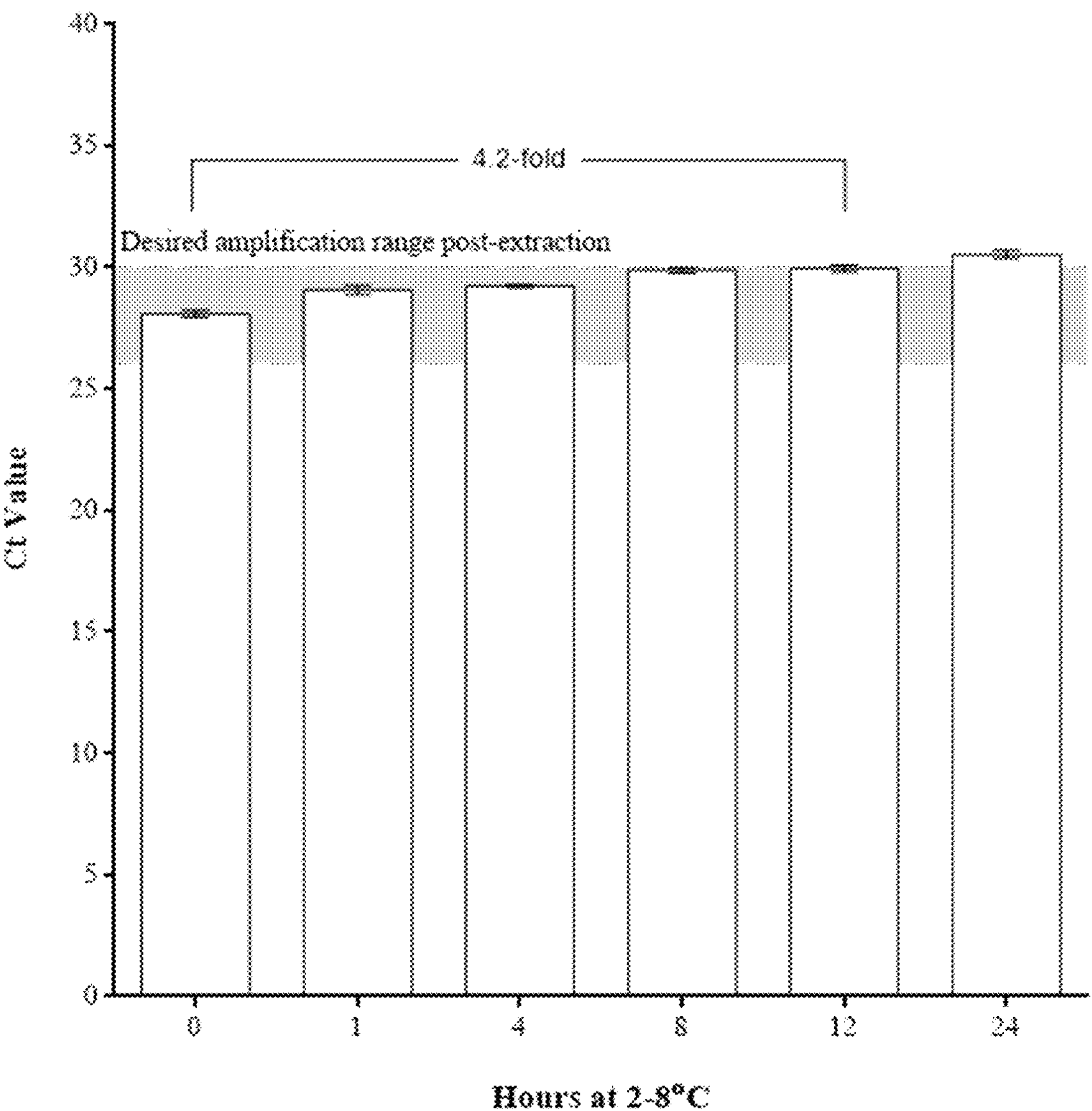

A 200 μl extraction at 0.1 ng/μl was sufficient to amplify RNase P within the desired 28±2 cycle range (FIG. 7A). Therefore, we chose this concentration as it increased the number of non-viral controls (NVC) capable of being generated from a 50 ng/μl commercial stock. Therefore, a test was conducted to determine the stability of a 1×working NVC stock over time when stored at 2-8° C. To this end, 5 ml of 0.1 ng/μl total human control RNA was prepared in 10 mM Tris (pH 8.0) and distributed into n=18, 200 μl aliquots. Three (n=3) aliquots were immediately frozen at <−70° C. and were identified as time zero (To) to establish the baseline amplification of RNase P in the NVC preparation. The remaining n=15 aliquots were stored at 2-8° C. At 1, 4, 8, 12, and 24 hours post preparation, n=3 aliquots were frozen at <−70° C. Twenty-four hours (24 hrs) after the last sample was frozen, all aliquots were thawed, extracted together using ReX reagents on the KingFisher Flex extraction platform, and analyzed simultaneously by RT-PCR using the PCR reaction mix outlined in Table 4. As expected, analysis of the extracted n=3, To samples of 0.1 ng/μl generated amplification of RNase P at 28.08±0.15 cycles (FIG. 7B) and demonstrated no loss in amplification relative to fresh preparation and extraction (FIG. 7B). When stored at 2-8° C., no significant depreciation in amplification was observed at 1 or 4 hours (29.14±0.12; FIG. 7B) and only a 4-fold decrease in RNase P amplification was observed in NVC stored for 8 hours at 2-8° C. prior to extraction (Cq=29.22±0.05; FIG. 7B) and at 12 hours at 2-8° C. (Cq=29.94±0.14; FIG. 7B). Non-viral control stored for 24 hours at 2-8° C. followed by extraction demonstrated amplification of RNase P at 30.53±0.17 cycles representing a >6-fold loss of RNA integrity and fell outside the predefined acceptable range of amplification at 28±2 cycles. Therefore, these data indicate that non-viral control at a concentration of 0.1 ng/μl is stable for up to 12 hours at 2-8° C. (FIG. 7B).

TABLE 4

| RNase P RT-PCR Reaction Mix | | | |
|---|---|---|---|
| Description | 1x (μl) | 10x (μl) | 15x (μl) |
| RNase P Fwd (9 μM) | 0.54 | 5.4 | 8.1 |
| RNase P Rvs (9 μM) | 0.54 | 5.4 | 8.1 |
| RNase P Probe (3 μM) | 0.18 | 1.8 | 2.7 |
| 4X Fast Virus Enzyme Mix | 5.0 | 50.0 | 75.0 |
| Molecular Grade $H_2O$ | 8.74 | 87.4 | 131.1 |
| Total Master Mix Volume | 15.0 | 150.0 | 225.0 |

The Reditus FluV19 Probe Design is Equivalent to the CDC FLuSC2 Probe Design.

Figure 3:
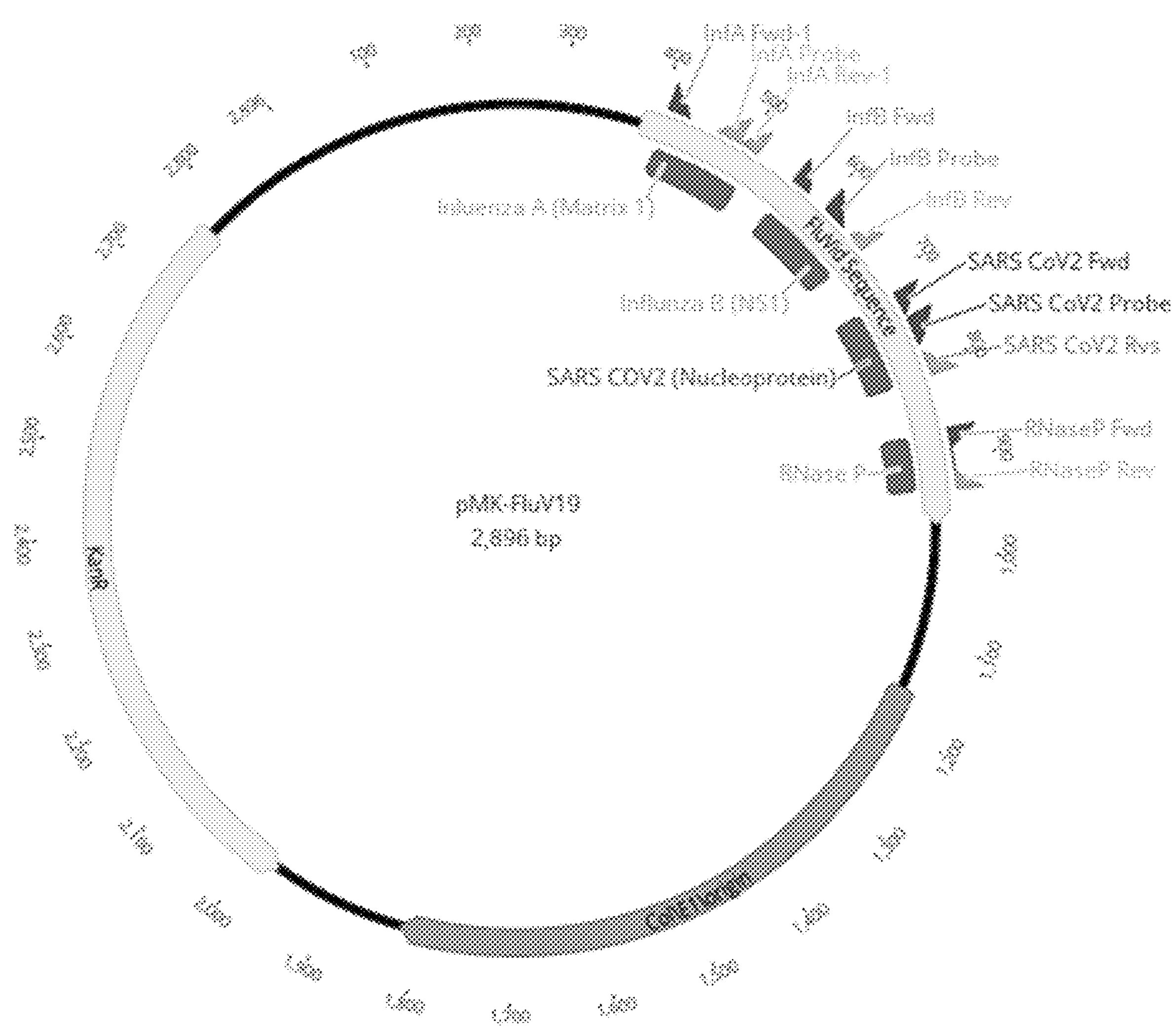
FIG. 3 is an annotated construct map for the pMK-FluV19 control plasmid.

In addition to development of a non-viral extraction control which tests the reverse transcriptase enzyme activity for RT-PCR, a positive template control (PTC) is needed for PCR which verifies the activity of each primer and probe used for analyte detection as well as the activity of the polymerase during PCR amplification (42 CFR 493.1256). Thus, to expand testing capabilities to include testing for Influenza A and Influenza B, we developed a plasmid containing viral sequence regions targeted by each of the CDC's primer and probe sets and which also contains the targeted gene sequence for the p30 subunit of the Human RNase P gene (FIG. 3; Materials and Methods). We favored the development of this control approach as current positive controls for the CDC FLuSC2 (Prevention, 2021) and other similar assays which test for Influenza A/B/SARS-2 utilize RNA as the positive template control for PCR (Scientific, 2021). These positive control strategies have demonstrated instability and inconsistencies leading to unnecessary repeat testing and are cumbersome in technical preparation for laboratorians as they require several dilution steps needed to generate the final control (Scientific, 2020, 2021; Prevention, 2021). In contrast, the use of a plasmid control approach allows for large-scale production of control template which is stable at multiple temperature ranges (2-8° C., −15±5° C., <−70° C.) for extended periods of time with no loss in amplification efficiency due to degradation (Brunet et al., 2017; Driessen et al., 2017). Additionally, bacteria transformed with control plasmid offers an endless supply of reagent and more than 1-million reactions of PTC can be generated with a single miniprep of plasmid in 50 μl elution. Lastly, plasmid control concentrations can be quantified by spectrophotometry and diluted to a defined range for both reproducibility and to also provide a relative copy number of genome equivalents for each gene target. Thus, the use of a plasmid control could be used for semi-quantitative PCR to identify the relative viral load within a patient specimen for each of the analytes tested.

To make the current CDC FluSC2 probe sets (Prevention, 2021) more-robust as a multiplex assay for use on real-time instruments, we modified the fluorophore and quencher combinations for use with the Fast Virus 1-Step Master Mix which contains ROX as a passive reference (SEQ ID NOs: 15-18; Table 5) to reduce background noise associated with numerous assays lacking a passive reference in their PCR reaction mix. To validate our new probe/quencher combinations, we simultaneously tested our multiplex assay against the CDC FluSC2 assay using dilutions of our purified, linearized pMK-FluV19 control to determine the relative limit of detection and amplification efficiency of each of the assays. Specifically, 41 ng/μl of pMK-FluV19 was diluted serially in 0.5 log increments to a final dilution of $10^{-9}$ dilution with a terminal estimated genome equivalent $1.4 \times 10^0$ copies of influenza A, influenza B, SARS-CoV-2, and RNase P and 5 µl of each dilution was tested in triplicate by PCR using the CDC's reaction formulation (Prevention, 2021) and by the FluV19 reaction mix listed in Table 5. Data were analyzed using Applied Biosystems Design & Analysis software for each PCR reaction and the mean±sem of each dilution, by analyte, was calculated and graphed using GraphPad Prism software (FIG. 8).

TABLE 5

Reditus FluV19 Multiplex RT-PCR Reaction Mix

| Description | 1x (µl) | 10x (µl) | 100x (µl) |
|---|---|---|---|
| Component B (combined primer mix) | 2.4 | 24 | 240 |
| Component C (combined probe mix) | 2.4 | 24 | 240 |
| 4X Fast Virus Enzyme Mix | 5.0 | 50 | 500 |
| Molecular Grade $H_2O$ | 5.2 | 52 | 520 |
| Total Master Mix Volume | 15.0 | 150 | 1,500 |

Figures 8A, 8B:
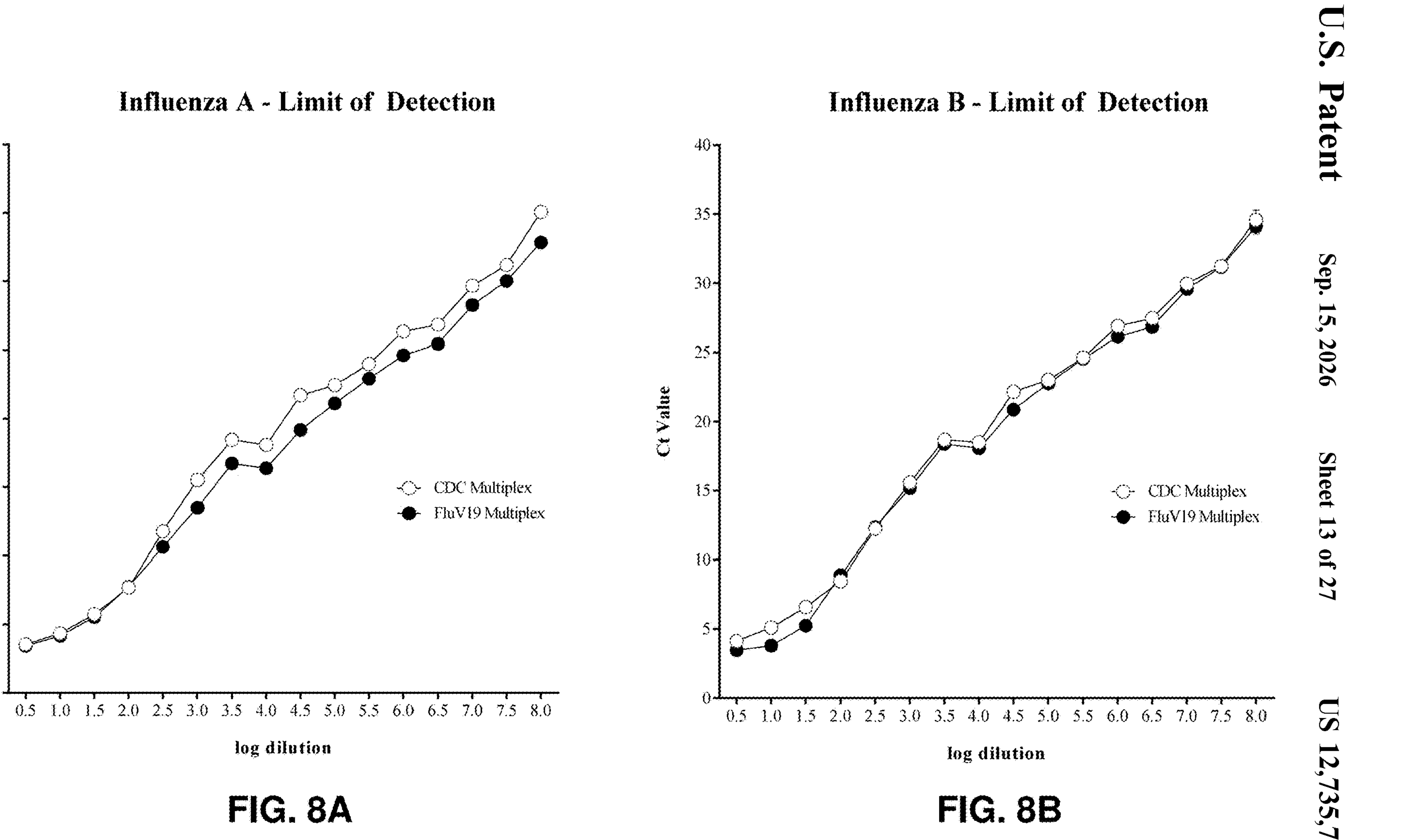
FIGS. 8A, 8B, 8C and 8D are graphs showing the Reditus FluV19 assay is equivalent to the EUA-CDC FLuSC2 assay. Linearized pMK-FluV19 plasmid were diluted in 0.5 log increments using 10 mM Tris (pH 8.0) as the diluent. 5 μl of total input was analyzed by PCR using either the FluV19 PCR reaction mix depicted in Table 4 or in accordance with the EUA CDC-FLuSC2 method. Each dilution was tested in triplicate and the mean±sem of each dilution is presented in for each gene target (FIG. 8A., Influenza A.
Figures 8C, 8D:
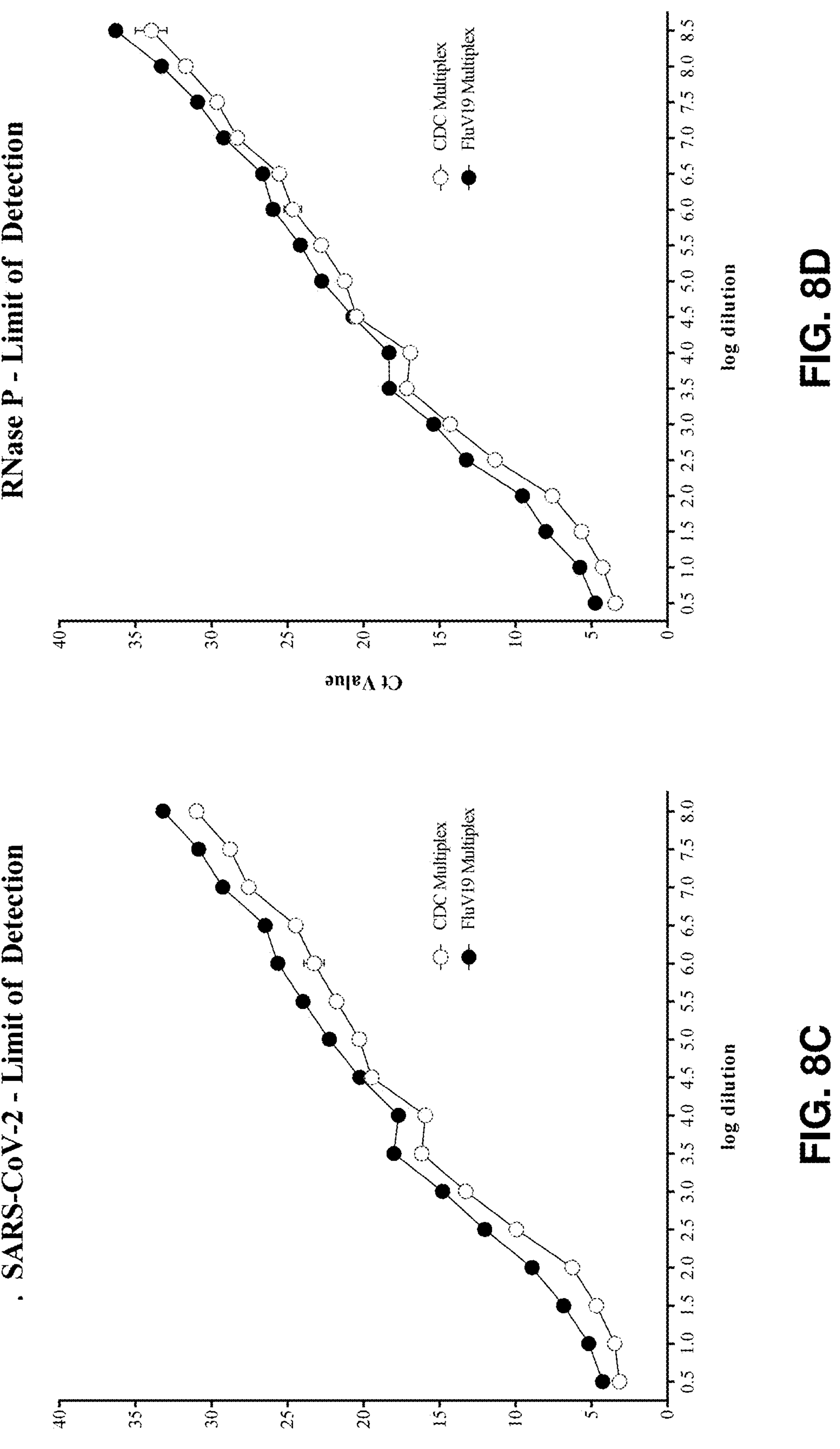

Analysis of data indicated that both the CDC PCR formulation and the modified Reditus PCR formulation demonstrated equivalent detection of all viral- and control gene-targets (FIGS. 8A, 8B, 8C and 8D). Specifically, both the CDC FLuSC2 and Reditus FluV19 assays were able to detect equivalent N-, S-, and ORF1ab-gene copies at $10^{-8}$ dilution of linearized plasmid representing an estimated limit of detection at ~130 genome copy equivalents (FIGS. 8A, 8B and 8C). Likewise, detection of RNase P using linearized plasmid was also equivalent between test methods with terminal detection at $10^{-8.5}$ dilution representing ~42 gene copy equivalents (FIG. 8D). Interestingly, when a similar experiment was performed using dilutions of circularized pMK-FluV19, both assays detected Influenza A and Influenza B targets at equivalent genome equivalents of ~130 copies; however, detection of SARS-CoV-2 N-gene increased an additional 5-fold with an overall limit of detection of ~20 genome copy equivalents (data not shown). The decrease in detection using linearized pDNA may have resulted from restriction enzyme star activity within the pMK-FluV19 SARS-CoV-2 sequence. Thus, the estimated limit of detection for each analyte is ~130 genome equivalents for influenza A and influenza B, ~60 genome equivalents for SARS-CoV-2, and ~42 gene equivalents for RNase P. In short, neither the modifications in fluorophore/quencher combinations or the change in Master Mix formulation of the Reditus FluV19 assay reduced detection relative to the EUA-approved CDC FLuSC2 assay.

Analysis of the Complete Fluv19 Assay Performs Equivalent to the CDC FluSC2 Assay and Better than the Commercial Thermo Fisher TaqMan COVID-19 Flu A/B Assay.

The accumulation of data thus far indicate that Reditus extraction reagents (ReX) are equivalent to Thermo MagMax™ MVP II extraction of clinical samples on the KingFisher Flex extraction platform (FIG. 5) but demonstrate less variability than MagMax™ extractions over time (FIG. 6). Additionally, we demonstrate the 0.1 ng/µl of total human genomic RNA control is stable for 12 hours at 2-8° C. and can be used successfully as a non-viral (NVC) control reagent to test for reverse transcriptase activity during RT-PCR following extraction (FIG. 7). Lastly, we confirmed that the combination of modified CDC probe sequences for influenza A, influenza B, and SARS-CoV-2 and Fast Virus Enzyme containing ROX performs equivalently to the EUA-approved CDC primer and probe set in detecting the same genome copy equivalents of influenza A, influenza B, SARS-CoV-2, and RNase P (FIG. 8). We next sought to test the combined Reditus FluV19 assay using ReX extraction reagents and FluV19 RT-PCR multiplex using a 200 µl of clinical samples containing influenza A, influenza B, SARS-CoV-2, and combinations thereof, to detect both individual and co-infections. To fully vet the FluV19 assay, we also tested the same samples extracted using 200 µl of specimen with MagMax™ MVPII and tested either using the CDC FLuSC2 assay (Prevention, 2021) or using the TaqMan COVID-19 FluA, FluB Multiplex Assay (Cat #A47701, Thermo Fisher, Waltham, MA, Scientific, 2021).

Figure 9A:
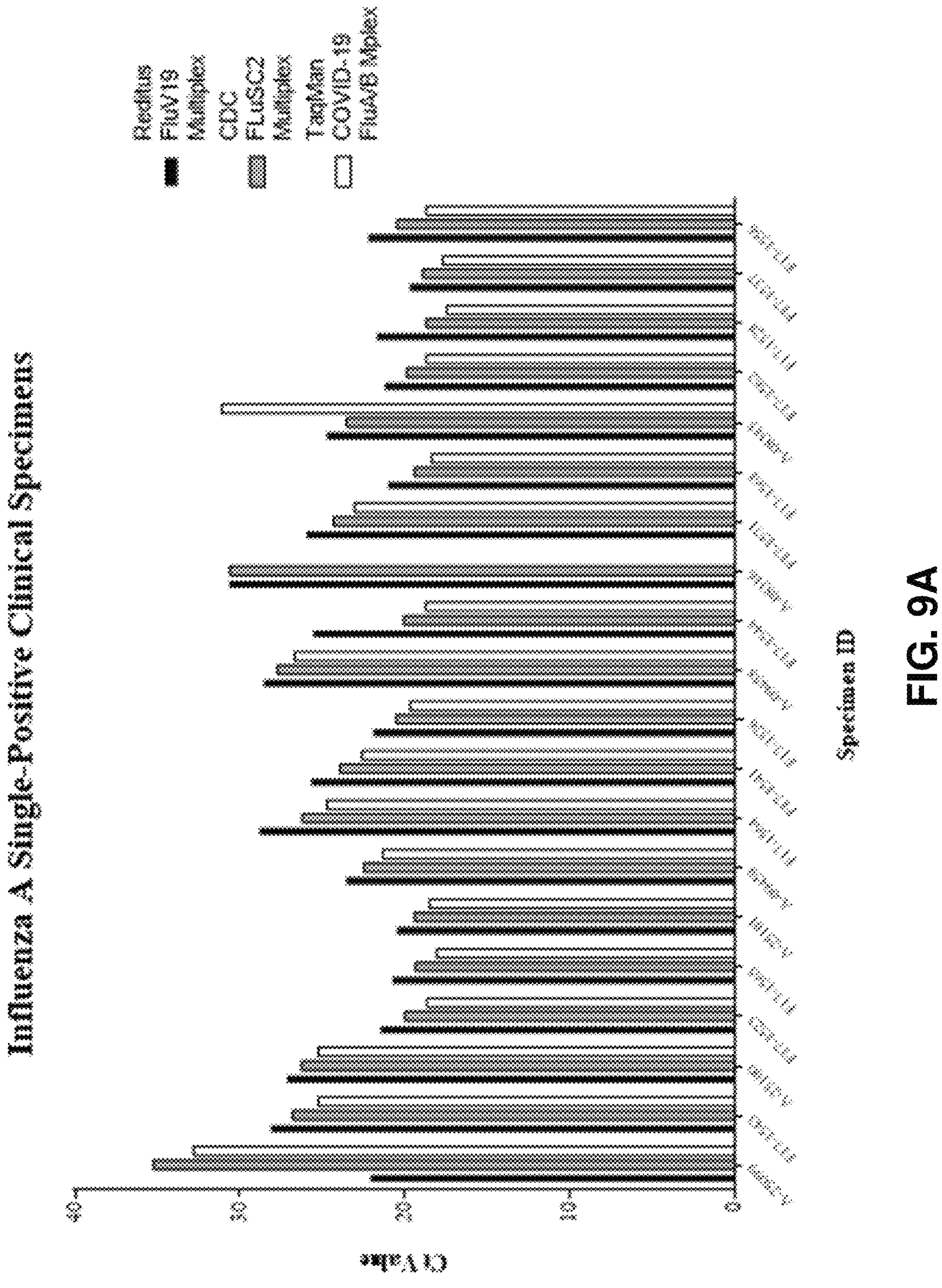
FIGS. 9A, 9B and 9C are graphs showing results of single-positive clinical samples tested by ReX FluV19, CDC-FLuSC2, and Thermo Fisher TaqMan COVID-19 FluA/B Multiplex RT-PCR Assays. Single-positive clinical specimens were extracted using either Reditus extraction reagents (ReX) or MagMax reagents. Nucleic acid extracted from specimens using ReX reagents were amplified using the FluV19 assay reaction mixture specified in Table 4. Nucleic acid from specimens extracted using MagMax reagents were amplified using either the CDC-FLuSC2 assay or Thermo TaqPath COVID-19 FluA/B RT-PCR reagents according to each manufacturer's requirements.
Figure 9B:
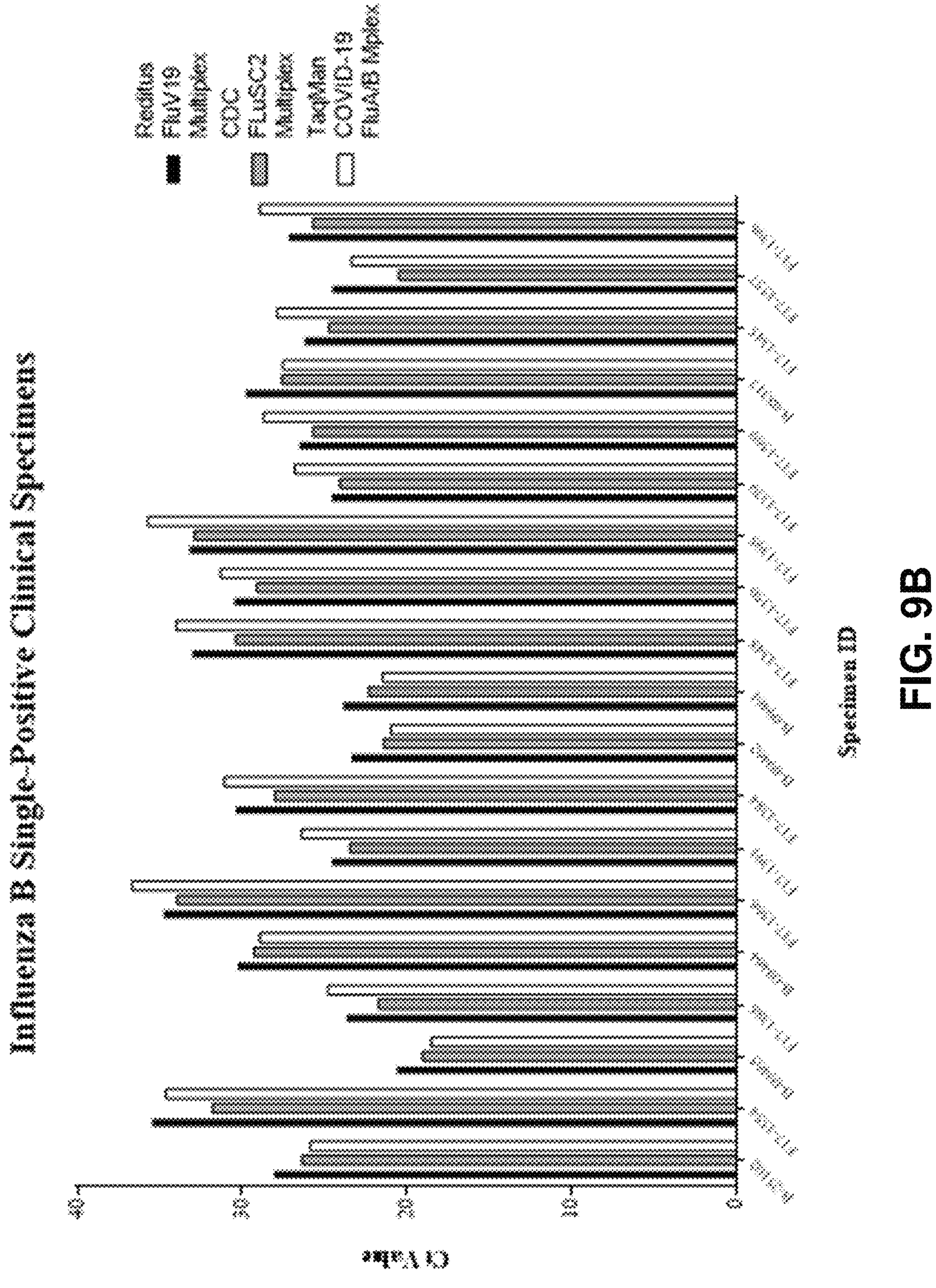
Figure 9C:
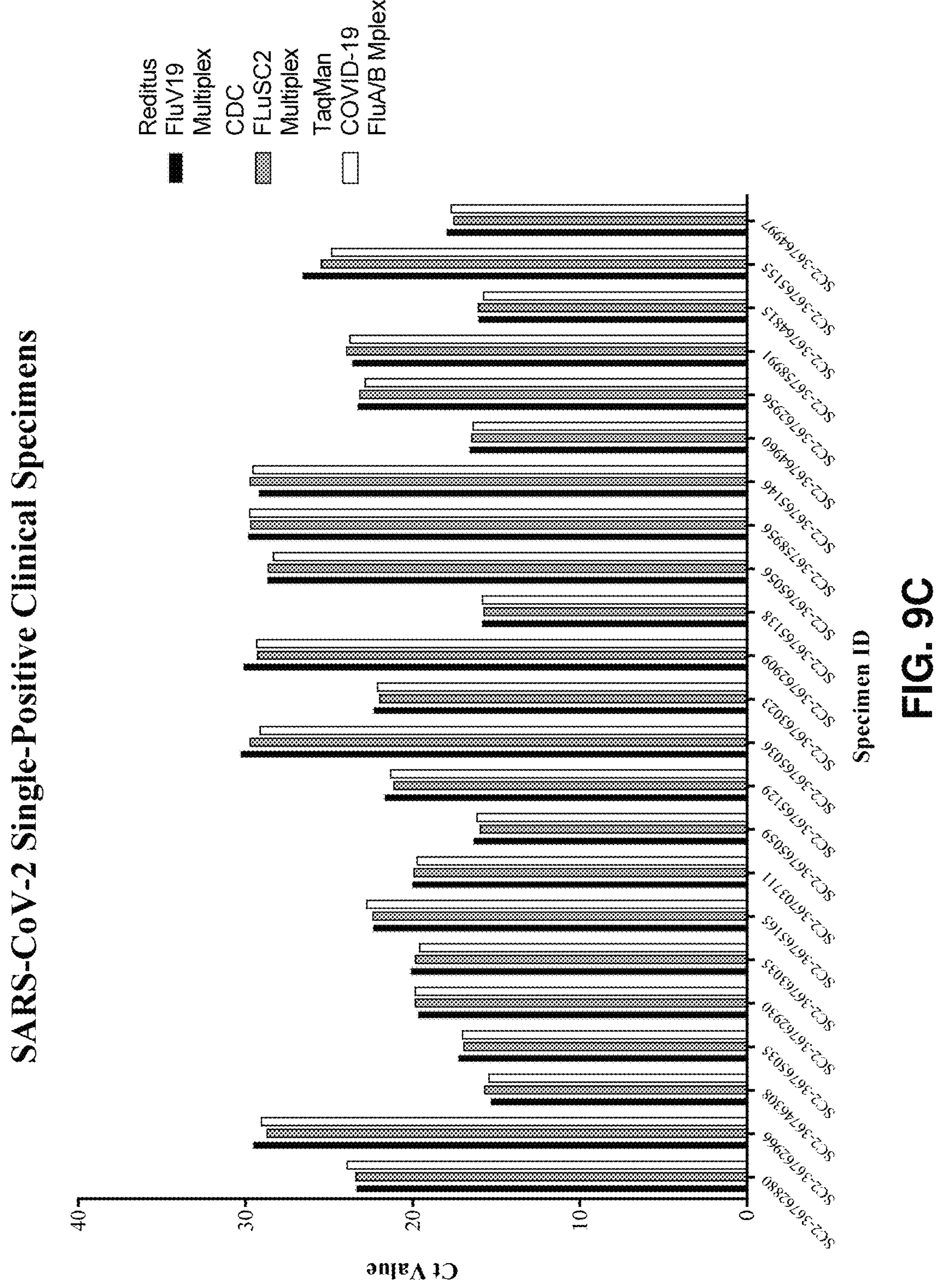

Analysis of PCR results demonstrated equivalence in detection of Influenza A single-positive clinical specimens extracted and tested with either the CDC FLuSC2 RT-PCR assay or the Reditus FluV19 assay (FIG. 9A). The same clinical sample was not-detected by either the FLuSC2 or the FluV19 assay but was detected with the TaqMan COVID-19 FluA, FluB Multiplex Assay, albeit at a Cq value higher than the 38 cycle cut-off used for the FLuSC2 and FluV19 assays. A separate clinical sample (A-08316; FIG. 9A) was undetected by the Thermo TaqMan assay but was detected at equivalent cycles (Cq=37) by both FLuSC2 and FluV19 assays (FIG. 9A). In contrast, the Thermo TaqMan COVID-19 FluA/B produced n=5 false-positive results which were discordant to both the FLuSC2 and FluV19 assays and the expected results provided by IDPH-Springfield and NorthShore University HealthSystem. The high false-positive detection of Influenza A is likely due to differences in primer and probe sets of the Thermo TaqMan assay, but this cannot be confirmed as the targets of their sequences are proprietary. Analysis of single-positive Influenza B specimens indicated that all appropriate specimens were detected regardless of assay (FIG. 6B). Likewise, analysis of all single-positive SARS-CoV-2 clinical specimens were equivalently detected across each extraction method and RT-PCR assay (FIG. 9C).

Figure 10A:
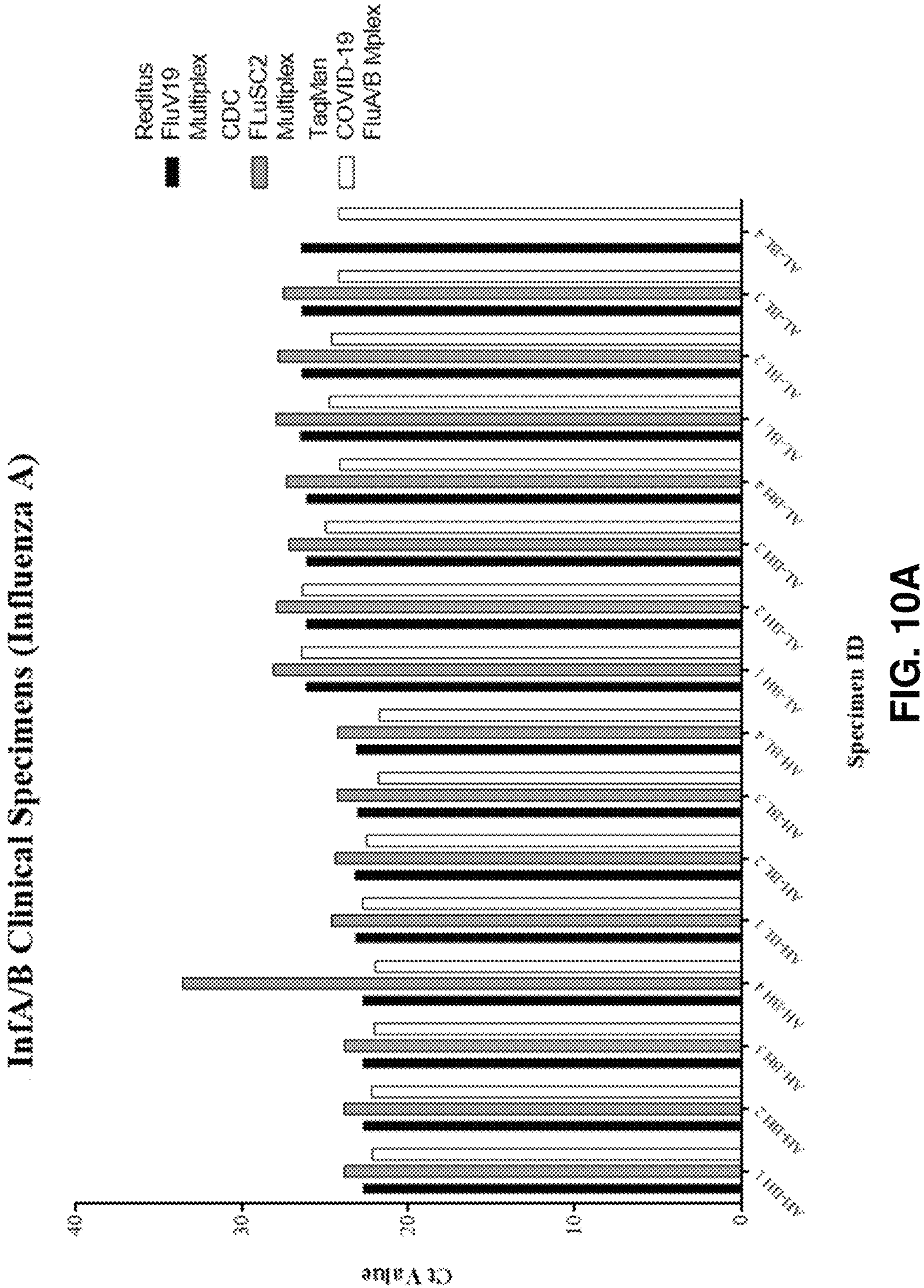
FIGS. 10A and 10B are graphs showing results of influenza A and influenza B double-positive clinical samples tested by ReX FluV19, CDC-FLuSC2, and Thermo Fisher TaqMan COVID-19 FluA/B Multiplex RT-PCR assays. Influenza A and influenza B clinical specimens were combined to generate specimens representing dual infections at high (H) and low (L) concentrations. Each specimen was extracted using either Reditus extraction reagents (ReX) or MagMax reagents. Nucleic acid extracted from specimens using ReX reagents were amplified using the FluV19 assay reaction mixture specified in Table 4. Nucleic acid from specimens extracted using MagMax reagents were amplified using either the CDC-FLuSC2 assay or Thermo TaqPath COVID-19 FluA/B RT-PCR reagents according to each manufacturer's requirements.
Figure 10B:
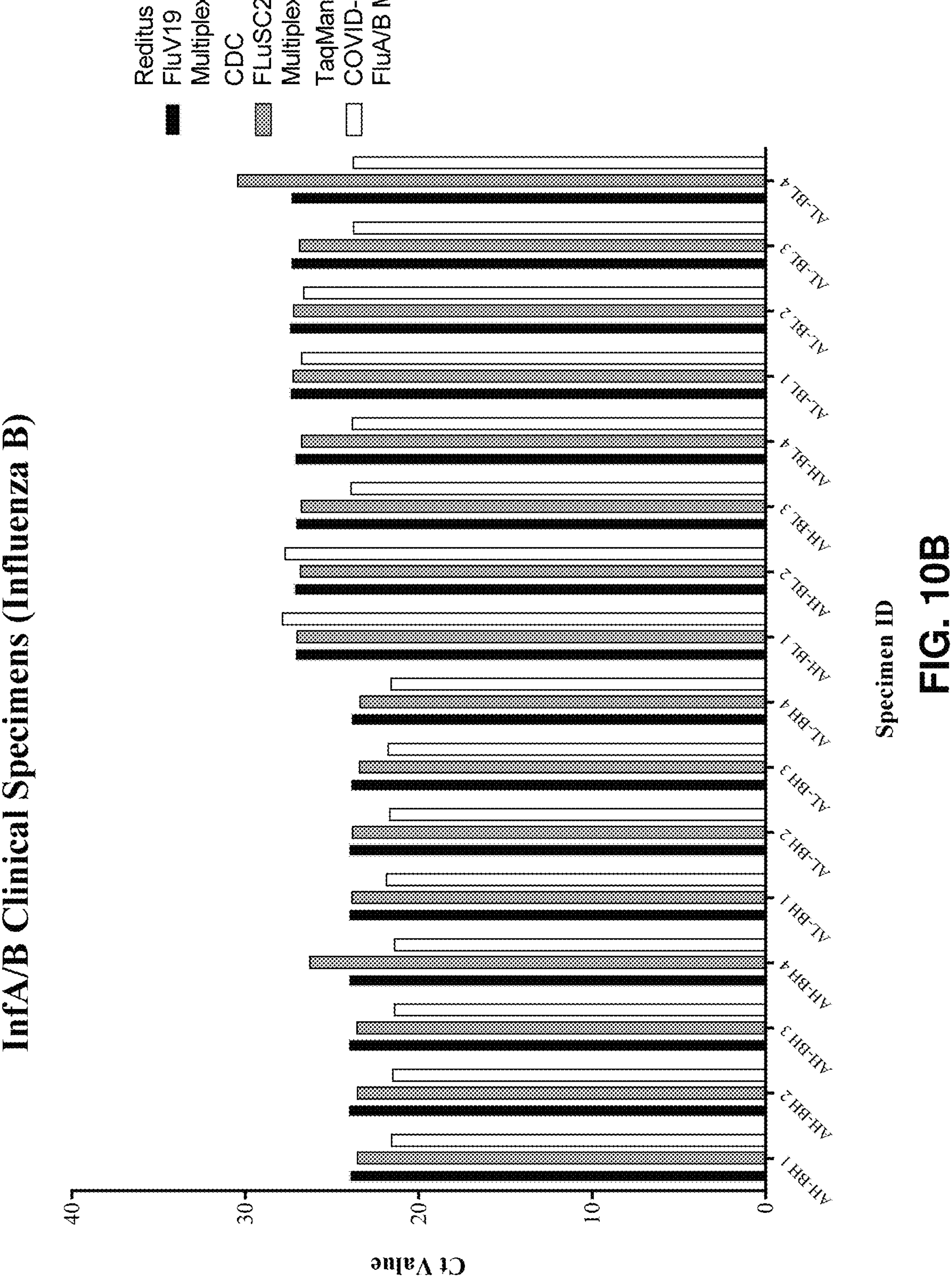
Figure 11A:
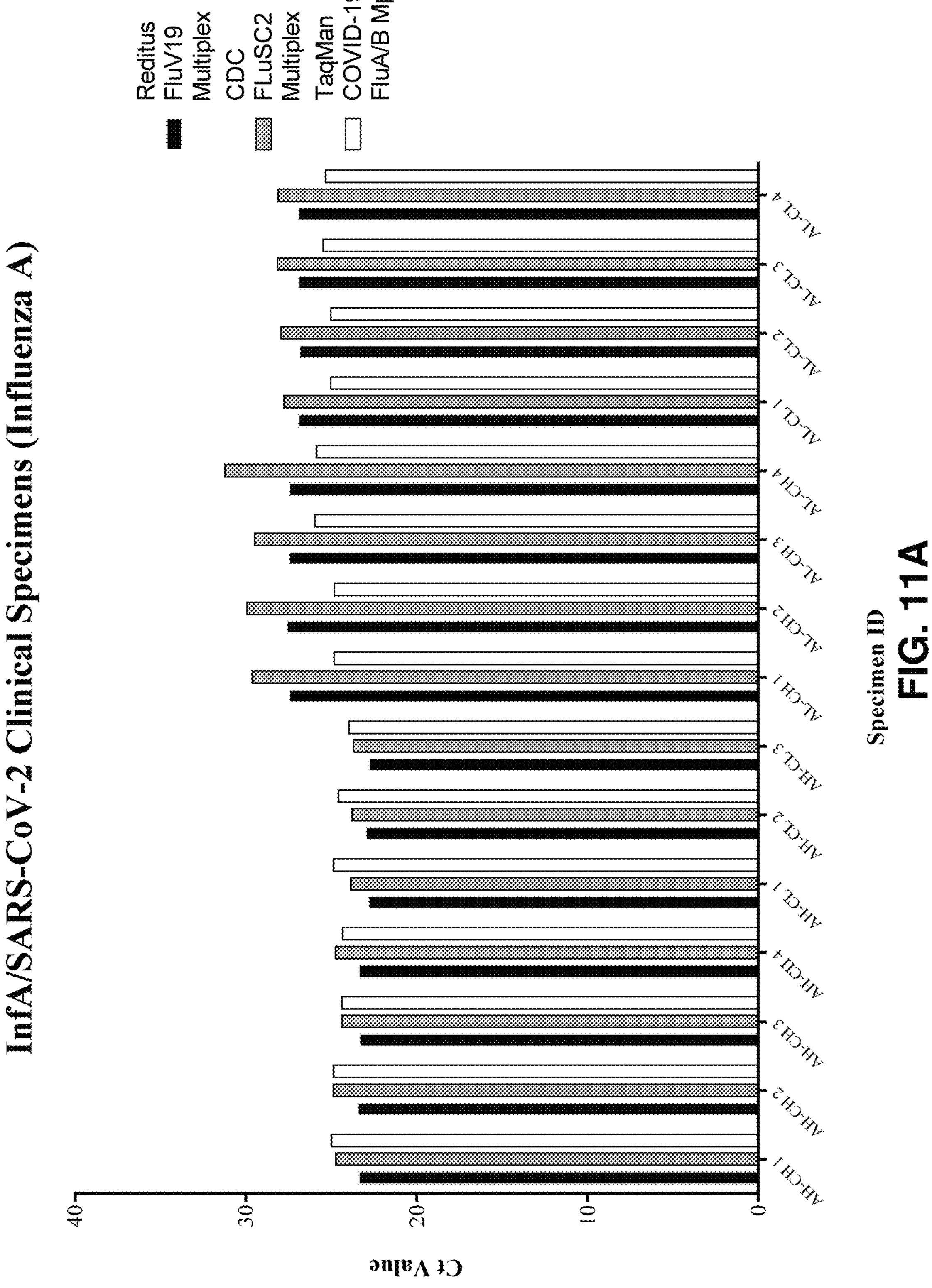
FIGS. 11A and 11B are graphs showing results of influenza A and SARS-CoV-2 double-positive clinical samples tested by ReX FluV19, CDC-FLuSC2, and Thermo Fisher TaqMan COVID-19 FluA/B Multiplex RT-PCR Assays. Influenza A and SARS-CoV-2 clinical specimens were combined to generate specimens representing dual infections at high (H) and low (L) concentrations. Each specimen was extracted using either Reditus extraction reagents (ReX) or MagMax reagents. Nucleic acid extracted from specimens using ReX reagents were amplified using the FluV19 assay reaction mixture specified in Table 4. Nucleic acid from specimens extracted using MagMax reagents were amplified using either the CDC-FLuSC2 assay or Thermo TaqPath COVID-19 FluA/B RT-PCR reagents according to each manufacturer's requirements.
Figure 11B:
Figure 12A:
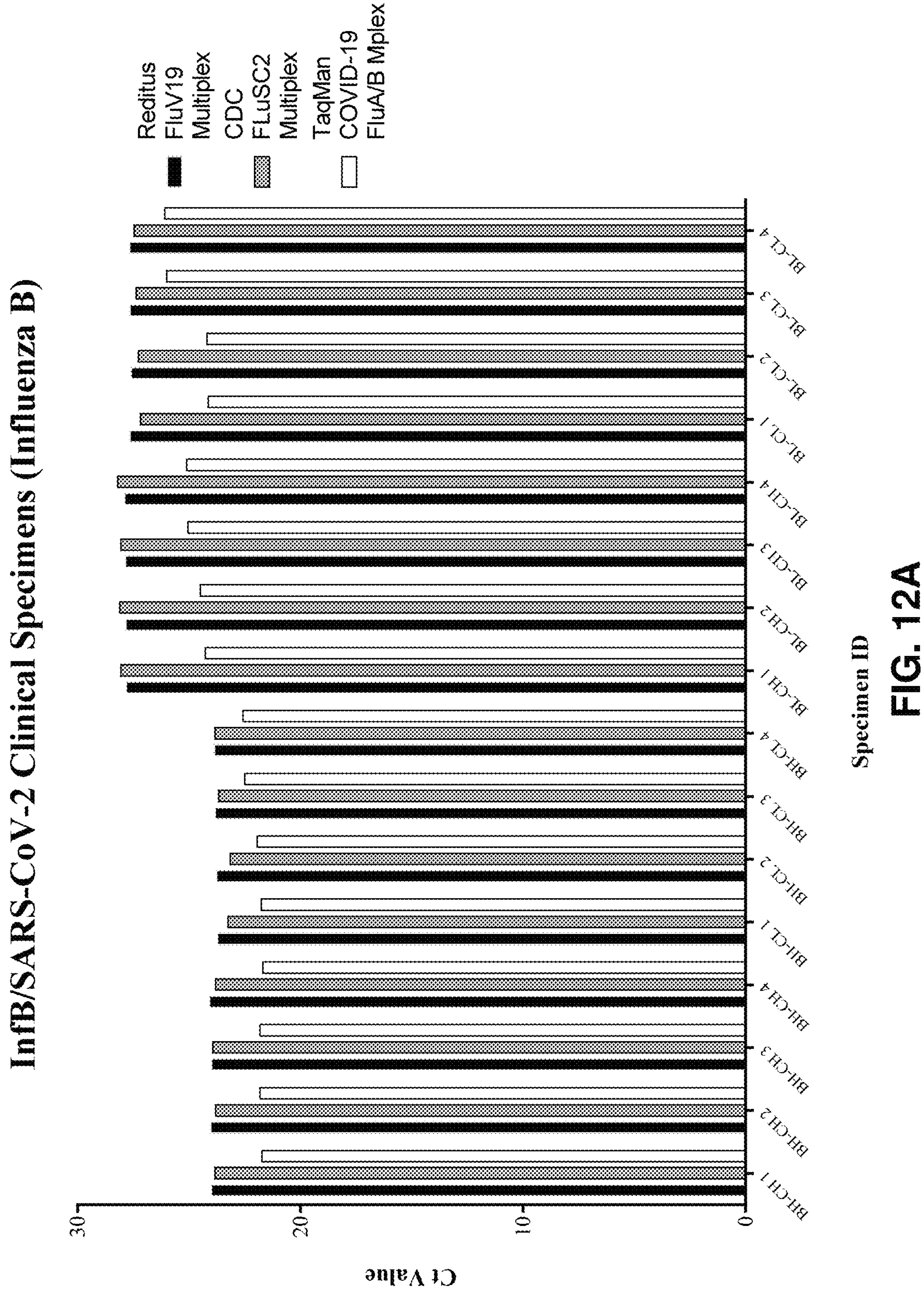
FIGS. 12A and 12B are graphs showing results of influenza B and SARS-CoV-2 double-positive clinical samples tested by ReX FluV19, CDC-FLuSC2, and Thermo Fisher TaqMan COVID-19 FluA/B Multiplex RT-PCR Assays. Influenza B and SARS-CoV-2 clinical specimens were combined to generate specimens representing dual infections at high (H) and low (L) concentrations. Each specimen was extracted using either Reditus extraction reagents (ReX) or MagMax reagents. Nucleic acid extracted from specimens using ReX reagents were amplified using the FluV19 assay reaction mixture specified in Table 4. Nucleic acid from specimens extracted using MagMax reagents were amplified using either the CDC-FLuSC2 assay or Thermo TaqPath COVID-19 FluA/B RT-PCR reagents according to each manufacturer's requirements.
Figure 12B:
Figure 13A:
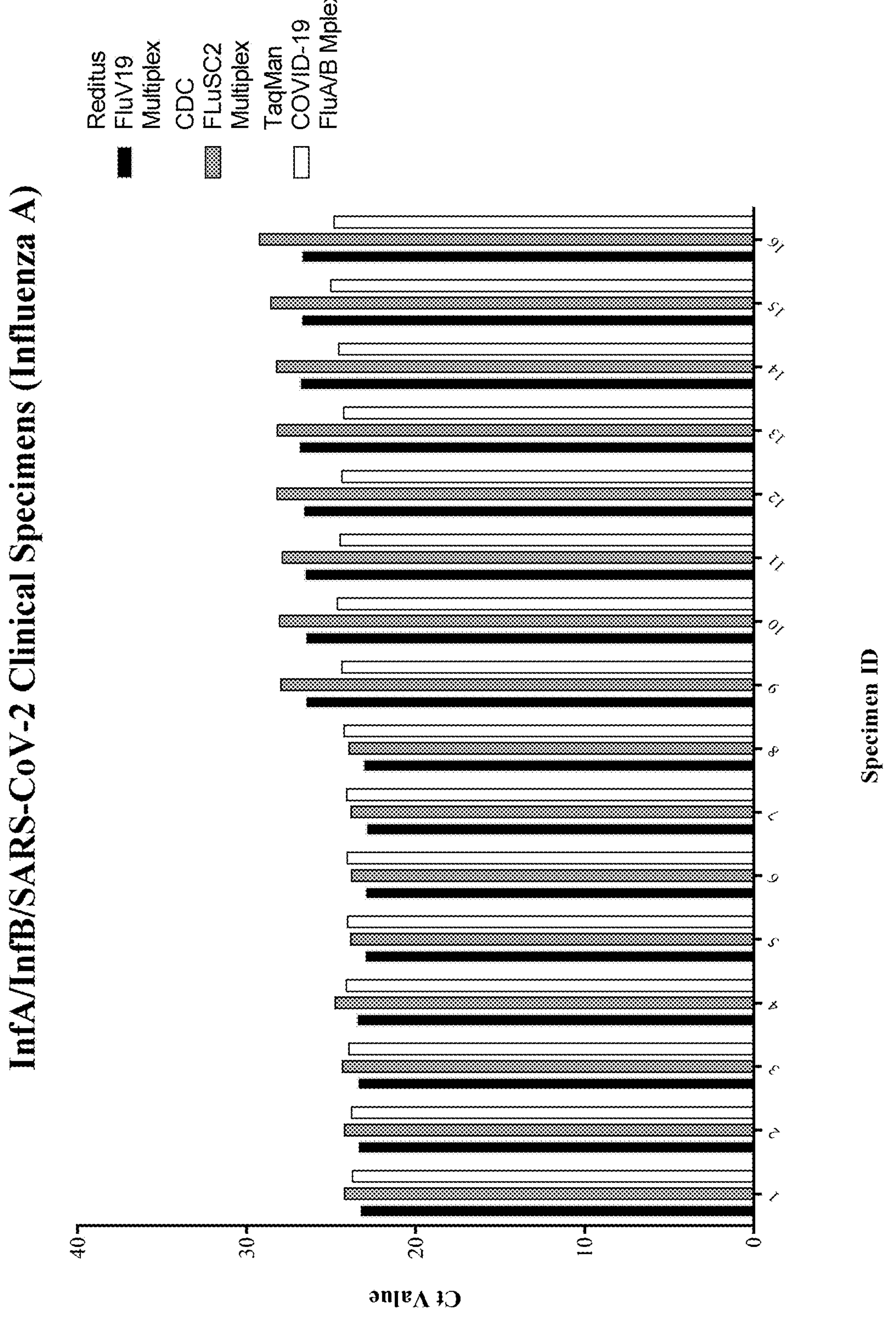
FIGS. 13A, 13B and 13C are graphs showing results of influenza A, influenza B, and SARS-CoV-2 Combined-Positive Clinical Samples Tested by ReX FluV19, CDC-FLuSC2, and Thermo Fisher TaqMan COVID-19 FluA/B Multiplex RT-PCR Assays. Influenza A, influenza B and SARS-CoV-2 clinical specimens were combined to generate specimens representing unlikely but possible triple infections at high (H) and low (L) concentrations. Each specimen was extracted using either Reditus extraction reagents (ReX) or MagMax reagents. Nucleic acid extracted from specimens using ReX reagents were amplified using the FluV19 assay reaction mixture specified in Table 4. Nucleic acid from specimens extracted using MagMax reagents were amplified using either the CDC-FLuSC2 assay or Thermo TaqPath COVID-19 FluA/B RT-PCR reagents according to each manufacturer's requirements.
Figure 13B:
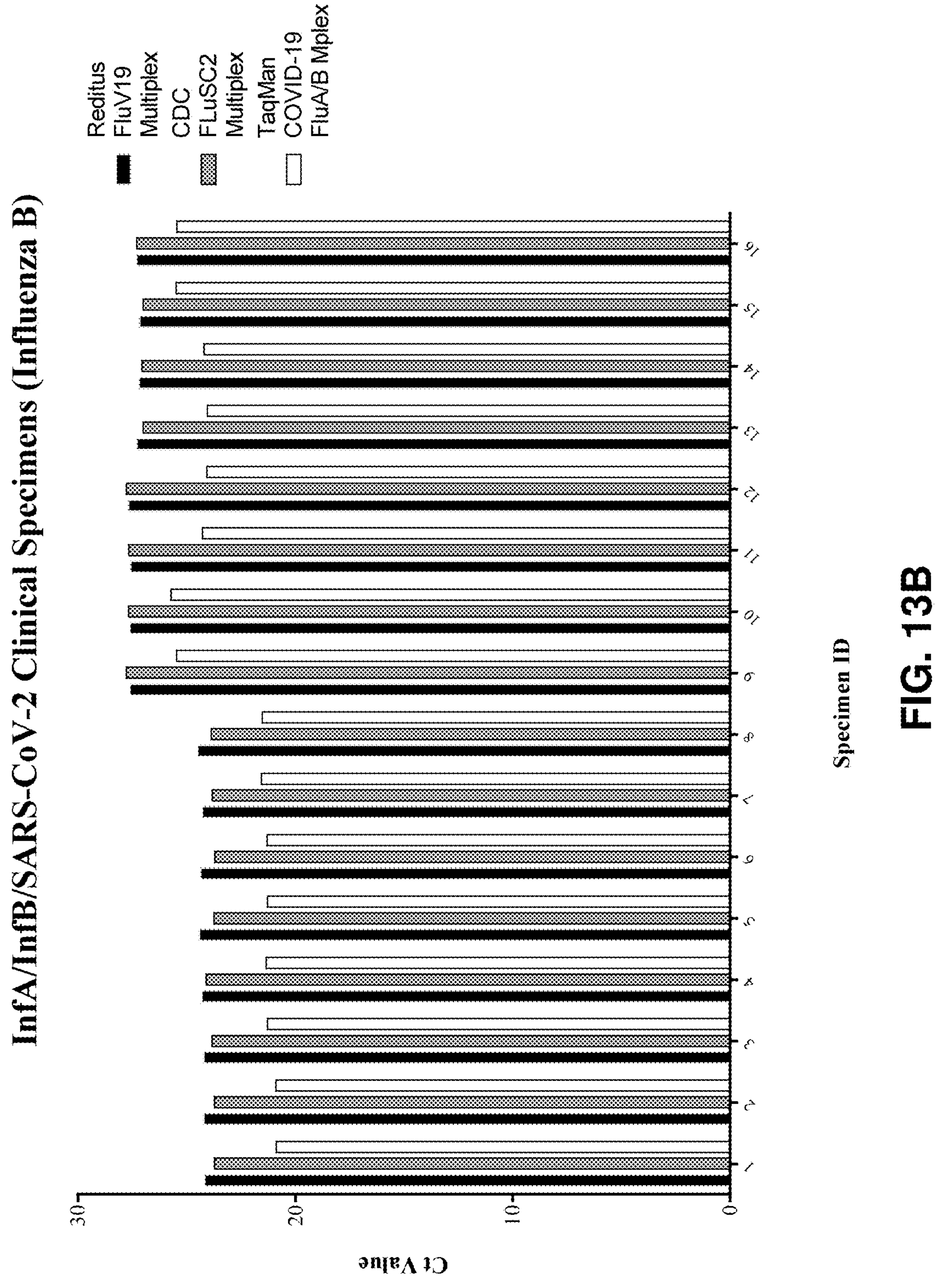
Figure 13C:
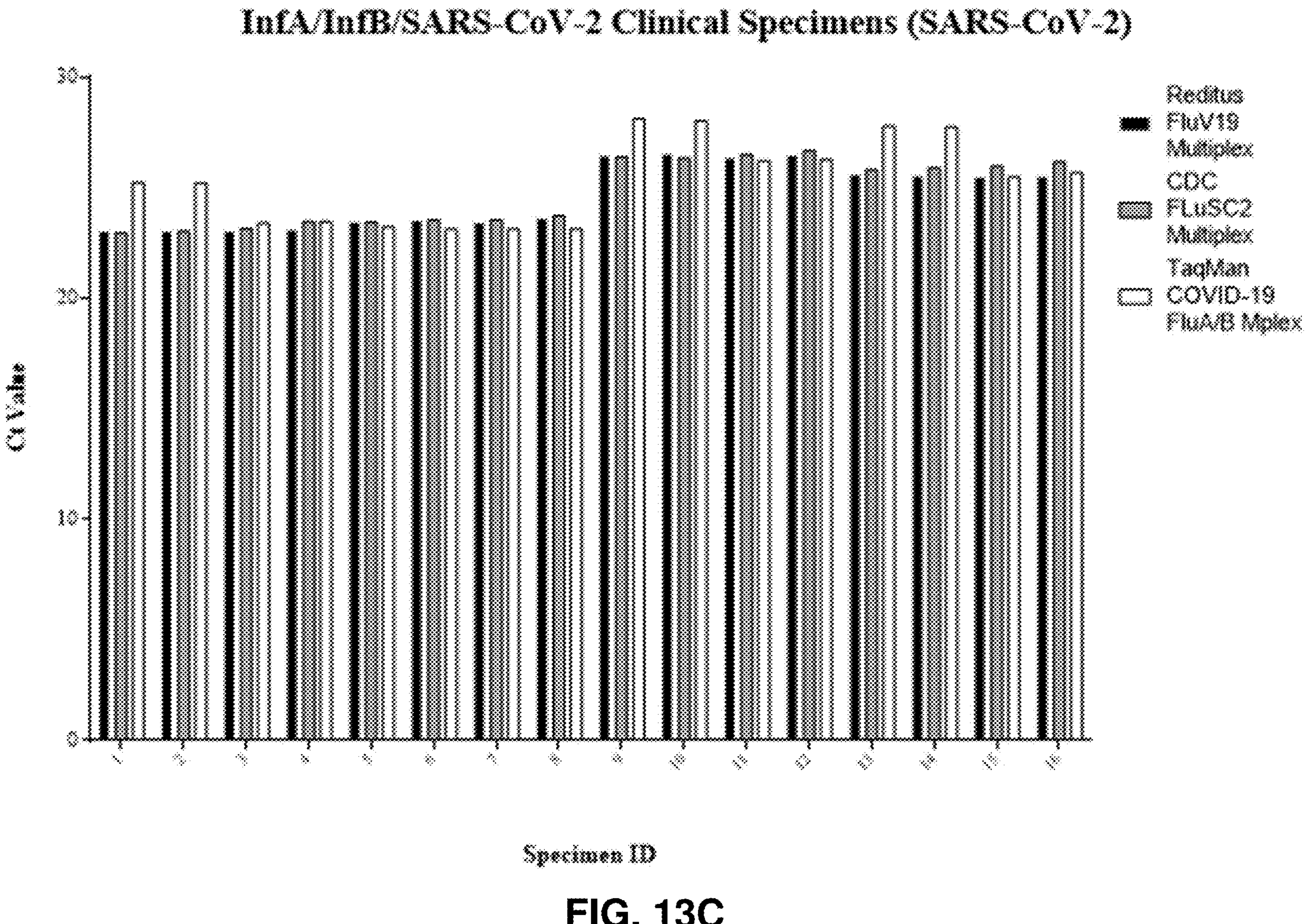

When combinations of clinical specimens were tested, the Reditus FluV19 assay was accurate in detecting 100% of all specimens for containing influenza A (n=48), influenza B (n=48), and SARS-CoV-2 (n=32), regardless of concentration (FIGS. 10A, 10B, 11A, 11B, 12A, 12B, 13A, 13B and 13C). Likewise, all influenza A-positive specimens were also detected successfully when tested with the Thermo TaqMan assay (FIG. 10A, 11A, 13A). In contrast, n=1 specimen (AL-BL-4), containing low amounts of influenza A (AL), was undetected by the CDC FLuSC2 assay (FIG. 10A). We were concerned that this might have represented a missed sample extraction leading to the false-negative result by the FLuSC2 assay. However, as anticipated, AL-BL-4 was positive for influenza B by the CDC FLuSC2 assay (FIG. 10B) and RNase P (not shown). Thus, these data indicated that the specimen AL-BL-3 was extracted with sufficient viral RNA and represented a single false-negative result for the CDC FluSC2 assay (FIG. 10A, 11A, 13A). All specimens analyzed for the detection of Influenza B were consistently detected in samples containing either high (BH) and low (BL) amounts of Influenza B, regardless of test method used (FIG. 10B, 12B, 13B). Likewise, all specimens analyzed for the detection of SARS-CoV-2 were consistently detected in samples containing either high (BH) and low (BL) amounts of SARS-CoV-2, regardless of test method used (FIG. 11B, 13B, 13C).

Neither the FluV19 or FLuSC2 assays had any false-positive influenza A detection in any negative specimens with an overall analytical sensitivity of 98.6%, 100% overall specificity and precision (Table 6). In contrast, the Thermo TaqMan COVID-19 FluA/B produced 5 influenza A false-positive results which were discordant to FLuSC2 and FluV19. This led to an overall reduction in sensitivity (98.6%), specificity (92.3%), and precision (93.2%) of the Thermo TaqMan assay to detect influenza A in clinical samples (Table 6). When the accuracy of detecting influenza A in clinical samples was calculated, the Reditus FluV19 assay was 99.2% accurate, the CDC FLuSC2 assay was 98.5% accurate, and the Thermo TaqMan assay was 95.6% accurate in detecting influenza A (Table 10). While all the extraction methods/reagents and RT-PCR assays tested met the ≥95% accuracy standard for clinical use, the Reditus FluV19 assay demonstrated the greatest sensitivity and accuracy for detecting Influenza A in clinical samples (Table 6).

TABLE 6

| Analytical Statistics | | | |
|---|---|---|---|
| | Reditus FluV19 | CDC FLuSC2 | Thermo Fisher COVID19 FluA/B |
| Influenza A | | | |
| # True Positives (a) | 69 | 69 | 69 |
| # False Positives (c) | 0 | 0 | 5 |
| # True Negatives (d) | 60 | 60 | 60 |
| # False Negatives (b) | 1 | 2 | 1 |
| Sensitivity [a/(a + b)] | 98.6% | 97.2% | 98.6% |
| Specificity [d/(c + d)] | 100.0% | 100.0% | 92.3% |
| Precision [a/(a + c)] | 100.0% | 100.0% | 93.2% |
| Accuracy [(a + d)/(a + b + c + d) | 99.2% | 98.5% | 95.6% |
| Influenza B | | | |
| # True Positives (a) | 67 | 67 | 67 |
| # False Positives (c) | 0 | 0 | 0 |
| # True Negatives (d) | 69 | 69 | 69 |
| # False Negatives (b) | 0 | 0 | 0 |
| Sensitivity [a/(a + b)] | 100.0% | 100.0% | 100.0% |
| Specificity [d/(c + d)] | 100.0% | 100.0% | 100.0% |
| Precision [a/(a + c)] | 100.0% | 100.0% | 100.0% |
| Accuracy [(a + d)/(a + b + c + d) | 100.0% | 100.0% | 100.0% |
| SARS-CoV-2 | | | |
| # True Positives (a) | 55 | 55 | 55 |
| # False Positives (c) | 0 | 0 | 1 |
| # True Negatives (d) | 69 | 69 | 69 |
| # False Negatives (b) | 0 | 0 | 0 |
| Sensitivity [a/(a + b)] | 100.0% | 100.0% | 100.0% |
| Specificity [d/(c + d)] | 100.0% | 100.0% | 98.6% |
| Precision [a/(a + c)] | 100.0% | 100.0% | 98.2% |
| Accuracy [(a + d)/(a + b + c + d) | 100.0% | 100.0% | 99.2% |

All extraction methods/reagents and RT-PCR assay tested were successful in extracting and detecting 100% of clinical samples containing Influenza B (Table 6). Therefore, the overall sensitivity, specificity, precision, and accuracy were 100% for all methods in detecting Influenza B in clinical samples (Table 6).

However, only the Reditus FluV19 and CDC FLuSC2 assays were able to accurately detect all specimens containing SARS-CoV-2 with no false-negative or false-positive results (Table 10). Thus, the overall sensitivity, specificity, precision, and accuracy was 100% for FluV19 and FLuSC2 methods to detect SARS-CoV-2 in clinical samples (Table 6). In contrast, the Thermo TaqMan assay generated n=1 false-positive result for SARS-CoV-2 in all the samples tested which resulted in a specificity and precision of 98.6% and an overall accuracy of 99.2% in detecting SARS-CoV-2 (Table 6).

The culmination of these data indicates that MagMax™ MVPII extraction on the KingFisher extraction platform coupled with detection using either the CDC FLuSC2 or Thermo COVID-19 FluA/B RT-PCR assays are sufficient in detecting ≥95% of all clinical specimens containing Influenza A, Influenza B, or SARS-CoV-2 (Table 6). However, greater sensitivity and accuracy in detecting Influenza A, Influenza B, and SARS-CoV-2 is achieved when clinical samples are extracted using Reditus extraction reagents (ReX) followed by RT-PCR analysis using the Reditus FluV19 assay (Table 6).

DISCUSSION

The FluV19 RT-PCR Assay is More Accurate in Detecting Influenza A than the CDC FluSC2 Assay and Thermo Fisher TaqMan COVID-19 FluA/B RT-PCR Assays.

Extraction using ReX reagents are equivalent to MagMax™ Viral and Pathogen Nucleic Acid Isolation Kits (FIGS. 5A-5D) and demonstrate greater reproducibility and less overall variance (FIGS. 6A-6H). In addition, the Reditus FluV19 RT-PCR assay demonstrates and equivalent limit of detection as the EUA-approved CDC FLuSC2 assay (FIGS. 8A-8D). However, the combined ReX extraction and FluV19 RT-PCR reagents are combined, the Reditus Laboratory Developed Test (LDT) demonstrates greater accuracy in Influenza A detection (99.2%) than either the CDC FLuSC2 assay (98.5%) or the Thermo COVID-19 FluA/B assays (95.6%) when extracted using MagMax™ Viral and Pathogen Nucleic Acid Isolation Kits (Table 6). Additionally, the Reditus LDT demonstrates greater accuracy (100%) in detecting SARS-CoV-2 than the TaqPath COVID-19 FluA/B assay (99.2%) (Table 6). It is likely that the decrease in extraction variability using ReX reagents contributed to an overall increase in detection using the FluV19 RT-PCR assay for Influenza A and SARS-CoV-2 (FIGS. 6A-6H).

Extraction and Amplification Controls with the FluV19 Assay are Defined and More Reproducible than Other Assays.

As stated earlier, current extraction processes using MS2 phage as an exogenous control does not offer any information with regards to clinical specimen integrity. In contrast, RNase P can be used to determine whether human cells are present within the clinical sample and thus, sample collection was performed sufficiently enough to increase the likelihood of detecting influenza A, influenza B, and/or SARS-CoV-2 in a patient. Thus, the use of defined concentrations of total human control RNA as a non-viral control (NVC) which is extracted alongside clinical specimens is an excellent method to assess extraction efficiency and reverse transcriptase activity of the RT-enzyme. Coupled with the use of the pMK-FluV19 positive template control (PTC), the combined NVC and PTC assess all aspects of extraction and PCR by assessing RT activity, polymerase activity, and the functionality of each primer and probe set contained within the PCR reaction mix. Lastly, the technical ease by laboratory testing staff is greatly enhanced using the NVC and PTC reagents as no dilutions need to be performed prior to use during extraction and/or PCR but is not the case using either the CDC-FLuSC2, Thermo TaqpPath COVID-19 (Prevention, 2021), or Thermo TaqMan COVID-19 FluA/B assays (Scientific, 2021). Thus, the Reditus FluV19 assay is not only less variable and more accurate (FIGS. 6A-6H, Table 6) but is also easier for laboratory staff to perform.

Extraction with ReX Reagents and FluV19 is More Cost-Effective than MagMax™ Extraction Reagents and Detection Using the TaqPath COVID-19 Combo Kit.

Lastly, the cost for testing each sample for SARS-CoV-2 using Thermo Fisher MagMax™ reagents is ~$3.18 per extraction and ~$15.98 for analysis using Thermo Fisher TaqPath COVID-19 RT-PCR assay for a total reaction cost of ~$19.60 per sample. In contrast, the cost to extract each clinical specimen using Reditus Extraction Reagents (ReX) is ~$0.50 and ~$4.00 using the FluV19 RT-PCR assay. Thus, the total cost savings per reaction using ReX extraction and the FluV19 RT-PCR assay is ~15.10 per reaction. For a lab performing 2,000 reactions per day, the combined savings over the MagMax and TaqPath COVID-19 Combo Kit amounts to an ~$29,000 per week. In addition to the cost savings alone, the FluV19 Combo Kit can be used to detect SARS-CoV-2, Influenza A, and Influenza B in clinical samples.

Concluding Remarks

Reditus extraction reagents (ReX) combined with the FluV19 RT-PCR assay is a robust process for detecting Influenza A, Influenza B, and SARS-CoV-2 in clinical samples while simultaneously assessing sample integrity of specimens being tested. The cost of reagents to run each specimen is significantly reduced and increases the overall detection accuracy of each viral analyte. The controls established in the FluV19 assay offer a robust method for assessing quality control of each process in the testing method, offer greater reproducibility, and less effort in preparation than other available assays. Thus, the ReX FluV19 assay is a reliable and cost-effective assay for use in clinical laboratories to detect Influenza A, Influenza B, and SARS-CoV-2 in clinical samples.

Materials and Methods

Preparation of Laboratory Reagents

1 Molar Tris (pH 8.0): 121.1 grams of Tris Base (CAS 77-86-1) was dissolved in 800 ml of distilled water ($dH_2O$). The pH of the mixture was adjusted to 8.0 using 1N HCL (CAS 7647-01-0,7732-18-5) and brought to a final volume of 1 L with $dH_2O$. The completed 1M Tris solution was sterilized by 0.22 μm filtration.

0.5 Molar EDTA (pH 8.0): 186.1 grams of Ethylenediaminetetraacetic acid (EDTA; CAS 60-00-4) was fully dissolved in 800 ml of $dH_2O$. The pH of the solution was adjusted to 8.0 using freshly prepared 5M Sodium Hydroxide (NaOH; 1310-73-2,497-19-8) and brought to a final volume of 1 L with $dH_2O$. The completed 0.5 M EDTA solution was sterilized by autoclaving for 15-minutes at 121° C.

0.5 Molar Urea: 30 grams of Urea (CAS 57-13-6) was dissolved in 800 ml of $dH_2O$ and brought to a final volume of 1 L with $dH_2O$. The completed 0.5M Urea solution was sterilized by 0.22 μm filtration.

0.5% Bromophenol Blue: 5 grams of Bromophenol Blue (CAS 115-39-9) was suspended in 800 ml of $dH_2O$ until homogenous. The mixture was brought to a final volume of 1 L with $dH_2O$.

Preparation of the ReX Lysis Buffer (ReX-LB)

200 ml of $dH_2O$ was pre-heated to 67±3° C. on a heating stir-plate with stir bar, and the following Prepared Laboratory Reagents were added in sequential order: i. 50 ml of 1M Tris (pH 8.0), ii. 50 ml of 0.5M EDTA (pH 8.0), iii. 20 ml of 0.5M Urea, and iv. 20 ml of 0.5% Bromophenol Blue. To the mixture, 30 ml of Triton X-100 (CAS 9002-93-1) was added using a graduated serological pipettor and mixed by stirring until homogenous. Gradually, 472.8 grams of Guanidine Thiocyanate was added to the combined solution, mixed until thoroughly dissolved, and brought to a final volume of 1 L using $dH_2O$. The final concentrations of each component of the ReX Lysis Buffer (ReX-LB) are: Tris (pH 8.0, Cf=50 mM); EDTA (pH 8.0, Cf=25 mM); Triton X-100 (3% v/v); Urea (Cf=10 mM); Bromophenol Blue (Cf=0.01% v/v); and Guanidine Thiocyanate (Cf=4M).

Preparation of the Rex Wash Buffer (ReX-WB)

50 ml of $dH_2O$ was pre-heated to 67±3° C. on a heating stir-plate with stir bar, and the following Prepared Laboratory Reagents were added in sequential order: i. 9.9 ml of 1M Tris (pH 8.0), and ii. 15 ml of 0.5M EDTA (pH 8.0). Gradually, 212.7 grams of Guanidine Thiocyanate was added to the combined solution, mixed until thoroughly dissolved and brought to a final volume 15 to 300 ml with $dH_2O$. The ReX Wash Buffer (ReX-WB) was brought to a final volume of 1 L with 700 ml of 100% USP-grade Ethanol (CAS 64-17-5). The final concentrations of each component of the ReX-WB are: Tris (pH 8.0, Cf=10 mM); 0.5M EDTA (pH 8.0, 7.5 mM); Guanidine Thiocyante (1.82 M); Ethanol (Cf=70%).

Preparation of the ReX Elution Buffer (ReX-EB)

Preparation of the ReX-EB consisted of adding 10 ml of 1M Tris (pH 8.0) and 2.0 ml of 05M EDTA (pH 8.0) to 88.0 ml of $dH_2O$. The final ReX-EB solution was filter sterilized by 0.2 μm filtration. The final concentrations of each component of the ReX-EB are: Tris (pH 8.0, Cf=100 mM); EDTA (pH 8.0, 10 mM).

Primers and Probes

The sequences of influenza A, influenza B, SARS-CoV-2, and RNase P were taken directly from the Center for Disease Control and Prevention (CDC) Research Use Only (RUO) FluSC2 multiplex assay (SEQ ID NOs:1-8, 13, 14) (Prevention, 2021). However, the probe fluorophore and quencher designs were modified for use on real-time instruments to promote increased detection wider separation of fluorophore reporters and quencher design minimize crossover (SEQ ID NO:15-18). Additionally, the use of the TaqMan Fast Virus 1-Step Master (ThermoFisher Scientific, Cat 4444434) is specially formulated for use with multiplex RT-PCR assays from a range of specimen types, has been optimized to work under a range of common PCR-inhibitors, and contains ROX as a passive-reference dye which functions as a basis for normalization to eliminate detection of crossover fluorescence by the molecular platform (Biosystems, 2010). FluV19 primers and probes were purchased from GenScript® Biotech (Piscataway, NJ) using the sequences and fluorophore/quencher combinations (SEQ ID NOs:1-20).

Additionally, CDC FLuSC2 primers and probes were also purchased from Integrated DNA Technologies (Coralville, Iowa) for use as a comparator against the modified probe fluorophore/quencher design.

PCR Enzymes Mix Reagents

The TaqPath 1-Step Multiplex Mix without ROX (A28523) for testing of the CDC FLuSC2 assay was purchased from Applied Biosystems and the preparation for the master mix can be found at Prevention, 2021.

The TaqMan™ Fast Virus 1-Step Master Mix with ROX (4444434) used with the Reditus FluV19 RT-PCR assay was purchased from Applied Biosystems. The preparation for the master mix is indicated in Table 3 and Table 5.

In Silico Analysis of Viral Core Sequences for Development of a Positive Template Control The pMK-FluV19 positive control plasmid contains core sequences of: i) influenza A Matrix 1 protein (M1), ii) influenza B non-structural protein (NS1), iii) SARS-CoV-2 Nucleoprotein (N), and iii) Human RNase P (RP). To identify the core sequences of each pathogen target needed to produce a positive amplification profile, Geneious Prime® 2021.0.3 was used to perform a MAAFT alignment of target gene sequences for each of the viral pathogens to identify the core-sequence to integrate into the positive control plasmid herein referred to as pMK-FluV19.

For influenza A, 32,955 sequences of the matrix 1 (M1) gene were obtained from the NIAID Influenza Research Database (IRD) (Zhang et al., 2017) and were aligned against the curated primer and probe sequences (Prevention, 2021). While several minor C-A/A-C mismatches were identified within the primer and probe sequences of the M1 gene this did not significantly affect positive amplification (Stadhouders et al., 2010). Thus, sequence alignment indicated that the core sequence would provide detection of approximately ≥90% of all influenza A viruses by RT-PCR analysis. However, it remains possible that future mutations within the influenza B NS1 gene may affect detection of variants.

Similarly, 11,648 sequences of Influenza B Non-structural protein (NS1) were obtained from the NIAID Influenza Research Database (IRD) (Zhang et al., 2017) and were aligned against the curated primer and probe sequences (Prevention, 2021). As with alignment of influenza A primer/probe sets, no significant discrepancies in primer/probe binding were observed leading to a failure in detection of influenza B. Therefore, sequence alignment indicated that the cores sequence would provide detection of approximately ≥90% of all influenza B viruses by RT-PCR. However, it remains possible that future mutations within the influenza B NS1 gene my affect detection of variants. Data was obtained from the NIAID Influenza Research Database (IRD) (Zhang et al., 2017).

The 13,099 nucleotides of the SARS-CoV-2 Nucleoprotein (N) gene were obtained from the NIAID Virus Pathogen Database and Analysis Resource (ViPR) (Pickett et al., 2012) through the website at www.viprbrc.org. Alignment of the N-gene sequences with the curated CDC primers and probe (Prevention, 2021) indicated that ≥95% of all SARS-CoV-2 N-gene sequences should be detected by RT-PCR using the current primer probe sequences with minor C/T substitutions within the forward primer and probe sequences that should not affect detection (Stadhouders et al., 2010). However, it remains possible that future mutations within the N-gene my affect detection of variants.

Use of Total Human Control RNA as a Non-Viral Extraction Control (NVC)

Human total RNA control (50 ng/μl) was purchased from Applied Biosystems (Cat #4307281, Foster City, CA). Total control RNA was diluted to a starting concentration of 1.0 ng/μl in 10 mM Tris (pH 8.0) and serial diluted in a final volume of 1 ml at 0.5 log increments in Tris (pH 8.0) from 1.0 ng/μl to 0.0316 ng/μl. A total of 200 μl of each dilution was extracted in triplicate using ReX reagents on the KingFisher extraction platform and analyzed by RT-PCR on a QuantStudio 12K Flex real-time instrument using 5 μl of elution in a total reaction volume of 20 μl (Table 4).

Development of pMK-FluV19 Positive Template Control (PTC)

Figure 4:
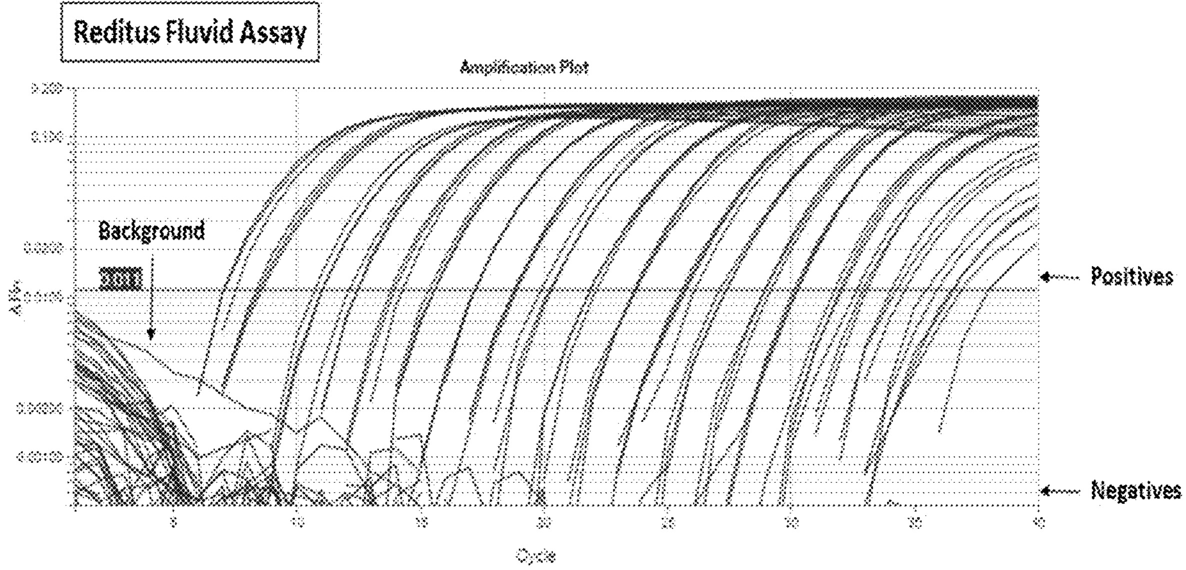
FIG. 4 is a graph showing representative results using a composition and method of the present invention. Those methods show surprisingly low background levels as well as greater analytical sensitivity and accuracy than prior art methods.

The core sequences of Influenza A (M1), Influenza B (NS1), SARS-CoV-2 (N), and Human RNase P developed by in silico analysis were constructed using Geneious Prime® 2021.0.3 software. Leader and flanking sequences for each viral and human target gene were incorporated along with unique restriction sites for post-synthesis digest and analysis and for subcloning of additional/alternate gene products for future use (FIG. 4B). The total sequence presented in FIG. 4B was synthesized by GeneArt Gene Synthesis from Invitrogen (Thermo Fisher Scientific) in pMK-T backbone containing a Kanamycin resistance marker (FIG. 4A). The final construct was verified by sequencing and demonstrated 100% sequence identity of the insertion site.

Lyophilized pMK-FluV19 plasmid was resuspended at a concentration of 5 ng/μl in sterile 10 mM Tris (pH 8.0) and 1 μl of pDNA was used to transform competent DH5α *E. coli* for 20-minutes on ice. DH5α cells were heat-shocked at 42° C. for 40-seconds, placed on ice for 2-minutes, and 1 ml of sterile nutrient-rich Tryptic Soy Broth (TSB) for 1-hour prior. A total of 200 μl of transformed bacteria were plated on Tryptic Soy Agar plates containing 66 μg/ml of Kanamycin to preferentially enrich for *E. coli* containing the pMK-FluV19 vector. Isolated colonies were identified and enriched overnight in TSB containing 66 μg/ml Kanamycin and plasmid DNA was extracted using the A7510 Wizard® Plus Miniprep DNA Purification System (Promega, Madison, WI). One microgram (1 μg) of plasmid DNA was digested with SpeI, KpnI, and XbaI to verify successful transformation. A single isolate was selected which contained a 2,461 bp fragment (KpnI/XbaI), 279 bp fragment (SpeI/KpnI), and a 156 bp fragment (XbaI/SpeI). The selected isolate was cultured in TSB containing 66 μg/ml Kanamycin until log-phase growth was achieved. A glycerol stock of the cultured isolate was prepared by transferring 1 ml of log-phase culture into 427 μl of sterile 50% glycerol. The glycerol stock was maintained at ≤−70° C. for long-term storage.

Estimated Limit of Detection (LOD)

The estimated limit of detection (LOD) was established using linearized pMK-FluV19 plasmid. Specifically, 40 μg of pMK-FluV19 was linearized by digesting with 600 units of KpnI enzyme in CutSmart® buffer (New England Biolabs©) for 4 hours at 37° C. Complete digestion of pMK-FluV19 was confirmed by gel electrophoresis. Linearized pMK-FluV19 was purified overnight at −20° C. in 70% ethanol containing 8.3 mM EDTA and 0.17 M ammonium acetate ($NH_4OAc$) and collected by centrifugation at 21,000×g for 15-minutes at 4° C. Linearized pMK-FluV19 was washed with cold 70% ethanol to remove salts and the resulting pellet was dried and re-suspended in 40 μl of RNase-free 10 mM Tris (pH 8.0). The linearized pMK-FluV19 was centrifuged at 21,000×g for an additional 15-minutes to remove precipitated KpnI. A total of 19.8 μg of linearized pMK-FluV19 was purified as identified by spectrophotometry using a NanoDrop One$^C$ (Thermo Fisher Scientific, Waltham, MA).

Linearized pMK-FluV19 was diluted to a starting concentration of 41 ng/μl and diluted in 0.5 log increments to a final concentration $4.10\times10^{-8}$ ng/μl (i.e. $10^0$ to $10^{-9}$). Thus, the copies of viral gene targets being tested ranged from an estimated $1.38\times10^{10}$ to $1.4\times10^0$ target equivalent/O. A total of 5 μl of each dilution was tested in triplicate by real-time PCR using the CDC FluSC2 multiplex assay as outlined in Prevention, 2021, and by the Reditus FluV19 RT-PCR multiplex (Table 5).

Clinical Validation Specimens influenza A and influenza B clinical specimens used for validation of the Reditus FluV19 RT-PCR assay were obtained from the courtesy of Katie Caldwell at the Illinois Department of Public Health (Springfield, IL) and from courtesy of Matt Charles at NorthShore University HealthSystem (Evanston, IL). Previously reported SARS-CoV-2 negative positive clinical specimens were retained by Reditus Laboratories from prior analysis using the Thermo Fisher TaqPath COVID-19 Combo Kit. Negative clinical specimens were independently confirmed to be Influenza A and Influenza B negative using both the Reditus FluV19 and CDC FLuSC2 primer and probe sets.

To represent dual infection scenarios, combination-positive specimens were generated by diluting high-positive (low Cq value) Influenza A, Influenza B, and SARS-CoV-2 specimens using negative specimens as the diluent to achieve high (H) and low (L) combinations for each of the following scenarios:

| Sample ID | Analyte 1 | Analyte 2 | Analyte 3 |
|---|---|---|---|
| AH-BH | Influenza A High | Influenza B High | — |
| AH-BL | Influenza A High | Influenza B Low | — |
| AH-CH | Influenza A High | SARS-CoV-2 High | — |
| AH-CL | Influenza A High | SARS-CoV-2 Low | — |
| BH-CH | Influenza B High | SARS-CoV-2 High | — |
| BH-CL | Influenza B High | SARS-CoV-2 Low | — |
| AL-BH | Influenza A Low | Influenza B High | — |
| AL-BL | Influenza A Low | Influenza B Low | — |
| AL-CH | Influenza A Low | SARS-CoV-2 High | — |
| AL-CL | Influenza A Low | SARS-CoV-2 Low | — |
| BL-CH | Influenza B Low | SARS-CoV-2 High | — |
| BL-CL | Influenza B Low | SARS-CoV-2 Low | — |
| AH-BH-CH | Influenza A High | Influenza B High | SARS-CoV-2 High |
| AH-BH-CL | Influenza A High | Influenza B High | SARS-CoV-2 Low |
| AL-BL-CH | Influenza A Low | Influenza B Low | SARS-CoV-2 High |
| AL-BL-CL | Influenza A Low | Influenza B Low | SARS-CoV-2 Low |

Equipment, Software, and Analysis

RT-PCR analysis was conducted using QuantStudio 12K Flex Real-Time molecular platforms (Carlsbad, CA). Instruments were calibrated for each of the fluorescent dyes used for etection of specific targets. Analysis of run data was performed using Applied Biosystems Design & Analysis Software version 2.4.0 (Thermo Fisher Scientific, Waltham, MA)

Bioinformatics and sequence analysis was performed using Geneious Prime Software version 2021.0.3 (Biomatters Ltd., San Diego, CA). Sequence alignments were performed in Geneious Prime using the MAFFT Alignment v.7.450 as described inKatoh and Standley, 2013.

Graphical analysis of data was performed using GraphPad Prism 6.01 (San Diego, CA) and statistical analysis (where indicated) was performed using a paired t-test assuming equal variances. Unless indicated elsewhere graphed data represent the mean±sem.

Figure 14:
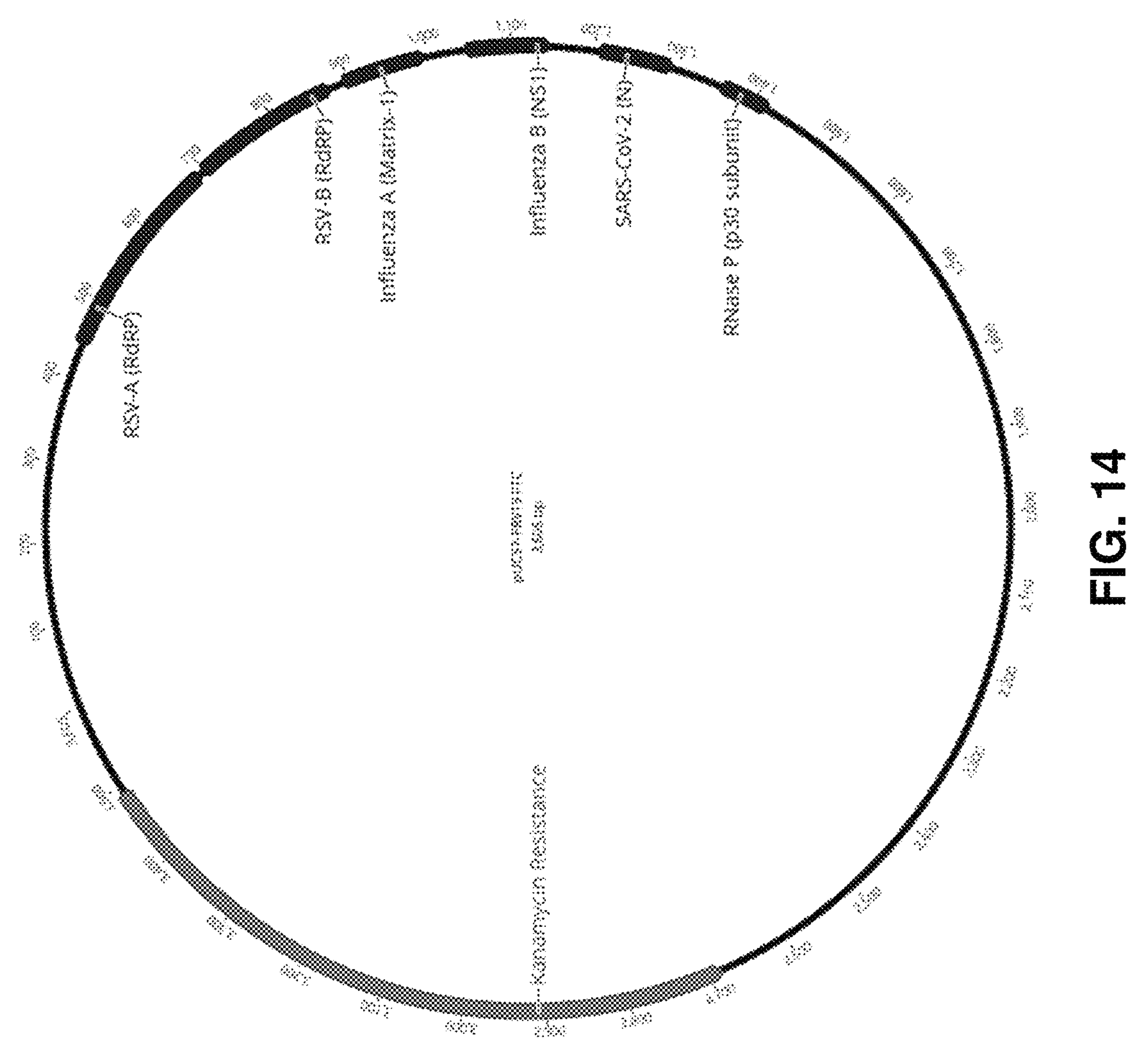
FIG. 14 is an annotated map of pFRV19.

Example 2. Development of a Multiplex RT-PCR Assay for the Detection of Influenza a, Influenza B, SARS-CoV-2, RSV-A, and RSV-B in Clinical Upper Respiratory Samples A multiplex assay was developed using the same primers, probes, reagents and methods as in Example 1, with the addition of primers and probes of respiratory syncytial virus subtype A (RSV-A) and respiratory syncytial virus subtype B (RSV-B) (SEQ ID NOs:9-12, 19 and 20) and the substitution of plasmid pFRV19 (SEQ ID NO:29) for plasmid pMK-FluV19 (SEQ ID NO:28), where plasmid pFRV19 includes the addition of RSV-A and RSV-B target sequences (SEQ ID NOs:25 and 26). An annotated map of pFRV19 is shown in FIG. 14.

Results

The FRV-19 Multiplex RT-PCR Assay can Detect as Few as 30 Gene Equivalents Per PCR Reaction Example 1 teaches a FluV19 multiplex RT-PCR assay for detecting Influenza A, Influenza B, and SARS-CoV-2 in clinical samples. The FluV19 laboratory developed assay was tested against the CDC FluSC2 and ThermoFisher TaqMan COVID-19 FluA, FluB Multiplex Assay and demonstrated greater analytical sensitivity and accuracy than either the CDC or ThermoFisher assays (Example 1). Reditus implemented the FluV19 multiplex assay into clinical testing in early 2021 and has been successful in detecting and reporting Influenza and SARS-CoV-2 positive specimens. Due to the recent increase in RSV cases throughout the U.S., we were interested in adding RSV to the panel of viral targets covered by the current FluV19 assay. To this end, primer and probe sets were developed individually against the RNA-Dependent RNA Polymerase (RdRP) of RSV strains A and B. Due to filter constraints of many molecular platforms, both probes developed for detecting RSV-A and RSV-B contain the same 5'ROX reporter and will not be capable of distinguishing between RSV-A and RSV-B during infection. We determined this was not a limitation as there is no significant difference in clinical severity between RSV-A and RSV-B and does not change the course of treatment of infected patients (Laham et al., 2017; Ciarlitto et al., 2019).

Addition of both the RSV-A and RSV-B RdRP gene was also used to redesign the previous pMK-F1UV19 positive control into a new pUC57 backbone herein referred to as pUC57-FRV19. The updated pUC57-FRV19 positive template control contains all gene targets to include: i) Influenza A Matrix 1 protein (M1), ii) Influenza B Non-structural protein (NS1), iii) SARS-CoV-2 Nucleoprotein (N), iv. RSV-A (RdRP), v. RSV-B (RdRP), and iv) p30 subunit of Human RNase P (RP) (FIG. 14).

Therefore, a test was conducted to determine the limit of detection of each target independently (singleplex) and collectively as a part of the combined FRV19 multiplex assay. Briefly, pUC57-FRV19 assay was extracted from transformed *E. coli* and isolated using the A7510 Wizard® Plus Miniprep DNA Purification System (Promega, Madison, WI). Plasmid DNA (pDNA) was quantified using a NanoDrop One$^{C}$ spectrophotometer (Thermo Fisher Scientific, Waltham, MA) and diluted in 10 mM Tris (pH 8.0) to a starting concentration of $1.99\times10^4$ viral gene equivalents/µl. The pUC57-FRV19 positive template control (PTC) was further diluted in 0.5 log increments to an ending concentration of 2 viral gene equivalents/0. A total of 5 µl of each dilution was tested in triplicate by real-time PCR using reaction volumes and concentrations listed in Table 7. To maintain concentration of primers and probes throughout the PCR reaction, reactions setup to test individual viral targets (singleplex) replaced all other primers and probes with equal volumes of molecular grade water (Table 7).

TABLE 7

| FRV19 Multiplex RT-PCR Master Mix | | | | | |
|---|---|---|---|---|---|
| Reagent | 1x (μl) | 2x (μl) | 10x (μl) | 50x (μl) | 100x (μl) |
| InfA Fwd-1 (3.33 μM) | 0.5 | 1.0 | 5.0 | 25.0 | 50.0 |
| InfA Fwd-2 (3.33 μM) | 0.5 | 1.0 | 5.0 | 25.0 | 50.0 |
| InfA Rev-1 (5.0 μM) | 0.5 | 1.0 | 5.0 | 25.0 | 50.0 |
| InfA Rev-2 (1.67 μM) | 0.5 | 1.0 | 5.0 | 25.0 | 50.0 |
| InfA Probe (1.67 μM) | 0.5 | 1.0 | 5.0 | 25.0 | 50.0 |
| InfB Fwd-2 (6.67 μM) | 0.5 | 1.0 | 5.0 | 25.0 | 50.0 |
| InfB Rev-1 (6.67 μM) | 0.5 | 1.0 | 5.0 | 25.0 | 50.0 |
| InfB Probe (1.67 μM) | 0.5 | 1.0 | 5.0 | 25.0 | 50.0 |
| RSV_A Fwd (3.33 μM) | 0.5 | 1.0 | 5.0 | 25.0 | 50.0 |
| RSV_A Rvs (3.33 μM) | 0.5 | 1.0 | 5.0 | 25.0 | 50.0 |
| RSV_A Probe (1.67 μM) | 0.5 | 1.0 | 5.0 | 25.0 | 50.0 |
| RSV_B Fwd (3.33 μM) | 0.5 | 1.0 | 5.0 | 25.0 | 50.0 |
| RSV_B Rvs (3.33 μM) | 0.5 | 1.0 | 5.0 | 25.0 | 50.0 |
| RSV_B Probe (1.67 μM) | 0.5 | 1.0 | 5.0 | 25.0 | 50.0 |
| SARS-CoV-2 Fwd (6.67 μM) | 0.5 | 1.0 | 5.0 | 25.0 | 50.0 |
| SARS-CoV-2 Rev (6.67 μM) | 0.5 | 1.0 | 5.0 | 25.0 | 50.0 |
| SARS-CoV-2 Probe (1.67 μM) | 0.5 | 1.0 | 5.0 | 25.0 | 50.0 |
| RNase P Fwd (9.0 μM) | 0.5 | 1.0 | 5.0 | 25.0 | 50.0 |
| RNase P Rev (9.0 μM) | 0.5 | 1.0 | 5.0 | 25.0 | 50.0 |
| RNase P Probe (3.0 μM) | 0.5 | 1.0 | 5.0 | 25.0 | 50.0 |
| Fast Virus Enzyme (4x) | 5.0 | 10.0 | 50.0 | 250.0 | 500.0 |
| Molecular Grade Water | 0.0 | 0.0 | 0.0 | 0.0 | 0.0 |
| Total Reaction Volume | 15.0 | 30.0 | 150.0 | 750.0 | 1,500.0 |

Analysis of influenza A by singleplex and multiplex PCR demonstrated an ability to detect the M1 gene as low as 9.95 copies per PCR reaction with <2 Cq difference in detection between singleplex and multiplex assays. When linear regression was applied to assess the efficiency in singleplex and multiplex assays, the coefficient in determination demonstrated a high degree of equivalence between singlplex and multiplex assays ($R^2$=0.9958). Similarly, Influenza B was also detected equally between all dilutions tested with <2 cycles observed in detection between singleplex and multiplex assays and resulted in an $R^2$=0.9974 when regression analysis was applied. Detection of SARS-CoV-2 was also successful at detecting as low as 9.95 copies per PCR reaction but displayed 20-50-times greater ability to detect SARS-CoV-2 at higher N-gene equivalents (99,500-3,150) by singleplex PCR and <4-fold as N-gene copies was reduced from 99.5 N-gene copies per reaction. Regardless, this did not prevent the FRV19 multiplex assay from detecting as low as 9.95 N-gene copies per PCR reaction. Furthermore, regression analysis demonstrated an equivalent correlation between singleplex and multiplex detection of SARS-CoV-2 N-gene with an $R^2$=0.9729. No difference in amplification was observed between singleplex and multiplex detection of RSVA/B across any dilution of pUC57-FRV19 tested with the lower limit of detection being identified at 31.5 RdRP-gene equivalents and a coefficient of determination resulting in an $R^2$=0.9848. Lastly, the RNase P gene was also analyzed as it functions as the internal extraction control present in all human cells in clinical samples. As expected, detection of RNase P (RP) was detected in all 9 dilutions ranging from 99,500 to 9.95 RP-gene equivalents with less than a 5-fold difference in detection with an $R^2$=0.9914 demonstrating equivalence between singleplex and multiplex assays.

The PCR efficiency of the multiplex assay was also calculated based on the standard curve of pUC57-FRV19 with known concentrations of dilutions prepared and tested as part of the limit of detection experiment. Based on the collected data the PCR efficiency of the assay demonstrated an optimized PCR assay as indicated by slopes ≤−3.2 for all viral target amplification. Thus, the overall PCR efficiency is 92.31±0.063% for influenza A, 95.425±0.085% for influenza B, 96.916±0.122% for SARS-CoV-2, 100.772+0.1% for RSV, and 105.064±0.06% for RNase P.

Collectively, these data demonstrate that the FRV19 multiplex assay is equally as efficient at detecting influenza A, influenza B, SARS-COV-2, RSV, and RNase P as PCR reactions that test targets in individual PCR reactions. While influenza A, influenza B, SARS-CoV-2, and RNase P can be detected as low as 9.95 gene equivalents per PCR reaction, RSV was only able to be consistently detected (i.e. in triplicate) as low as 31.5 gene copies per reaction. Therefore, the lower limit of detection (LOD) of the assay is estimated to be ~31.5 gene copies per reaction for the FRV19 multiplex assay. Furthermore, based on the mean±sem of triplicate values at the lower limit of each analyte, the cut-off for the assay was set to Cq<37.00 for future experiments. This cutoff was based on detection of all targets as the mean±sem for influenza A, influenza B, SARS-CoV-2, and RNase P approached 37 cycles at the lowest dilution of 31.5 or 9.95 copies per PCR reaction.

Detection of Influenza a, Influenza B, SARS-CoV-2, RSV-A, and RSV-B is not Prohibited in the Presence of Competing Upper Respiratory Pathogens The limit of detection (LOD) study demonstrated that the FRV19 multiplex assay offered equal detection of influenza A, influenza B, SARS-CoV-2, RSV, and RNase P as detection of each target by individual PCR. However, these data were based exclusively on PCR amplification of targets from the pUC57-FRV19 plasmid. Thus, there was no assessment of amplification following reverse transcription of RNA from either viral targets or the human RNase P gene. Therefore, we sought to determine if the addition of RSV-A/B to the FRV19 multiplex assay would reduce the limit of the detection of Influenza A, Influenza B, RSV. or SARS-CoV-2 in clinical samples. To this end, a validation study was conducted using clinicals samples containing competing bacteria and/or viruses which were either: i) virus-negative, ii) single virus-positive, or iii) virus-positive with each combination of viral targets.

A total of 165 SARS-CoV-2-negative clinical samples were selected for use as diluent in preparing validation samples. Samples were collected from anterior, mid-turbinate, and nasopharyngeal swabs in 3 ml of viral transport media (VTM) and were re-tested for the presence for Influenza A, Influenza B, SARS-CoV-2, and RSV by RT-PCR using the FluV19 multiplex assay. All n=165 samples were confirmed negative for SARS-CoV-2. All n=165 samples were detected for RNase P. However, n=3 SARS-CoV-2 negative samples tested positive for influenza A, n=1 sample tested positive for influenza B, and n=1 sample tested positive for RSV. These samples were excluded from testing and/or use as negative specimen diluent. In total, n=160 samples confirmed to be virus-negative were selected for use in preparing clinical validation samples.

To verify specificity of all FRV19 primer and probe targets as well as sensitivity and accuracy of the FR19 multiplex assay, competing bacteria, fungi, and/or viruses were inoculated in each clinical sample. For competing bacteria/fungi, purchased ATCC strains of *S. pneumoniae, K. pneumoniae, P. aeruginosa, S. epidermidis, C. albicans, S. pyogenes*, and a clinical isolate of *L. pneumophila* serogroup-1 were quantified by culture and optical density. Cultures were pelleted by centrifugation and resuspended in sterile VTM. Bacterial suspensions in VTM were used to inoculate each sample with ≤300 cfu/ml of each respective organism. For competing viruses, purchased ATCC strains of Varicella zoster virus (VZV) and Human Adenovirus C (HAdV-5) were diluted in sterile VTM to achieve ≤300 pfu/ml and used to inoculate each sample.

For preparing specific virus-positive samples, the certificates of analysis provided with purchased ATCC strains of influenza A, influenza B, RSV-A, and RSV-B were used to dilute each specific virus to a concentration of 4,000 pfu/ml in sterile VTM. This represented a 2× stock of each specific virus such that when diluted 1:2 into each specimen (containing competing agents) the final concentration of virus would equal 2,000 pfu/ml. These concentrations are based on a 200 µl extraction and accounting for ~30% loss of nucleic acid recovery from extraction. Thus, the calculated viral titer at 2,000 pfu/ml was anticipated to be between 2- to 3-times the limit of detection of the FRV19 assay as defined by the following equation:

$$\frac{2{,}000\,pfu}{\text{ml}} \times \frac{0.2\text{ ml}}{\text{extraction}} = \frac{400\,pfu}{\text{extraction}} \times \frac{0.27\%\text{ extraction loss}}{\text{elution}} = \frac{108\,pfu}{\mu l} = \frac{20\,pfu}{\mu l} \times \frac{5\,\mu l}{PCR\text{ Reaction}} = \frac{100\,pfu}{PCR\text{ reaction}} = 3x\text{'s the } LOD.$$

A total of 160 samples were prepared which included n=10 virus-negative samples, and n=10 each of the following virus-positive specimens: i) influenza A, ii) influenza B, iii) SARS-CoV-2, iv) RSV-A, v) RSV-B, vi) influenza A+influenza B, vii) influenza A+SARS-CoV-2, viii) influenza A+RSV-A, ix) influenza A+RSV-B, x) influenza B+SARS-CoV-2, xi) influenza B+RSV-A, xii) influenza B+RSV-B, xiii) SARS-CoV-2+RSV-A, xiv) SARS-CoV-2+RSV-B, and xv) All specific virus targets.

Once prepared, 200 µl of each sample and control was extracted vortexing for 5-10 seconds. The 200 µl non-viral extraction control (NVC) containing 0.1 ng/µl of total Human RNA (Applied Biosystems Cat #4307281) and 200 µl of each sample was transferred into KingFisher 96-well deepwell plates containing 265 µl of lysis buffer and 10 µl of MagMax DNA/RNA binding beads (Applied Biosystems, Cat #A42362). Clinical samples and the NVC were lysed for 1-minute at room temperature followed by addition of 640 µl of 80% Ethanol to each sample. The deepwell plate containing samples were transferred to the KingFisher magnetic particle processor and were extracted using the MVP_2Wash_200_Flex protocol which includes a single wash with 500 µl of Wash Buffer (Materials and Methods), 1,000 µl wash with 80% Ethanol, and 50 µl elution in buffer (Materials and Methods). A total of 5 µl of eluted nucleic acid was amplified using the FRV19 Multiplex RT-PCR Master Mix outlined in Table 7. A PCR positive template control (PTC) was included and consisted of 5 µl of pUC57-FRV19 at a concentration of 2,000 copies/µl for consistent amplification at ~25 cycles for all targets.

Post amplification analysis was performed using Applied Biosystems Design and Analysis Software v.2.6.0 using a positive cut-off of 37 cycles as defined by the limit of detection study.

Analysis of amplification data demonstrated that each independent- and combined-positive specimen were detected within the expected 2- to 3-times LOD ranges. Each of the n=160, clinical samples amplified the Human RNase P gene indicating that each sample contained human epithelial cells collected during swabbing. All of the n=10, virus-negative samples amplified only RNase P and no virus-specific targets. These data demonstrate that neither the >300 cfu/ml competing bacteria/fungi or >300 pfu/ml viruses used in inoculating samples contained any sequences which could either inhibit PCR or generate false-positive amplification results. All single-infected, and co-infected virus-positive samples (Σ=140) were successfully detected for influenza A, influenza B, SARS-COV-2, RSV-A, and RSV-B at the appropriate Cq ranges. Of the n=10, clinical samples containing 20 pfu/µl of each virus, only n=2 samples were undetected for SARS-CoV-2 and would have resulted in false-negative results. While the FRV19 assay was unable to detect these n=2 samples, these samples contained all tested viruses. While it is possible that a single person may be simultaneously infected with all 5 viruses, this scenario is not clinically plausible. Thus, the n=10 specimens containing influenza A, influenza B, SARS-CoV-2, RSV-A, RSV-B, and human cells (RP) were used to the test the limits of the FRV19 assay which succeeded in detecting 58 of the 60 targets (96.7%) across the subset of combined samples.

Clinical analytical statistics were then applied to determine the sensitivity, specificity, precision, and accuracy of the FRV19 assay (Table 8). The FRV19 multiplex RT-PCR assay detected $^{60}/_{60}$ (100%) of all influenza A positive samples with no false-negative or false-positive results (Table 8). This resulted in 100% sensitivity, specificity, precision, and accuracy of the FRV19 assay in detecting influenza A in clinical samples (Table 8). Likewise, the FRV19 multiplex assay was 100% sensitive, specific, precise, and accurate in detecting $^{60}/_{60}$ influenza B-positive specimens with no false-negative or false-positive results detected (Table 8). Of the n=45, RSV-A- and n=45, RSV-B-positive specimens (Σ=90), all samples were detected below the cut-off of the assay resulting in 100% for all clinical statistics (Table 8). As mentioned previously, n=2 clinical samples were not detected for SARS-CoV-2 in specimens containing all viruses leading to n=2, SARS-CoV-2 false-negative results obtained by the FRV19 assay. Thus, while the overall specificity and precision of the FRV19 assay to detect SARS-CoV-2 was 100%, the sensitivity and accuracy of detecting SARS-CoV-2 dropped slightly to 96.8% and 98.8%, respectively (Table 8).

TABLE 8

| Analytical Statistics | | Analytical Statistics | |
|---|---|---|---|
| Influenza A | Values | Influenza B | Values |
| # True Positives (a) | 60 | # True Positives (a) | 60 |
| # False Positives (c) | 0 | # False Positives (c) | 0 |
| # True Negatives (d) | 100 | # True Negatives (d) | 100 |
| # False Negatives (b) | 0 | # False Negatives (b) | 0 |
| Sensitivity [a/(a + b)] | 100.0% | Sensitivity [a/(a + b)] | 100.0% |
| Specificity [d/(c + d)] | 100.0% | Specificity [d/(c + d)] | 100.0% |
| Precision [a/(a + c)] | 100.0% | Precision [a/(a + c)] | 100.0% |
| Accuracy [(a + d)/(a + b + c + d) | 100.0% | Accuracy [(a + d)/(a + b + c + d) | 100.0% |
| **Analytical Statistics** | | **Analytical Statistics** | |
| SARS-CoV-2 | Values | RSV-A/B | Values |
| # True Positives (a) | 60 | # True Positives (a) | 90 |
| # False Positives (c) | 0 | # False Positives (c) | 0 |
| # True Negatives (d) | 100 | # True Negatives (d) | 70 |
| # False Negatives (b) | 2 | # False Negatives (b) | 0 |
| Sensitivity [a/(a + b)] | 96.8% | Sensitivity [a/(a + b)] | 100.0% |
| Specificity [d/(c + d)] | 100.0% | Specificity [d/(c + d)] | 100.0% |
| Precision [a/(a + c)] | 100.0% | Precision [a/(a + c)] | 100.0% |
| Accuracy [(a + d)/(a + b + c + d) | 98.8% | Accuracy [(a + d)/(a + b + c + d) | 100.0% |

The FRV-19 Multiplex has Low Intra-Assay Variance and Demonstrates Significant Reproducibility Across Time and Temperature The culmination of data collected thus far demonstrate that the FRV19 assay is a robust and efficient multiplex RT-PCR assay capable of detecting ~30 viral gene targets per PCR reaction with greater than 98% accuracy in detecting low titers of influenza A, influenza B, SARS-COV-2, and RSV-A/B in clinical samples containing high amounts of competing bacteria, fungi, and/or viral pathogens. However, clinical validation samples are tested singly without repeated measures to represent bona fide clinical samples tested in a clinical laboratory. Therefore, we were interested to assess the intra-assay variance of the FRV19 over time and temperatures using already prepared clinical validation samples. Specifically, n=11 validation samples were selected which included a single virus-negative sample and individual specimens positive for: i) influenza A, ii) influenza B, iii) SARS-CoV-2, and iv) RSV-B. Additionally, double virus-positive specimens were also included for: i) influenza A+Influenza B, ii) influenza A+SARS-CoV-2, iii) influenza A+RSV-A, iv) influenza B+SARS-CoV-2, v) Influenza B+RSV-B, and vi) SARS-CoV-2+RSV-B. Each sample was extracted as previously described using 200 µl of sample and amplified by FRV19 multiplex RT-PCR to establish the baseline amplification of each sample on Day 0. Samples were then divided into n=3 aliquots and stored at: 1) 2-8° C., 2) 22-27° C., and 3) 37-40° C. At 24-hour intervals spanning n=5 Days, each sample was extracted in triplicate and amplified using the FRV19 multiplex assay and represents: i) n=60, ii) n=45, iii) n=51, iv) n=57, and v) n=180 independent data points for influenza A, influenza B, SARS-CoV-2, RSV, and RNase P, respectively. The total variance ($V_B$) in the assay was calculated as function of the sum of difference between the Day 0 baseline expected value ($V_E$) and the measured value for the same sample over each 24-hours ($V_T$) divided by the total degrees of freedom per temperature for each analyte. This is represented by the following equation $$V_B = \frac{\sum[V_E - V_{T1}, V_E - V_{T2}, V_E - V_{T3} \ldots V_E - V_{T25}]}{DF}.$$

Collective variance data points were graphed as a function of % Confidence ($1/V_B$; y-axis) and temperature (x-axis). Individual variance by sample and temperature was also graphed as function of Cq (y-axis) and Day (x-axis). The metric for determining significance was preestablished for all samples, regardless of temperature, which amplifies the same target ≥3 cycles over Day 0 baseline as this represents a ~10-fold decrease in detection of that target.

With respect to variance of repeatedly detecting influenza A in clinical samples, no significant difference was observed over the 5 Days, regardless of temperature with the mean±sem of values falling within 98% confidence. These data indicate significant reproducibility of the FRV19 assay to detect influenza A-positive specimens with a high degree of accuracy over time with <1.5 Cq change over Day 0 baseline amplification. Similarly, influenza B demonstrated repeated detection over time and temperature with the mean±sem of variance falling within 98% confidence with <1.5 Cq change, regardless of temperature. Detection of SARS-CoV-2 across time and temperature demonstrated slightly more variance than influenza A or influenza B as the mean±sem of samples were detected with ≥95% confidence but below the 98% confidence observed for Influenza A and Influenza B. This was also observed individually when variance was tracked for each SARS-CoV-2 positive specimen with Cq ≥2.1 over baseline Day 0 values but which were still <3 Cq, which represents a <10-fold change over baseline. Thus, while slightly higher variance was observed, the repeated ability to detect SARS-CoV-2 is robust with >95% confidence in the system. Detection of RSV demonstrated slightly lower variance in samples stored at 2-8° C. (>98% confidence) than samples stored at 22-27° C. or 37-42° C. (>95% confidence). However, similar to SARS-CoV-2, the repeated capacity to detect RSV-A and RSV-B in clinical samples is significant with <2.1 Cq change over baseline Day 0 amplification. Lastly, detection of RNase P was consistent for datapoints across time and temperature with no depreciable difference in amplification over Day 0 baseline with ≥98 confidence in repeated detection. These data demonstrate the robust reproducibility of the FRV19 multiplex RT-PCR assay in detecting influenza A, influenza B, SARS-CoV-2, and RSV-A/B in clinical samples. Furthermore, these data suggest that samples may be stored at 2-8° C., room temperature (22-27° C.), and are stable when transported in elevated temperatures (37-40° C.) which may occur when cold packs thaw during commercial shipment to laboratories.

REFERENCES

Administration, F.a.D., *TaqPath* COVID-19 Combo Kit Emergency Use Authorization (EUA). 2020, Food and Drug Administration (FDA).

Altman, S., *Ribonuclease* P. Philosophical transactions of the Royal Society of London. Series B, Biological sciences, 2011. 366(1580): p. 2936-2941.

Biosystems, A., *TaqMan® Fast Virus* 1-*Step Master Mix Product Inser*t. 2010, Life Technologies.

Brunet, A., et al., *How does temperature impact the conformation of single DNA molecules below melting temperature*? Nucleic Acids Research, 2017. 46(4): p. 2074-2081.

Ciarlitto C, Vittucci A C, Antilici L, Concato C, Di Camillo C, Zangari P, et al. Respiratory Syncityal Virus A and B: three bronchiolitis seasons in a third level hospital in Italy. Italian Journal of Pediatrics. 2019; 45(1):115. doi: 10.1186/s13052-019-0704-0.

Lapanje, S., *Denaturation of globular proteins by guanidine thiocyanate I. Optical rotation in aqueous guanidine thiocyanate solutions*. Biochimica et Biophysica Acta (BBA)—Protein Structure, 1971. 243(3): p. 349-356. CLSI, *User Verification of Precision and Estimation of Bias; Approved Guidelines-Third Edition, in CLSI document* EP 15-A3. 2014, Clinical and Laboratory Standards Institute: Wayne, Pa.

Driessen, R. P. C., et al., *Effect of Temperature on the Intrinsic Flexibility of DNA and Its Interaction with Architectural Proteins*. Biochemistry, 2014. 53(41): p. 6430-6438.

Fernandes-Monteiro, A. G., et al., *New approaches for the standardization and validation of a real-time qPCR assay using TaqMan probes for quantification of yellow fever virus on clinical samples with high quality parameters*. Human vaccines & immunotherapeutics, 2015. 11(7): p. 1865-1871.

Gooskens, J., et al., *Morbidity and Mortality Associated With Nosocomial Transmission of Oseltamivir-Resistant Influenza A*(*H*1*N*1) *Virus*. JAMA, 2009. 301(10): p. 1042-1046.

Green, W. D. and M. A. Beck, *Obesity Impairs the Adaptive Immune Response to Influenza Virus*. Ann Am Thorac Soc, 2017. 14(Supplement_5): p. S406-s409.

Innings, A., et al., *Multiplex real-time PCR targeting the RNase P RNA gene for detection* and *identification of Candida* species *in blood*. Journal of clinical microbiology, 2007. 45(3): p. 874-880.

Katoh, K. and D. M. Standley, *MAFFT multiple sequence alignment software version 7: improvements in performance and usability*. Mol Biol Evol, 2013. 30(4): p. 772-80.

Laham F R, Mansbach J M, Piedra P A, Hasegawa K, Sullivan A F, Espinola J A, et al. Clinical Profiles of Respiratory Syncytial Virus Subtypes A AND B Among Children Hospitalized with Bronchiolitis. Pediatr Infect Dis J. 2017; 36(8):808-10. doi: 10.1097/INF.0000000000001596. PubMed PMID: 28383391.

Li, G., et al., *Outcome of critically ill patients with influenza virus infection*. Journal of Clinical Virology, 2009. 46(3): p. 275-278.

Ljungman, P., et al., *Influenza A in Immunocompromised Patients*. Clinical Infectious Diseases, 1993. 17(2): p. 244-247.

Moghadami, M., *A Narrative Review of Influenza: A Seasonal and Pandemic Disease*. Iranian journal of medical sciences, 2017. 42(1): p. 2-13.

Owen, D. B. and Y.-M. Chou, *Effect of Measurement Error and Instrument Bias on Operating Characteristics for Variables Sampling Plans*. Journal of Quality Technology, 1983. 15(3): p. 107-117.

Pickett, B. E., et al., *Virus pathogen database and analysis resource (ViPR): a comprehensive bioinformatics database and analysis resource for the coronavirus research community*. Viruses, 2012. 4(11): p. 3209-3226.

Prevention, C.f.D.C.a., CDC 2019-*Novel Coronavirus* (2019-*nCoV*) *Real-Time RT-PCR Diagnostic Panel*. 2020, CDC, Division of Viral Diseases: Atlanta, GA.

Prevention, C.f.D.C.a., CDC *Influenza SARS-CoV*-2 (*Flu SC*2) *Multiplex Assay, Instructions for Use*. 2021, Centers for Disease Control and Prevention: Atlanta, GA.

Prevention, C.f.D.C.a., *Research Use Only CDC Influenza SARS-CoV*-2 (*Flu SC*2) *Multiplex Assay Primers and Probes*, D.o.V.D. National Center for Immunization and Respiratory Diseases (NCIRD), Editor. 2021, CDC: Atlanta, GA.

Scientific, T. F., *TaqPath™ COVID*-19 *Combo Kit Instructions for Use*, in FDA.gov. 2020: Pleasanton, CA.

Scientific, T. F., *TaqPath™ COVID*-19, *FluA, FluB Combo Kit Instructions for Use*. 2021, Thermo Fisher Scientific: Pleasanton, CA.

Stadhouders, R., et al., *The effect of primer-template mismatches on the detection and quantification of nucleic acids using the 5′ nuclease assay*. The Journal of molecular diagnostics: JMD, 2010. 12(1): p. 109-117.

Stepanenko, O. V., et al., *Distinct Effects of Guanidine Thiocyanate on the Structure of Superfolder* GFP. PLOS ONE, 2012. 7(11): p. e48809.

Willman, D. *Contamination at CDC lab delayed rollout of coronavirus tests*. 2020; Available from: www.washingtonpost.com/investigations/contamination-at-cdc-lab-delayed-rollout-of-coronavirus-tests/2020/04/18/fd7d3824-7139-11ea-aa80-c2470c6b2034_story.html.

Wingfield, P. T., *Use of protein folding reagents*. Current protocols in protein science, 2001. Appendix 3: p. Appendix-3A.

Wozniak, A., et al., *A simple RNA preparation method for SARS-CoV-2 detection by RT-qPCR*. Scientific Reports, 2020. 10(1): p. 16608.

Yee, K. F., *Confidence interval approach for evaluating bias in laboratory methods*. J Automat Chem, 1988. 10(3): p. 144-6.

Zhang, Y., et al., *Influenza Research Database: An integrated bioinformatics resource for influenza virus research*. Nucleic Acids Res, 2017. 45(D1): p. D466-d474.

U.S. Pat. No. 6,015,664.

U.S. Pat. No. 6,881,835.

US Patent Application Publication 2011/0046001.

US Patent Application Publication 20070207453.

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification, including but not limited to patent publications and non-patent literature, and references cited therein, are hereby incorporated by reference. The discussion of the references herein is intended merely to summarize the assertions made by the authors and no admission is made that any reference constitutes prior art. Applicants reserve the right to challenge the accuracy and pertinence of the cited references.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

| SEQUENCES |
|---|
| SEQ ID NO: 1<br>InfA Fwd-1<br>CAAGACCAATCYTGTCACCTCTGAC |
| SEQ ID NO: 2<br>InfA Fwd-2<br>CAAGACCAATYCTGTCACCTYTGAC |
| SEQ ID NO: 3<br>InfA Rev-1<br>GCATTYTGGACAAAVCGTCTACG |
| SEQ ID NO: 4<br>InfA Rev-2<br>GCATTTTGGATAAAGCGTCTACG |
| SEQ ID NO: 5<br>InfBFwd<br>TCCTCAAYTCACTCTTCGAGCG |
| SEQ ID NO: 6<br>InfBRev<br>CGGTGCTCTTGACCAAATTGG |
| SEQ ID NO: 7<br>SARSCOV2Fwd<br>CTGCAGATTTGGATGATTTCTCC |
| SEQ ID NO: 8<br>SARSCOV2Rvs<br>CCTTGTGTGGTCTGCATGAGTTTAG |
| SEQ ID NO: 9<br>RSV-A Fwd<br>ACCAACTTAATTAGTAGACAAAATCCA |
| SEQ ID NO: 10<br>RSV-A Rvs<br>TCTGACGAGGTCATACTCTTGT |
| SEQ ID NO: 11<br>RSV-B Fwd<br>GCATAAGTTTTGGTCTTAGCTTGA |
| SEQ ID NO: 12<br>RSV-B Rvs<br>AAATGTATCTCATTCAGCTTCGGT |
| SEQ ID NO: 13<br>RNP Fwd<br>AGATTTGGACCTGCGAGCG |

-continued

| SEQUENCES |
|---|
| SEQ ID NO: 14<br>RNP Rvs<br>GAGCGGCTGTCTCCACAAGT |
| SEQ ID NO: 15<br>InfAProbe<br>[Cy5]TGCAGTCCTCGCTCACTGGGCACG[BHQ2a-Q] |
| SEQ ID NO: 16<br>InfBProbe<br>[HEX]CCAATTCGAGCAGCTGAAACTGCGGTG[BHQ1a-Q] |
| SEQ ID NO: 17<br>SARSCoV2Probe<br>[6FAM]ATTGCAACAATCCATGAGCAGTGCTGACTC[BHQ1a-Q] |
| SEQ ID NO: 18<br>RNP Probe<br>[TAMRA]TTCTGACCTGAAGGCTCTGCGCG[BHQ2a-Q] |
| SEQ ID NO: 19<br>RSV-A Probe<br>[ROX]AGAAGAACCTACTTACTTTCAGTCA[BHQ2a-Q] |
| SEQ ID NO: 20<br>RSV-B Probe<br>[ROX]TGGAACAATTCACAAACATATGTCCT[BHQ2a-Q] |
| SEQ ID NO: 21<br>Influenza A Conserved Matrix Protein 2 (M2) Target Sequence (168 bp)<br>TGTCCAGAGCTCCTCGAGATGGAATGGCTAAAGACAAGACCAATCTTGTCACCTCTG<br>ACTAAGGGAATTTTAGGATTTGTGTTCACGCTCACCGTGCCCAGTGAGCGAGGACTG<br>CAGCGTAGACGCTTTGTCCAAAATGCCCTAAATGGGAATGGGGACCCGTCTAGA |
| SEQ ID NO: 22<br>Influenza B Conserved Non-Structural Protein 1 (NS1) Target Sequence (156 bp)<br>AACAACATGGCCATCGGATCCTCAATTCACTCTTCGAGCGTCTTAATGAAGGACATT<br>CAAAGCCAATTCGAGCAGCTGAAACTGCGGTGGGAGTCTTATCCCAATTTGGTCAAG<br>AGCACCGACTATCACCAGAAGAGGGAGACAAAACAGACTAGT |
| SEQ ID NO: 23<br>SARS-COV-2 ORF 1ab Target Sequence(150 bp)<br>CAAACTGTGACTCTTCTTCCTGCTGCAGATTTGGATGATTTCTCCAAACAATTGCAAC<br>AATCCATGAGCAGTGCTGACTCAACTCAGGCCTAAACTCATGCAGACCACACAAGG<br>CAGATGGGCTATATAAACGTTTTCGCTTTTCATATG |
| SEQ ID NO: 24<br>Human RNaseP Target Sequence (129 bp)<br>CCGTTTACGATGGCGGTGTTTGCAGATTTGGACCTGCGAGCGGGTTCTGACCTGAAG<br>GCTCTGCGCGGACTTGTGGAGACAGCCGCTCACCTTGGCTATTCAGTTGTTGCTATC<br>AATCCATGGGGTACC |
| SEQ ID NO: 25<br>RSV-A Target Sequence<br>TTACATATTCAATGGTCCTTATCTCAAAAATGATTATACCAACTTAATTAGTAGACA<br>AAATCCATTAATAGAACACATAAATCTAAAGAAACTAAATATAACACAGTCCTTAA<br>TATCTAAGTATCAT |
| SEQ ID NO: 26<br>RSV-B Target Sequence<br>GACATTGTGTTTCAAAATTGCATAAGTTTTGGTCTTAGCTTGATGTCAGTTGTGGAAC<br>AATTCACAAACATATGTCCTAATAGAATTATTCTCATACCGAAGCTGAATGAGATAC<br>ATTTGATGAAAC |
| SEQ ID NO: 27<br>Kanamycin Resistance Sequence<br>ATGATTGAACAGGATGGCCTGCATGCGGGTAGCCCGGCAGCGTGGGTGGAACGTCT<br>GTTTGGCTATGATTGGGCGCAGCAGACCATTGGCTGCTCTGATGCGGCGGTGTTTCG<br>TCTGAGCGCGCAGGGTCGTCCGGTGCTGTTTGTGAAAACCGATCTGAGCGGTGCGCT<br>GAACGAGCTGCAGGATGAAGCGGCGCGTCTGAGCTGGCTGGCCACCACCGGTGTTC<br>CGTGTGCGGCGGTGCTGGATGTGGTGACCGAAGCGGGCCGTGATTGGCTGCTGCTG<br>GGCGAAGTGCCGGGTCAGGATCTGCTGTCTAGCCATCTGGCGCCGGCAGAAAAAGT<br>GAGCATTATGGCGGATGCCATGCGTCGTCTGCATACCCTGGACCCGGCGACCTGTCC<br>GTTTGATCATCAGGCGAAACATCGTATTGAACGTGCGCGTACCCGTATGGAAGCGG<br>GCCTGGTGGATCAGGATGATCTGGATGAAGAACATCAGGGCCTGGCACCGGCAGAG<br>CTGTTTGCGCGTCTGAAAGCGAGCATGCCGGATGGCGAAGATCTGGTGGTGACCCAT<br>GGTGATGCGTGCCTGCCGAACATTATGGTGGAAAATGGCCGTTTTAGCGGCTTTATT |

-continued

| SEQUENCES |
|---|
| GATTGCGGCCGTCTGGGCGTGGCGGATCGTTATCAGGATATTGCGCTGGCCACCCGT<br>GATATTGCGGAAGAACTGGGCGGCGAATGGGCGGATCGTTTTCTGGTGCTGTATGGC<br>ATTGCGGCACCGGATAGCCAGCGTATTGCGTTTTATCGTCTGCTGGATGAATTTTTCT<br>AATAA |
| SEQ ID NO: 28<br>pMK-Flu V19<br>CTAAATTGTAAGCGTTAATATTTTGTTAAAATTCGCGTTAAATTTTTGTTAAATCAGC<br>TCATTTTTTAACCAATAGGCCGAAATCGGCAAAATCCCTTATAAATCAAAAGAATAG<br>ACCGAGATAGGGTTGAGTGGCCGCTACAGGGCGCTCCCATTCGCCATTCAGGCTGC<br>GCAACTGTTGGGAAGGGCGTTTCGGTGCGGGCCTCTTCGCTATTACGCCAGCTGGCG<br>AAAGGGGGATGTGCTGCAAGGCGATTAAGTTGGGTAACGCCAGGGTTTTCCCAGTC<br>ACGACGTTGTAAAACGACGGCCAGTGAGCGCGACGTAATACGACTCACTATAGGGC<br>GAATTGAAGGAAGGCCGTCAAGGCCACGTGTCTTGTCCAGAGCTCCTCGAGATGGA<br>ATGGCTAAAGACAAGACCAATCTTGTCACCTCTGACTAAGGGAATTTTAGGATTTGT<br>GTTCACGCTCACCGTGCCCAGTGAGCGAGGACTGCAGCGTAGACGCTTTGTCCAAA<br>ATGCCCTAAATGGGAATGGGGACCCGTCTAGAAACAACATGGCCATCGGATCCTCA<br>ATTCACTCTTCGAGCGTCTTAATGAAGGACATTCAAAGCCAATTCGAGCAGCTGAAA<br>CTGCGGTGGGAGTCTTATCCCAATTTGGTCAAGAGCACCGACTATCACCAGAAGAG<br>GGAGACAAAACAGACTAGTCAAACTGTGACTCTTCTTCCTGCTGCAGATTTGGATGA<br>TTTCTCCAAACAATTGCAACAATCCATGAGCAGTGCTGACTCAACTCAGGCCTAAAC<br>TCATGCAGACCACACAAGGCAGATGGGCTATATAAACGTTTTCGCTTTTCATATGCC<br>GTTTACGATGGCGGTGTTTGCAGATTTGGACCTGCGAGCGGGTTCTGACCTGAAGGC<br>TCTGCGCGGACTTGTGGAGACAGCCGCTCACCTTGGCTATTCAGTTGTTGCTATCAA<br>TCCATGGGGTACCTGGAGCACAAGACTGGCCTCATGGGCCTTCCTTTCACTGCCCGC<br>TTTCCAGTCGGGAAACCTGTCGTGCCAGCTGCATTAACATGGTCATAGCTGTTTCCTT<br>GCGTATTGGGCGCTCTCCGCTTCCTCGCTCACTGACTCGCTGCGCTCGGTCGTTCGGG<br>TAAAGCCTGGGGTGCCTAATGAGCAAAAGGCCAGCAAAAGGCCAGGAACCGTAAA<br>AAGGCCGCGTTGCTGGCGTTTTTCCATAGGCTCCGCCCCCCTGACGAGCATCACAAA<br>AATCGACGCTCAAGTCAGAGGTGGCGAAACCCGACAGGACTATAAAGATACCAGGC<br>GTTTCCCCCTGGAAGCTCCCTCGTGCGCTCTCCTGTTCCGACCCTGCCGCTTACCGGA<br>TACCTGTCCGCCTTTCTCCCTTCGGGAAGCGTGGCGCTTTCTCATAGCTCACGCTGTA<br>GGTATCTCAGTTCGGTGTAGGTCGTTCGCTCCAAGCTGGGCTGTGTGCACGAACCCC<br>CCGTTCAGCCCGACCGCTGCGCCTTATCCGGTAACTATCGTCTTGAGTCCAACCCGG<br>TAAGACACGACTTATCGCCACTGGCAGCAGCCACTGGTAACAGGATTAGCAGAGCG<br>AGGTATGTAGGCGGTGCTACAGAGTTCTTGAAGTGGTGGCCTAACTACGGCTACACT<br>AGAAGAACAGTATTTGGTATCTGCGCTCTGCTGAAGCCAGTTACCTTCGGAAAAAGA<br>GTTGGTAGCTCTTGATCCGGCAAACAAACCACCGCTGGTAGCGGTGGTTTTTTTGTTT<br>GCAAGCAGCAGATTACGCGCAGAAAAAAAGGATCTCAAGAAGATCCTTTGATCTTT<br>TCTACGGGGTCTGACGCTCAGTGGAACGAAAACTCACGTTAAGGGATTTTGGTCATG<br>AGATTATCAAAAAGGATCTTCACCTAGATCCTTTTAAATTAAAAATGAAGTTTTAAA<br>TCAATCTAAAGTATATATGAGTAAACTTGGTCTGACAGTTATTAGAAAAATTCATCC<br>AGCAGACGATAAAACGCAATACGCTGGCTATCCGGTGCCGCAATGCCATACAGCAC<br>CAGAAAACGATCCGCCCATTCGCCGCCCAGTTCTTCCGCAATATCACGGGTGGCCAG<br>CGCAATATCCTGATAACGATCCGCCACGCCCAGACGGCCGCAATCAATAAAGCCGC<br>TAAAACGGCCATTTTCCACCATAATGTTCGGCAGGCACGCATCACCATGGGTCACCA<br>CCAGATCTTCGCCATCCGGCATGCTCGCTTTCAGACGCGCAAACAGCTCTGCCGGTG<br>CCAGGCCCTGATGTTCTTCATCCAGATCATCCTGATCCACCAGGCCCGCTTCCATAC<br>GGGTACGCGCACGTTCAATACGATGTTTCGCCTGATGATCAAACGGACAGGTCGCCG<br>GGTCCAGGGTATGCAGACGACGCATGGCATCCGCCATAATGCTCACTTTTTCTGCCG<br>GCGCCAGATGGCTAGACAGCAGATCCTGACCCGGCACTTCGCCCAGCAGCAGCCAA<br>TCACGGCCCGCTTCGGTCACCACATCCAGCACCGCCGCACACGGAACACCGGTGGT<br>GGCCAGCCAGCTCAGACGCGCCGCTTCATCCTGCAGCTCGTTCAGCGCACCGCTCAG<br>ATCGGTTTTCACAAACAGCACCGGACGACCCTGCGCGCTCAGACGAAACACCGCCG<br>CATCAGAGCAGCCAATGGTCTGCTGCGCCCAATCATAGCCAAACAGACGTTCCACC<br>CACGCTGCCGGGCTACCCGCATGCAGGCCATCCTGTTCAATCATACTCTTCCTTTTTC<br>AATATTATTGAAGCATTTATCAGGGTTATTGTCTCATGAGCGGATACATATTTGAAT<br>GTATTTAGAAAAATAAACAAATAGGGGTTCCGCGCACATTTCCCCGAAAAGTGCCA<br>C |
| SEQ ID NO: 29<br>pFRV19<br>TCGCGCGTTTCGGTGATGACGGTGAAAACCTCTGACACATGCAGCTCCCGGAGACG<br>GTCACAGCTTGTCTGTAAGCGGATGCCGGGAGCAGACAAGCCCGTCAGGGCGCGTC<br>AGCGGGTGTTGGCGGGTGTCGGGGCTGGCTTAACTATGCGGCATCAGAGCAGATTG<br>TACTGAGAGTGCACCATATGCGGTGTGAAATACCGCACAGATGCGTAAGGAGAAAA<br>TACCGCATCAGGCGCCATTCGCCATTCAGGCTGCGCAACTGTTGGGAAGGGCGATC<br>GGTGCGGGCCTCTTCGCTATTACGCCAGCTGGCGAAAGGGGGATGTGCTGCAAGGC<br>GATTAAGTTGGGTAACGCCAGGGTTTTCCCAGTCACGACGTTGTAAAACGACGGCCA<br>GAGAATTCGAGCTCGGTACCTCGCGAATACATCTAGATCTCGAGATTCAGGTTACAT<br>ATTCAATGGTCCTTATCTCAAAAATGATTATACCAACTTAATTAGTAGACAAAATCC<br>ATTAATAGAACACATAAATCTAAAGAAACTAAATATAACACAGTCCTTAATATCTAA<br>GTATCATAAAGGTGAAATAAAAATAGAAGAACCTACTTACTTTCAGTCATTACTTAT<br>GACATACAAGAGTATGACCTCGTCAGAACAGACTACTACTACTAATTTACTTAAAAA<br>GATAATAAGAAGAGCTCGACATTGTGTTTCAAAATTGCATAAGTTTTGGTCTTAGCT<br>TGATGTCAGTTGTGGAACAATTCACAAACATATGTCCTAATAGAATTATTCTCATAC<br>CGAAGCTGAATGAGATACATTTGATGAAACCTCCTATATTTACAGGAGATGTTGATA |

-continued

| SEQUENCES |
|---|
| TCATCAAGTTGAAGCAAGTGATACAAAAACAGGAATGGCTAAAGACAAGACCAATC<br>TTGTCACCTCTGACTAAGGGAATTTTAGGATTTGTGTTCACGCTCACCGTGCCCAGTG<br>AGCGAGGACTGCAGCGTAGACGCTTTGTCCAAAATGCCCTAAATGGAATGGGGAC<br>CCGTCTAGAAACAACATGGCCATCGGATCCTCAATTCACTCTTCGAGCGTCTTAATG<br>AAGGACATTCAAAGCCAATTCGAGCAGCTGAAACTGCGGTGGGAGTCTTATCCCAA<br>TTTGGTCAAGAGCACCGACTATCACCAGAAGAGGGAGACAAAACAGACTAGTCAAA<br>CTGTGACTCTTCTTCCTGCTGCAGATTTGGATGATTTCTCCAAACAATTGCAACAATC<br>CATGAGCAGTGCTGACTCAACTCAGGCCTAAACTCATGCAGACCACACAAGGCAGA<br>TGGGCTATATAAACGTTTTCGCTTTTCATATGCCGTTTACGATGGCGGTGTTTGCAGA<br>TTTGGACCTGCGAGCGGGTTCTGACCTGAAGGCTCTGCGCGGACTTGTGGAGACAGC<br>CGCTCACCTTGGCTATTCAGTTGTTGCTATCAATCCATGGATCGGATCCCGGGCCCGT<br>CGACTGCAGAGGCCTGCATGCAAGCTTGGTGTAATCATGGTCATAGCTGTTTCCTGT<br>GTGAAATTGTTATCCGCTCACAATTCCACACAACATACGAGCCGGAAGCATAAAGT<br>GTAAAGCCTGGGGTGCCTAATGAGTGAGCTAACTCACATTAATTGCGTTGCGCTCAC<br>TGCCCGCTTTCCAGTCGGGAAACCTGTCGTGCCAGCTGCATTAATGAATCGGCCAAC<br>GCGCGGGGAGAGGCGGTTTGCGTATTGGGCGCTCTTCCGCTTCCTCGCTCACTGACT<br>CGCTGCGCTCGGTCGTTCGGCTGCGGCGAGCGGTATCAGCTCACTCAAAGGCGGTA<br>ATACGGTTATCCACAGAATCAGGGGATAACGCAGGAAAGAACATGTGAGCAAAAG<br>GCCAGCAAAAGGCCAGGAACCGTAAAAAGGCCGCGTTGCTGGCGTTTTTCCATAGG<br>CTCCGCCCCCCTGACGAGCATCACAAAAATCGACGCTCAAGTCAGAGGTGGCGAAA<br>CCCGACAGGACTATAAAGATACCAGGCGTTTCCCCCTGGAAGCTCCCTCGTGCGCTC<br>TCCTGTTCCGACCCTGCCGCTTACCGGATACCTGTCCGCCTTTCTCCCTTCGGGAAGC<br>GTGGCGCTTTCTCATAGCTCACGCTGTAGGTATCTCAGTTCGGTGTAGGTCGTTCGCT<br>CCAAGCTGGGCTGTGTGCACGAACCCCCCGTTCAGCCCGACCGCTGCGCCTTATCCG<br>GTAACTATCGTCTTGAGTCCAACCCGGTAAGACACGACTTATCGCCACTGGCAGCAG<br>CCACTGGTAACAGGATTAGCAGAGCGAGGTATGTAGGCGGTGCTACAGAGTTCTTG<br>AAGTGGTGGCCTAACTACGGCTACACTAGAAGAACAGTATTTGGTATCTGCGCTCTG<br>CTGAAGCCAGTTACCTTCGGAAAAAGAGTTGGTAGCTCTTGATCCGGCAAACAAAC<br>CACCGCTGGTAGCGGTGGTTTTTTTGTTTGCAAGCAGCAGATTACGCGCAGAAAAAA<br>AGGATCTCAAGAAGATCCTTTGATCTTTTCTACGGGGTCTGACGCTCAGTGGAACGA<br>AAACTCACGTTAAGGGATTTTGGTCATGAGATTATCAAAAAGGATCTTCACCTAGAT<br>CCTTTTAAATTAAAAATGAAGTTTTAAATCAAGCCCAATCTGAATAATGTTACAACC<br>AATTAACCAATTCTGATTAGAAAAACTCATCGAGCATCAAATGAAACTGCAATTTAT<br>TCATATCAGGATTATCAATACCATATTTTTGAAAAAGCCGTTTCTGTAATGAAGGAG<br>AAAACTCACCGAGGCAGTTCCATAGGATGGCAAGATCCTGGTATCGGTCTGCGATTC<br>CGACTCGTCCAACATCAATACAACCTATTAATTTCCCCTCGTCAAAAATAAGGTTAT<br>CAAGTGAGAAATCACCATGAGTGACGACTGAATCCGGTGAGAATGGCAAAAGTTTA<br>TGCATTTCTTTCCAGACTTGTTCAACAGGCCAGCCATTACGCTCGTCATCAAAATCAC<br>TCGCATCAACCAAACCGTTATTCATTCGTGATTGCGCCTGAGCGAGACGAAATACGC<br>GATCGCTGTTAAAAGGACAATTACAAACAGGAATCGAATGCAACCGGCGCAGGAAC<br>ACTGCCAGCGCATCAACAATATTTTCACCTGAATCAGGATATTCTTCTAATACCTGG<br>AATGCTGTTTTTCCGGGGATCGCAGTGGTGAGTAACCATGCATCATCAGGAGTACGG<br>ATAAAATGCTTGATGGTCGGAAGAGGCATAAATTCCGTCAGCCAGTTTAGTCTGACC<br>ATCTCATCTGTAACATCATTGGCAACGCTACCTTTGCCATGTTTCAGAAACAACTCTG<br>GCGCATCGGGCTTCCCATACAAGCGATAGATTGTCGCACCTGATTGCCCGACATTAT<br>CGCGAGCCCATTTATACCCATATAAATCAGCATCCATGTTGGAATTTAATCGCGGCC<br>TCGACGTTTCCCGTTGAATATGGCTCATAACACCCCTTGTATTACTGTTTATGTAAGC<br>AGACAGTTTTATTGTTCATGATGATATATTTTTATCTTGTGCAATGTAACATCAGAGA<br>TTTTGAGACACGGGCCAGAGCTGCA |

What is claimed is:

1. A composition for detecting more than one target nucleic acid sequence in a nucleic acid sample by polymerase chain reaction (PCR), the composition comprising
- a plasmid comprising (a) a portion of each of the more than one target nucleic acid sequence, and (b) a sequence encoding a portion of a human housekeeping gene;
- a passive reference dye; and
- a set of two DNA primers and a DNA probe for each of the more than one target nucleic acid sequence and RNase P, wherein each of the probes comprise a dye, wherein the plasmid comprises SEQ ID NO:28 or 29.

2. A composition for detecting more than one target nucleic acid sequence in a nucleic acid sample by polymerase chain reaction (PCR), the composition comprising a plasmid comprising (a) a portion of each of the more than one target nucleic acid sequence, and (b) a sequence encoding a portion of a human housekeeping gene;
- a passive reference dye; and
- a set of two DNA primers and a DNA probe for each of the more than one target nucleic acid sequence and RNase P, wherein each of the probes comprise a dye, wherein the more than one target nucleic acid sequence is RNA from viruses selected from the group consisting of influenza A, influenza B, and SARS-COV-2;

the plasmid comprises SEQ ID NO:28 or 29;

the human housekeeping gene is RNase P;

the passive reference dye is ROX;

the set of two DNA primers for each of the more than one target nucleic acid sequence and the RNase P comprises SEQ ID NOs: 1-10.

* * * * *

SEQUENCE LISTING

<160> NUMBER OF SEQ ID NOS: 29

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
caagaccaat cytgtcacct ctgac 25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
caagaccaat yctgtcacct ytgac 25

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
gcattytgga caaavcgtct acg 23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
gcattttgga taaagcgtct acg 23

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
tcctcaaytc actcttcgag cg 22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
cggtgctctt gaccaaattg g 21

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
ctgcagattt ggatgatttc tcc 23

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ccttgtgtgg tctgcatgag tttag 25

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
accaacttaa ttagtagaca aaatcca 27

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tctgacgagg tcatactctt gt 22

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
gcataagttt tggtcttagc ttga 24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
aaatgtatct cattcagctt cggt 24

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
agatttggac ctgcgagcg 19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gagcggctgt ctccacaagt 20

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic probe

<400> SEQUENCE: 15
tgcagtcctc gctcactggg cacg 24

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 16
ccaattcgag cagctgaaac tgcggtg 27

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic probe

<400> SEQUENCE: 17
attgcaacaa tccatgagca gtgctgactc 30

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 18
ttctgacctg aaggctctgc gcg 23

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 19
agaagaacct acttactttc agtca 25

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic probe

<400> SEQUENCE: 20

-continued tggaacaatt cacaaacata tgtcct 26

<210> SEQ ID NO 21
<211> LENGTH: 168
<212> TYPE: DNA
<213> ORGANISM: Influenza A virus

<400> SEQUENCE: 21
tgtccagagc tcctcgagat ggaatggcta aagacaagac caatcttgtc acctctgact 60
aagggaattt taggatttgt gttcacgctc accgtgccca gtgagcgagg actgcagcgt 120
agacgctttg tccaaaatgc cctaaatggg aatggggacc cgtctaga 168

<210> SEQ ID NO 22
<211> LENGTH: 156
<212> TYPE: DNA
<213> ORGANISM: Influenza B virus

<400> SEQUENCE: 22
aacaacatgg ccatcggatc ctcaattcac tcttcgagcg tcttaatgaa ggacattcaa 60
agccaattcg agcagctgaa actgcggtgg gagtcttatc ccaatttggt caagagcacc 120
gactatcacc agaagaggga gacaaaacag actagt 156

<210> SEQ ID NO 23
<211> LENGTH: 150
<212> TYPE: DNA
<213> ORGANISM: Severe acute respiratory syndrome coronavirus 2

<400> SEQUENCE: 23
caaactgtga ctcttcttcc tgctgcagat ttggatgatt tctccaaaca attgcaacaa 60
tccatgagca gtgctgactc aactcaggcc taaactcatg cagaccacac aaggcagatg 120
ggctatataa acgttttcgc ttttcatatg 150

<210> SEQ ID NO 24
<211> LENGTH: 129
<212> TYPE: DNA
<213> ORGANISM: Homo sapiens

<400> SEQUENCE: 24
ccgtttacga tggcggtgtt tgcagatttg gacctgcgag cgggttctga cctgaaggct 60
ctgcgcggac ttgtggagac agccgctcac cttggctatt cagttgttgc tatcaatcca 120
tggggtacc 129

<210> SEQ ID NO 25
<211> LENGTH: 127
<212> TYPE: DNA
<213> ORGANISM: Human respiratory syncytial virus A

<400> SEQUENCE: 25
ttacatattc aatggtcctt atctcaaaaa tgattatacc aacttaatta gtagacaaaa 60
tccattaata gaacacataa atctaaagaa actaaatata acacagtcct taatatctaa 120
gtatcat 127

<210> SEQ ID NO 26
<211> LENGTH: 127
<212> TYPE: DNA
<213> ORGANISM: Human respiratory syncytial virus B

<400> SEQUENCE: 26
gacattgtgt ttcaaaattg cataagtttt ggtcttagct tgatgtcagt tgtggaacaa 60
ttcacaaaca tatgtcctaa tagaattatt ctcataccga agctgaatga gatacatttg 120
atgaaac 127

<210> SEQ ID NO 27
<211> LENGTH: 798
<212> TYPE: DNA
<213> ORGANISM: Escherichia coli

<400> SEQUENCE: 27
atgattgaac aggatggcct gcatgcgggt agcccggcag cgtgggtgga acgtctgttt 60
ggctatgatt gggcgcagca gaccattggc tgctctgatg cggcggtgtt tcgtctgagc 120
gcgcagggtc gtccggtgct gtttgtgaaa accgatctga gcggtgcgct gaacgagctg 180
caggatgaag cggcgcgtct gagctggctg gccaccaccg gtgttccgtg tgcggcggtg 240
ctggatgtgg tgaccgaagc gggccgtgat tggctgctgc tgggcgaagt gccgggtcag 300
gatctgctgt ctagccatct ggcgccggca gaaaaagtga gcattatggc ggatgccatg 360
cgtcgtctgc ataccctgga cccggcgacc tgtccgtttg atcatcaggc gaaacatcgt 420
attgaacgtg cgcgtacccg tatggaagcg ggcctggtgg atcaggatga tctggatgaa 480
gaacatcagg gcctggcacc ggcagagctg tttgcgcgtc tgaaagcgag catgccggat 540
ggcgaagatc tggtggtgac ccatggtgat gcgtgcctgc cgaacattat ggtggaaaat 600
ggccgtttta gcggctttat tgattgcggc cgtctgggcg tggcggatcg ttatcaggat 660
attgcgctgg ccacccgtga tattgcggaa gaactgggcg gcgaatgggc ggatcgtttt 720
ctggtgctgt atggcattgc ggcaccggat agccagcgta ttgcgtttta tcgtctgctg 780
gatgaatttt tctaataa 798

<210> SEQ ID NO 28
<211> LENGTH: 2896
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtggccgct acagggcgct cccattcgcc attcaggctg cgcaactgtt 180
gggaagggcg tttcggtgcg ggcctcttcg ctattacgcc agctggcgaa agggggatgt 240
gctgcaaggc gattaagttg ggtaacgcca gggttttccc agtcacgacg ttgtaaaacg 300
acggccagtg agcgcgacgt aatacgactc actatagggc gaattgaagg aaggccgtca 360
aggccacgtg tcttgtccag agctcctcga gatggaatgg ctaaagacaa gaccaatctt 420
gtcacctctg actaagggaa ttttaggatt tgtgttcacg ctcaccgtgc ccagtgagcg 480
aggactgcag cgtagacgct ttgtccaaaa tgccctaaat gggaatgggg acccgtctag 540
aaacaacatg gccatcggat cctcaattca ctcttcgagc gtcttaatga aggacattca 600
aagccaattc gagcagctga aactgcggtg ggagtcttat cccaatttgg tcaagagcac 660
cgactatcac cagaagaggg agacaaaaca gactagtcaa actgtgactc ttcttcctgc 720

```
tgcagatttg gatgatttct ccaaacaatt gcaacaatcc atgagcagtg ctgactcaac    780

tcaggcctaa actcatgcag accacacaag gcagatgggc tatataaacg ttttcgcttt    840

tcatatgccg tttacgatgg cggtgtttgc agatttggac ctgcgagcgg gttctgacct    900

gaaggctctg cgcggacttg tggagacagc cgctcacctt ggctattcag ttgttgctat    960

caatccatgg ggtacctgga gcacaagact ggcctcatgg gccttccttt cactgcccgc   1020

tttccagtcg ggaaacctgt cgtgccagct gcattaacat ggtcatagct gtttccttgc   1080

gtattgggcg ctctccgctt cctcgctcac tgactcgctg cgctcggtcg ttcgggtaaa   1140

gcctggggtg cctaatgagc aaaaggccag caaaaggcca ggaaccgtaa aaaggccgcg   1200

ttgctggcgt ttttccatag gctccgcccc cctgacgagc atcacaaaaa tcgacgctca   1260

agtcagaggt ggcgaaaccc gacaggacta taaagatacc aggcgtttcc ccctggaagc   1320

tccctcgtgc gctctcctgt tccgaccctg ccgcttaccg gatacctgtc cgcctttctc   1380

ccttcgggaa gcgtggcgct ttctcatagc tcacgctgta ggtatctcag ttcggtgtag   1440

gtcgttcgct ccaagctggg ctgtgtgcac gaaccccccg ttcagcccga ccgctgcgcc   1500

ttatccggta actatcgtct tgagtccaac ccggtaagac acgacttatc gccactggca   1560

gcagccactg gtaacaggat tagcagagcg aggtatgtag gcggtgctac agagttcttg   1620

aagtggtggc ctaactacgg ctacactaga agaacagtat ttggtatctg cgctctgctg   1680

aagccagtta ccttcggaaa aagagttggt agctcttgat ccggcaaaca aaccaccgct   1740

ggtagcggtg gtttttttgt ttgcaagcag cagattacgc gcagaaaaaa aggatctcaa   1800

gaagatcctt tgatcttttc tacggggtct gacgctcagt ggaacgaaaa ctcacgttaa   1860

gggattttgg tcatgagatt atcaaaaagg atcttcacct agatcctttt aaattaaaaa   1920

tgaagtttta aatcaatcta aagtatatat gagtaaactt ggtctgacag ttattagaaa   1980

aattcatcca gcagacgata aaacgcaata cgctggctat ccggtgccgc aatgccatac   2040

agcaccagaa aacgatccgc ccattcgccg cccagttctt ccgcaatatc acgggtggcc   2100

agcgcaatat cctgataacg atccgccacg cccagacggc cgcaatcaat aaagccgcta   2160

aaacggccat tttccaccat aatgttcggc aggcacgcat caccatgggt caccaccaga   2220

tcttcgccat ccggcatgct cgctttcaga cgcgcaaaca gctctgccgg tgccaggccc   2280

tgatgttctt catccagatc atcctgatcc accaggcccg cttccatacg ggtacgcgca   2340

cgttcaatac gatgtttcgc ctgatgatca aacggacagg tcgccgggtc cagggtatgc   2400

agacgacgca tggcatccgc cataatgctc actttttctg ccggcgccag atggctagac   2460

agcagatcct gacccggcac ttcgcccagc agcagccaat cacggcccgc ttcggtcacc   2520

acatccagca ccgccgcaca cggaacaccg gtggtggcca gccagctcag acgcgccgct   2580

tcatcctgca gctcgttcag cgcaccgctc agatcggttt tcacaaacag caccggacga   2640

ccctgcgcgc tcagacgaaa caccgccgca tcagagcagc caatggtctg ctgcgcccaa   2700

tcatagccaa acagacgttc cacccacgct gccgggctac ccgcatgcag gccatcctgt   2760

tcaatcatac tcttcctttt tcaatattat tgaagcattt atcagggtta ttgtctcatg   2820

agcggataca tatttgaatg tatttagaaa aataaacaaa taggggttcc gcgcacattt   2880

ccccgaaaag tgccac                                                   2896
```

<210> SEQ ID NO 29
<211> LENGTH: 3605
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 29

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagagaatt cgagctcggt acctcgcgaa    420
tacatctaga tctcgagatt caggttacat attcaatggt ccttatctca aaaatgatta    480
taccaactta attagtagac aaaatccatt aatagaacac ataaatctaa agaaactaaa    540
tataacacag tccttaatat ctaagtatca taaaggtgaa ataaaaatag aagaacctac    600
ttactttcag tcattactta tgacatacaa gagtatgacc tcgtcagaac agactactac    660
tactaattta cttaaaaaga taataagaag agctcgacat tgtgtttcaa aattgcataa    720
gttttggtct tagcttgatg tcagttgtgg aacaattcac aaacatatgt cctaatagaa    780
ttattctcat accgaagctg aatgagatac atttgatgaa acctcctata tttacaggag    840
atgttgatat catcaagttg aagcaagtga tacaaaaaca ggaatggcta aagacaagac    900
caatcttgtc acctctgact aagggaattt taggatttgt gttcacgctc accgtgccca    960
gtgagcgagg actgcagcgt agacgctttg tccaaaatgc cctaaatggg aatggggacc   1020
cgtctagaaa caacatggcc atcggatcct caattcactc ttcgagcgtc ttaatgaagg   1080
acattcaaag ccaattcgag cagctgaaac tgcggtggga gtcttatccc aatttggtca   1140
agagcaccga ctatcaccag aagagggaga caaaacagac tagtcaaact gtgactcttc   1200
ttcctgctgc agatttggat gatttctcca aacaattgca acaatccatg agcagtgctg   1260
actcaactca ggcctaaact catgcagacc acacaaggca gatgggctat ataaacgttt   1320
tcgcttttca tatgccgttt acgatggcgg tgtttgcaga tttggacctg cgagcgggtt   1380
ctgacctgaa ggctctgcgc ggacttgtgg agacagccgc tcaccttggc tattcagttg   1440
ttgctatcaa tccatggatc ggatcccggg cccgtcgact gcagaggcct gcatgcaagc   1500
ttggtgtaat catggtcata gctgtttcct gtgtgaaatt gttatccgct cacaattcca   1560
cacaacatac gagccggaag cataaagtgt aaagcctggg gtgcctaatg agtgagctaa   1620
ctcacattaa ttgcgttgcg ctcactgccc gctttccagt cgggaaacct gtcgtgccag   1680
ctgcattaat gaatcggcca acgcgcgggg agaggcggtt tgcgtattgg gcgctcttcc   1740
gcttcctcgc tcactgactc gctgcgctcg gtcgttcggc tgcggcgagc ggtatcagct   1800
cactcaaagg cggtaatacg gttatccaca gaatcagggg ataacgcagg aaagaacatg   1860
tgagcaaaag gccagcaaaa ggccaggaac cgtaaaaagg ccgcgttgct ggcgtttttc   1920
cataggctcc gcccccctga cgagcatcac aaaaatcgac gctcaagtca gaggtggcga   1980
aacccgacag gactataaag ataccaggcg tttccccctg gaagctccct cgtgcgctct   2040
cctgttccga ccctgccgct taccggatac ctgtccgcct ttctcccttc gggaagcgtg   2100
gcgctttctc atagctcacg ctgtaggtat ctcagttcgg tgtaggtcgt tcgctccaag   2160
ctgggctgtg tgcacgaacc ccccgttcag cccgaccgct gcgccttatc cggtaactat   2220
```

-continued

```
cgtcttgagt ccaacccggt aagacacgac ttatcgccac tggcagcagc cactggtaac   2280

aggattagca gagcgaggta tgtaggcggt gctacagagt tcttgaagtg gtggcctaac   2340

tacggctaca ctagaagaac agtatttggt atctgcgctc tgctgaagcc agttaccttc   2400

ggaaaaagag ttggtagctc ttgatccggc aaacaaacca ccgctggtag cggtggtttt   2460

tttgtttgca agcagcagat tacgcgcaga aaaaaaggat ctcaagaaga tcctttgatc   2520

ttttctacgg ggtctgacgc tcagtggaac gaaaactcac gttaagggat tttggtcatg   2580

agattatcaa aaaggatctt cacctagatc cttttaaatt aaaaatgaag ttttaaatca   2640

agcccaatct gaataatgtt acaaccaatt aaccaattct gattagaaaa actcatcgag   2700

catcaaatga aactgcaatt tattcatatc aggattatca ataccatatt tttgaaaaag   2760

ccgtttctgt aatgaaggag aaaactcacc gaggcagttc cataggatgg caagatcctg   2820

gtatcggtct gcgattccga ctcgtccaac atcaatacaa cctattaatt tcccctcgtc   2880

aaaaataagg ttatcaagtg agaaatcacc atgagtgacg actgaatccg gtgagaatgg   2940

caaaagttta tgcatttctt tccagacttg ttcaacaggc cagccattac gctcgtcatc   3000

aaaatcactc gcatcaacca aaccgttatt cattcgtgat tgcgcctgag cgagacgaaa   3060

tacgcgatcg ctgttaaaag gacaattaca aacaggaatc gaatgcaacc ggcgcaggaa   3120

cactgccagc gcatcaacaa tattttcacc tgaatcagga tattcttcta atacctggaa   3180

tgctgttttt ccggggatcg cagtggtgag taaccatgca tcatcaggag tacggataaa   3240

atgcttgatg gtcggaagag gcataaattc cgtcagccag tttagtctga ccatctcatc   3300

tgtaacatca ttggcaacgc tacctttgcc atgtttcaga aacaactctg gcgcatcggg   3360

cttcccatac aagcgataga ttgtcgcacc tgattgcccg acattatcgc gagcccattt   3420

atacccatat aaatcagcat ccatgttgga atttaatcgc ggcctcgacg tttcccgttg   3480

aatatggctc ataacacccc ttgtattact gtttatgtaa gcagacagtt ttattgttca   3540

tgatgatata tttttatctt gtgcaatgta acatcagaga ttttgagaca cgggccagag   3600

ctgca                                                                3605
```